United States Patent
Xie et al.

(10) Patent No.: US 8,981,051 B2
(45) Date of Patent: *Mar. 17, 2015

(54) NA+/K+-ATPASE-SPECIFIC PEPTIDE INHIBITORS/ACTIVATORS OF SRC AND SRC FAMILY KINASES

(71) Applicant: The University of Toledo, Toledo, OH (US)

(72) Inventors: Zi-Jian Xie, Saline, MI (US); Joseph I. Shapiro, Toledo, OH (US); Jiang Tian, Perrysburg, OH (US); Zhichuan Li, Williamsville, NY (US)

(73) Assignee: The University of Toledo, Toledo, OH (US)

( * ) Notice: Subject to any disclaimer, the term of this patent is extended or adjusted under 35 U.S.C. 154(b) by 193 days.

This patent is subject to a terminal disclaimer.

(21) Appl. No.: 13/625,162

(22) Filed: Sep. 24, 2012

(65) Prior Publication Data

US 2013/0150294 A1   Jun. 13, 2013

Related U.S. Application Data

(62) Division of application No. 12/446,856, filed as application No. PCT/US2007/023011 on Oct. 31, 2007, now Pat. No. 8,283,441.

(60) Provisional application No. 60/855,482, filed on Oct. 21, 2006.

(51) Int. Cl.
| | |
|---|---|
| A61K 38/10 | (2006.01) |
| C07K 14/47 | (2006.01) |
| A61K 38/45 | (2006.01) |
| A61K 38/46 | (2006.01) |
| C07K 7/08 | (2006.01) |
| G01N 33/573 | (2006.01) |

(52) U.S. Cl.
CPC .............. *C07K 14/4703* (2013.01); *A61K 38/45* (2013.01); *A61K 38/46* (2013.01); *C07K 7/08* (2013.01); *C07K 14/4705* (2013.01); *G01N 33/573* (2013.01); *C12Y 306/03009* (2013.01); *C12Y 207/10002* (2013.01)
USPC .......................................... 530/324; 530/326

(58) Field of Classification Search
CPC ................ C12Y 207/1002; C12Y 306/03009; A61K 38/45; C07K 14/4703; C07K 14/4705; C07K 7/08
See application file for complete search history.

(56) References Cited

U.S. PATENT DOCUMENTS

| | | |
|---|---|---|
| 2,698,822 A | 1/1955 | Halpern et al. |
| 3,122,475 A | 2/1964 | Schaeppi |
| 3,687,944 A | 8/1972 | Pettit et al. |
| 4,261,971 A | 4/1981 | Appelgren et al. |
| 5,153,178 A | 10/1992 | Maroko |
| 5,888,527 A | 3/1999 | Nashimoto et al. |
| 5,965,540 A | 10/1999 | Waller |
| 5,989,591 A | 11/1999 | Nagi |
| 6,071,885 A | 6/2000 | Florkiewicz |
| 6,113,965 A | 9/2000 | Goodsall et al. |
| 6,261,760 B1 | 7/2001 | Fielding et al. |
| 6,562,864 B1 | 5/2003 | Larson |
| 6,726,935 B2 | 4/2004 | Ji et al. |
| 7,078,060 B2 | 7/2006 | Burrell et al. |
| 7,157,493 B2 | 1/2007 | Zhao et al. |
| 7,195,783 B2 | 3/2007 | Shan et al. |
| 7,402,325 B2 | 7/2008 | Addington |
| 7,858,126 B2 | 12/2010 | Singh et al. |
| 8,283,441 B2 | 10/2012 | Xie et al. |
| 8,394,434 B2 | 3/2013 | Addington et al. |
| 2002/0039764 A1 | 4/2002 | Rosen et al. |
| 2002/0055644 A1 | 5/2002 | Winter et al. |
| 2002/0091085 A1 | 7/2002 | Kay et al. |
| 2002/0168425 A1 | 11/2002 | Nakayama et al. |
| 2004/0229275 A1 | 11/2004 | Hayden et al. |
| 2005/0026849 A1 | 2/2005 | Singh et al. |
| 2005/0271606 A1 | 12/2005 | Iwasaki et al. |
| 2006/0004002 A1 | 1/2006 | Thrash |
| 2006/0035835 A1 | 2/2006 | Taniyama et al. |
| 2006/0094772 A1 | 5/2006 | Chang et al. |

(Continued)

FOREIGN PATENT DOCUMENTS

| | | |
|---|---|---|
| CN | 101374571 A | 2/2009 |
| CN | 101541319 A | 9/2009 |

(Continued)

OTHER PUBLICATIONS

Li et al, NaKtide, a Na/K-ATPase-derived peptide Src inhibitor, antagonizes ouabain-activated signal transduction in cultured cells. J Biol Chem. Jul. 31, 2009;284(31):21066-76. doi: 10.1074/jbc.M109.013821. Epub Jun. 8, 2009.*
Skhirtladze et al, Src Kinases in Systemic Sclerosis. Arthritis & Rheumatism vol. 58, No. 5, May 2008, pp. 1475-1484.*
Canadian Notice of Allowance, Application No. 2,641,303, dated Jan. 7, 2013 [2-51126/UT-D2006-10].
Canadian Notice of Requisition by the Examiner, Application No. 2,667,251, dated Dec. 13, 2013, [2-28445/UT-D2007-01].
Chinese 1st Office Action, Application No. 201180010298.9, dated Aug. 16, 2013, [55-52651/UT-D-2010-26(2)].

(Continued)

*Primary Examiner* — Sheridan Swope
(74) *Attorney, Agent, or Firm* — MacMillan, Sobanski & Todd, LLC

(57) ABSTRACT

A method for regulating Src and its downstream signaling pathway which includes binding between Src and Na+/K+-ATPase is disclosed. The Na+/K+-ATPase/Src complex is a functional receptor for cardiotonic steroids such as ouabain. Also disclosed are Src inhibitors or activators which include either Na+/K+-ATPase or Src that interfere with the interaction between the Na/K-ATPase and Src, act via a different mechanism from ATP analogs, and is pathway (Na+/K+-ATPase) specific.

6 Claims, 43 Drawing Sheets
(16 of 43 Drawing Sheet(s) Filed in Color)

(56) References Cited

U.S. PATENT DOCUMENTS

| | | | |
|---|---|---|---|
| 2006/0135468 | A1 | 6/2006 | Khodadoust |
| 2006/0205679 | A1 | 9/2006 | Streeper et al. |
| 2007/0092970 | A1 | 4/2007 | Liang |
| 2007/0092972 | A1 | 4/2007 | Xiao et al. |
| 2007/0098765 | A1 | 5/2007 | Zhao et al. |
| 2007/0161589 | A1 | 7/2007 | Bennett et al. |
| 2008/0317878 | A1 | 12/2008 | Li et al. |
| 2009/0082293 | A1 | 3/2009 | Giordano et al. |
| 2009/0143279 | A1 | 6/2009 | Mootha et al. |
| 2009/0226513 | A1 | 9/2009 | Xie et al. |
| 2010/0056446 | A1 | 3/2010 | Xie et al. |
| 2010/0092585 | A1 | 4/2010 | Smothers |
| 2011/0245167 | A1 | 10/2011 | Xie et al. |
| 2012/0302630 | A1 | 11/2012 | Xie et al. |
| 2013/0011335 | A1 | 1/2013 | Xie et al. |

FOREIGN PATENT DOCUMENTS

| | | | |
|---|---|---|---|
| WO | 97/34482 | A1 | 9/1997 |
| WO | 02/14343 | A1 | 2/2002 |
| WO | 02/092573 | A2 | 11/2002 |
| WO | 03/016475 | A2 | 2/2003 |
| WO | 2004/004785 | A1 | 1/2004 |
| WO | 2004/043384 | A2 | 5/2004 |
| WO | WO2005117932 | * | 12/2005 |
| WO | 2007/023011 | A2 | 3/2007 |
| WO | 2007/089688 | A2 | 8/2007 |
| WO | 2007/130124 | A1 | 11/2007 |
| WO | 2008/054792 | A2 | 5/2008 |
| WO | 2010/053771 | A1 | 5/2010 |
| WO | 2010/071767 | A2 | 6/2010 |
| WO | 2011/034772 | A1 | 3/2011 |
| WO | 2011/088208 | A1 | 7/2011 |
| WO | 2011/088210 | A1 | 7/2011 |

OTHER PUBLICATIONS

Chinese 2nd Office Action, Application No. 200980149736.2, dated Oct. 15, 2013, [55-50445/UT-D2009-07].
Chinese 3rd Office Action, Application No. 200780043725.7, dated Jun. 12, 2012 [55-28445/UT-2007-01].
Chinese 4th Office Action, Application No. 200780043725.7, dated Nov. 15, 2012 [55-28445/UT-2007-01].
Chinese First Office Action, Application No. 200780003862.8, dated Jun. 30, 2011 [55-51126/UT-D2006-10].
Chinese First Office Action, Application No. 201180010295.5, dated May 22, 2013, [55-51488/UT-2010-26(1)].
Chinese Notification of the First Office Action, Appln. No. 201080046743.2, dated Apr. 25, 2013, [55-51181/UT-D2010-02].
Chinese Office Action, Application No. 200780043725.7 dated Jan. 12, 2011.
Chinese Office Action, Application No. 200780003862.8 dated Dec. 5, 2012, 55-51126/D2006-10.
Chinese Office Action, Application No. 200980149736.2 dated Nov. 28, 2012, 55-50445/D2009-07.
Chinese Office Action, Application No. 200780003862.8 dated May 30, 2012, 55-51126/D2006-10.
Chinese Second Office Action, Application No. 201180010295.5, dated Jan. 13, 2014 [55-51488/UT-2010-26(1)].
Chinese Second Office Action, Application No. 200780043725.7, dated Nov. 16, 2011 [55-28445/UT-2007-01].
EP Communication Pursuant to Article 94(3) EPC, Application No. 07762999.6, dated Oct. 13, 2009 [57-51126/UT-D2006-10].
EP Communication Pursuant to Article 94(3) EPC, Application No. 07762999.6, dated Jul. 23, 2010 [57-51126/UT-D2006-10].
EP Communication, Application No. 07762999.6, dated Aug. 18, 2009 [57-51126/UT-D2006-10].
EP Communication, Application No. 10817681.9, dated Mar. 7, 2013, [57-51181/UT-D2010-02].
EP Communication, Application No. 07867328.2, dated Nov. 6, 2013, [57-28445/UT-2007-01].

EP Communication, Application No. 10817681.9, dated Feb. 26, 2014, [57-51181/UT-D2010-02].
European Supplementary Search Report, Application No. 07762999.6 dated Sep. 4, 2009.
PCT International Preliminary Report on Patentability, PCT/US2009/062317 filed Oct. 28, 2009, dated May 12, 2011, 53-50446.
PCT International Preliminary Report on Patentability, PCT/US07/023011 filed Oct. 31, 2007, dated May 14, 2009, 53-28445.
PCT International Preliminary Report on Patentability, PCT/US09/067845 filed Dec. 14, 2009, dated Jun. 23, 2011, 53-50445.
PCT International Search Report and the Written Opinion, PCT/US11/21127 filed Jan. 13, 2011, dated Apr. 13, 2011, 53-51488.
PCT International Search Report and the Written Opinion, PCT/US10/48227 filed Sep. 9, 2010, dated Nov. 8, 2010, 53-51181.
PCT International Search Report and Written Opinion, Application No. 2013/040181, dated Oct. 25, 2013 [53-53880/UT-D2012-13].
PCT International Search Report and the Written Opinion, PCT/US09/62317 filed Oct. 28, 2009, dated Mar. 2, 2010, 53-50446.
PCT International Search Report and the Written Opinion, PCT/US07/23011 filed Oct. 31, 2007, dated Sep. 26, 2008, 53-28445.
PCT International Search Report and the Written Opinion, PCT/US07/02365 filed Jan. 30, 2007, dated Dec. 20, 2007.
PCT International Search Report and the Written Opinion, PCT/US11/21130 filed Jan. 13, 2011, dated Jun. 7, 2011, 53-52651.
PCT International Search Report and the Written Opinion, PCT/US09/67845 filed Dec. 14, 2009, dated Aug. 10, 2010, 53-50445.
Amigo, L. et al., "Enrichment of Canalicular Membrane with Cholesterol and Sphingomyelin Prevents Bile Salt-Induced Hepatic Damage," Journal of Lipid Research, 1999, pp. 533-542, vol. 40.
Aydemir-Koksoy, A. et al., "Ouabain-Induced Signaling and Vascular Smooth Muscle Cell Proliferation," The Journal of Biological Chemistry, 2001, pp. 46605-46611, vol. 276, No. 49.
Bork, "Powers and Pitfalls in Sequence Analysis: The 70% Hurdle", Genome Research, 2000, 10, pp. 398-400.
Brenner, "Errors in Genome Annotation", Trends in Genetics, 1999, 15(4), pp. 132-133.
Cai, T. et al., "Regulation of Caveolin-1 Membrane Trafficking by the Na/K-ATPase," Journal of Cell Biology, 2008, pp. 1153-1169, vol. 182, No. 6.
Chan, et al., Interactions between traditional Chinese medicines and Western therapeutics, Current Opinion in Drug Discovery & Development, 2010, 13 (1), pp. 50-65.
Chen, Y. et al., "Regulation of Intracellular Cholesterol Distribution by Na/K-ATPase," The Journal of Biological Chemistry, May 2009, pp. 14881-14890, vol. 284, No. 22.
Chen, Y., "The N-Terminus of a1 Subunit and Na/K-ATPase-Mediated Signal Transduction," Final Approval of Dissertation, The University of Toledo, College of Medicine, 2009.
Chong, Y.P. et al., "Endogenous and Synthetic Inhibitors of the SRC-Family Protein Tyrosine Kinases," Biochimica et Biophysica Acta., Dec. 2005, pp. 210-220, vol. 1754, Nos. 1-2.
Cooper, R. et al., "Medicinal Benefits of Green Tea: Part I. Review of Noncancer Health Benefits," The Journal of Alternative and Complementary Medicine, 2005, pp. 521-528, vol. 11, No. 3.
Cruz, J.C. et al., "Role of Niemann-Pick Type C1 Protein in Intracellular Trafficking of Low Density Lipoprotein-Derived Cholesterol," The Journal of Biological Chemistry, 2000, pp. 4013-4021, vol. 275, No. 6.
Darra, E. et al., "Protective Effect of Epigallocatechin-3-Gallate on Ischemia/Reperfusion-Induced Injuries in the Heart: STAT1 Silencing Flavenoid," Genes Nutr., 2007, pp. 307-310, vol. 2.
Dmitrieva, R.I. et al., "Cardiotonic Steroids: Potential Endogenous Sodium Pump Ligands with Diverse Function," Exp. Biol. Med., 2002, pp. 561-569, vol. 227, No. 8.
Doerks, et al., "Protein Annotation: Detective Work for Function Prediction", Trends in Genetics, 1998, 14(6), pp. 248-250.
Donovan, et al., The Effect of Age on Digitoxin Pharmacokinetics, Br. J. Clin. Pharmac., 1981.
Elkareh, J. et al., "Marinobufagenin Stimulates Fibroblast Collagen Production and Causes Fibrosis in Experimental Uremic Cardiomyopathy," Hypertension, 2007, pp. 215-224, vol. 49.

(56) References Cited

OTHER PUBLICATIONS

El-Okdi, N. et al., "Effects of Cardiotonic Steroids on Dermal Collagen Synthesis and Wound Healing," J. Appl. Physiol., 2008, pp. 30-36, vol. 105.

Haas, M. et al., "SRC-Mediated Inter-Receptor Cross-Talk Between the Na+/K+-ATPase and the Epidermal Growth Factor Receptor Relays the Signal from Ouabain to Mitogen-Activated Protein Kinases," The Journal of Biological Chemistry, 2002, pp. 18694-18702, vol. 277, No. 21.

Hotta, Y. et al., "Positive Inotropic Effect of Purified Green Tea Catechin Derivative in Guinea Pig Hearts: The Measurements of Cellular Ca2+ and Nitric Oxide Release," European Journal of Pharmacology, 2006, pp. 123-130, vol. 552.

Ignatushchenko, et al., Xanthones as Antimalarial Agents: Stage Specificity, Am. J. Trop. Med. Hyg., 62 (1) 2000, pp. 77-81.

Ikeda, I. et al., "Tea Catechins with a Galloyl Moiety Suppress Postprandial Hypertriacylglycerolemia by Delaying Lymphatic Transport of Dietary Fat in Rats," The Journal of Nutrition, 2005, pp. 155-159, vol. 135.

Kabat, M.M. et al., "Cardiotonic Steroids. 5. A Synthesis of Bufadienolides and Cardenolides from 3β-Acetoxy-5-Androsten-17-One via Common Intermediates," J. Org. Chem., 1983, pp. 4248-4251, vol. 48.

Katz, B. et al., "Controlled-Release Drug Delivery Systems in Cardiovascular Medicine," American Heart Journal, 1995, pp. 359-368, vol. 129, No. 2.

Kennedy, D.J. et al., "Central Role for the Cardiotonic Steroid Marinobufagenin in the Pathogenesis of Experimental Uremic Cardiomyopathy," Hypertension, 2006, pp. 488-495, vol. 47.

Khundmiri, S.J. et al., "Ouabine Induces Cell Proliferation through Calcium-Dependent Phosphorylation of Akt (Protein Kinase B) in Opossum Kidney Proximal Tubule Cells," Am. J. Physiol. Cell Physiol., 2006, pp. C1247-C1257, vol. 291.

Kubota, Y. et al., "Safety of Dietary Supplements; Chronotropic and Inotropic Effects on Isolated Rat Atria," Biol. Pharm Bull., 2002, pp. 197-200, vol. 25, No. 2.

Laird, A.D. et al., "Src Family Kinase Activity is Required for Signal Tranducer and Activator of Transcription 3 and Focal Adhesion Kinase Phosphorylation and Vascular Endothelial Growth Factor Signaling in Vivo and for Anchorage-Dependent and -Independent Growth of Human Tumor Cells," Molecular Cancer Therapeutics, May 2003, pp. 461-469, vol. 2.

LeFranc, F. et al., "Targeting the α1 Subunit of the Sodium Pump to Combat Glioblastoma Cells," Neurosurgery, Jan. 2008, pp. 211-222, vol. 62, No. 1.

Li, Z. et al., "Na/K-ATPase Mimetic pNaKtide Peptide Inhibits the Growth of Human Cancer Cells," Journal of Biological Chemistry, Jul. 2011, pp. 32394-32403, vol. 286, No. 37.

Li, Z. et al., "NaKtide, a Na/K-ATPase-Derived Peptide SRC Inhibitor, Antagonizes Ouabain-Activated Signal Transduction in Cultured Cells," Journal of Biological Chemistry, Jun. 2009, pp. 21066-21076, vol. 284, No. 31.

Li, Z. et al., "The Na/K-ATPAse/SRC Complex and Cardiotonic Steroid-Activated Protein Kinase Cascades," Pflugers Archiv, Feb. 2008, pp. 635-644, vol. 457, No. 3.

Liang, M. et al., "Identification of a Pool of Non-Pumping Na/K-Atpase," Journal of Biological Chemistry, Feb. 2007, pp. 10585-10593, vol. 282, No. 14.

Liang, M. et al., "Functional Characterization of Src-lnteracting Na/K-ATPase Using RNA Interference Assay," The Journal of Biological Chemistry, Jul. 2006, pp. 19709-19719, vol. 281, No. 28.

Melero, et al., A Short Review on Cardiotonic Steriods and Their Aminoguanidine Analogues, Molecules 2000, 5, pp. 51-81.

Newman, R.A. et al., "Cardiac Glycosides as Novel Cancer Therapeutic Agents," Molecular Interventions, Feb. 2008, pp. 36-49, vol. 8, Issue 1.

Ngo, et al., Computational Complexity Protein Structure Prediction, and the Levinthal Paradox, Chapter 14, 1994, pp. 433-440 and 492-495 only.

Paquay, J.B.G. et al., "Protection Against Nitric Oxide Toxicity by Tea," J. Agric. Food Chem., 2000, pp. 5768-5772, vol. 48.

Pedro, et al., Xanthones as Inhibitors of Growth of Human Cancer Cell Lines and Their Effects on the Proliferation of Human Lymphocytes In Vitro, Bioorganic & Medicinal Chemistry 2002, 10, pp. 3725-3730.

Robia, S.L. et al., "Localization and Kinetics of Protein Kinase C-Epsilon Anchoring in Cardiac Myocytes," Biophysical Journal, May 2001, pp. 2140-2151, vol. 80.

Sato, A. et al., "α-Mangostin Induces Ca2+-ATPase-Dependent Apoptosis via Mitochondrial Pathway in PC12 Cells," Journal of Pharmacological Sciences, 2004, pp. 33-40, vol. 95.

Schulte, R. et al., "Inhibition of the Activity of SRC and ABL Tyrosine Protein Kinases by the Binding of the Wiskott-Aldrich Syndrome Protein," Biochemistry, Aug. 2003, pp. 9424-9430, vol. 42, No. 31.

Skolnick, et al., From Genes to Protein Structure and Function: Novel Applications of Computational Approaches in the Genomic Era, Trends in Biotech, 2000, 18(1), pp. 34-39.

Susva, M. et al., "SRC Inhibitors: Drugs for the Treatment of Osteoporosis, Cancer or Both?" Trends in Pharmacological Sciences, Dec. 2000, pp. 489-495, vol. 21, No. 12.

Tian, J. et al., "Binding of Src to Na+/K+ATPase Forms a Functional Signaling Complex," Molecualr Biology of the Cell, Jan. 2006, pp. 317-326, vol. 17.

Tian, J. et al., "Changes in Sodium Pump Expression Dictate the Effect s of Ouabine on Cell Growth," The Journal of Biological Chemistry, May 2009, pp. 14921-14929, vol. 284, No. 22.

Tian, J. et al., "Na/K-ATPase Moonlights via Ouabine-Regulated Interaction with Src," Abstract, The FASEB Journal, Mar. 2004, vol. 18, No. 5.

Townsend, P.A. et al., "Epigallocatechin-3-Gallate Inhibits STAT-1 Activation and Protects Cardiac Myocytes from Ischemia/Reperfusion-Induced Apoptosis," The FASEB Journal, 2004, doi: 10.1096/fj.04-1716fje.

Urano, Y. et al., "Transport of LDL-Derived Cholesterol from the NPC1 Compartment to the ER Involves the Trans-Golgi Network and the SNARE Protein Complex," PNAS, Oct. 2008, pp. 16513-16518, vol. 105, No. 43.

Wang, H., "Na+/K+ATPase and Signal Transduction," Final Approval of Dissertation, The University of Toledo, College of Medicine, 2005.

Wells, Additivity of Mutational Effects in Proteins, Biochemisty, 1990, vol. 29, No. 37, pp. 8509-8517.

Yang, et al., Cardiac glycosides inhibit TNF-a/Nf-kB signaling by blocking recruitment of TNF receptor-associated death domain to the TNF receptor, PNAS, Jul. 5, 2005, vol. 102, No. 27, pp. 9631-9636.

Yeatman, T.J., "A Renaissance for SRC," Nature Reviews Cancer, Jun. 2004, pp. 470-480, vol. 4, No. 6.

Zhang, Z. et al., "Identification of Hyroxyxanthones as Na/K-ATPase Ligands," Molecular Pharmacology, 2010, pp. 961-967, vol. 77, No. 6.

Zhong, et al., 3,4,5,6,-Tetrahydroxyxanthone Protects Against Myocardial lschemia-Reperfusion Injury in Rats, Cardiovascular Drugs and Therapy, 2004, 18, pp. 279-288.

* cited by examiner

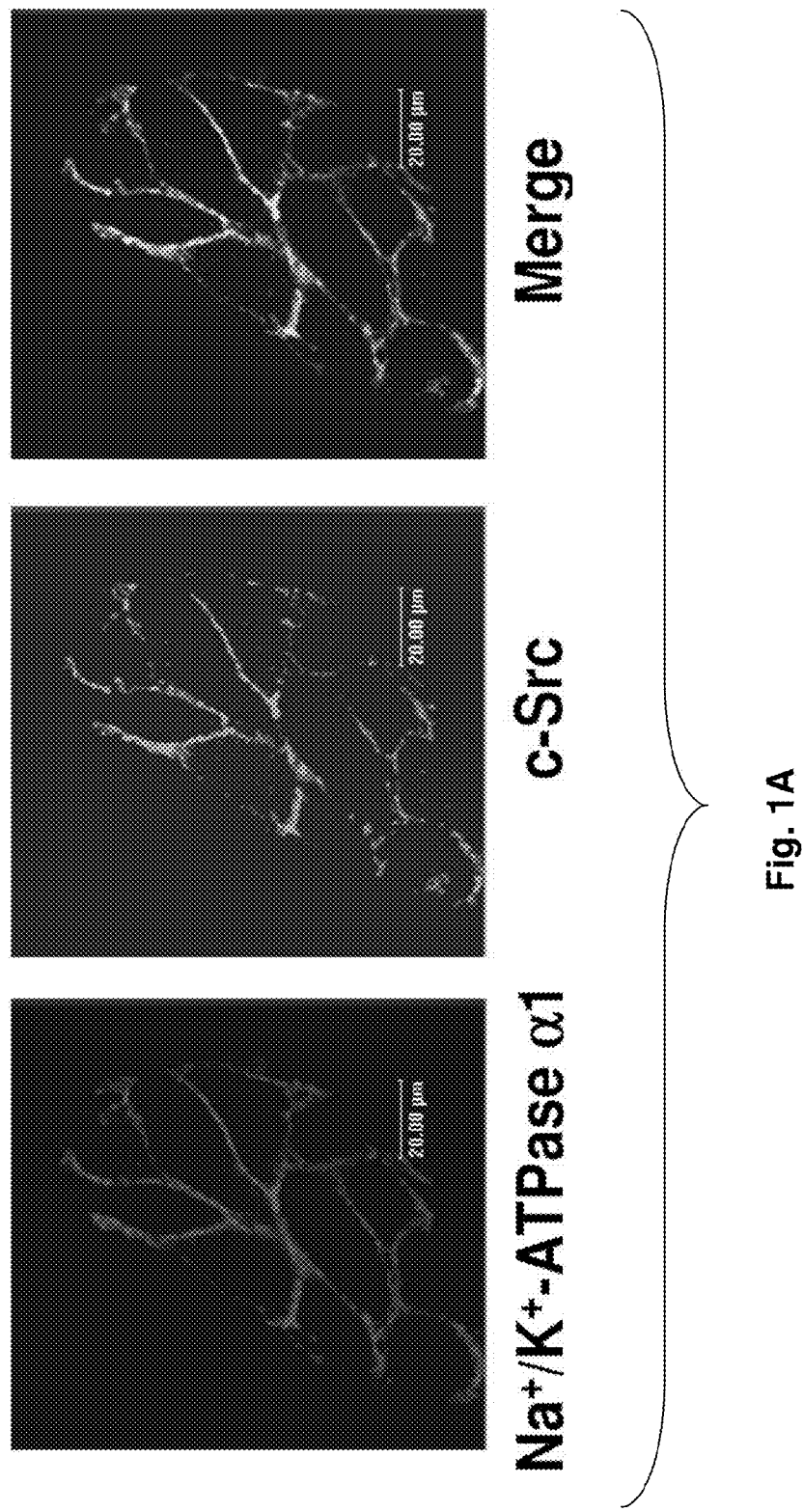

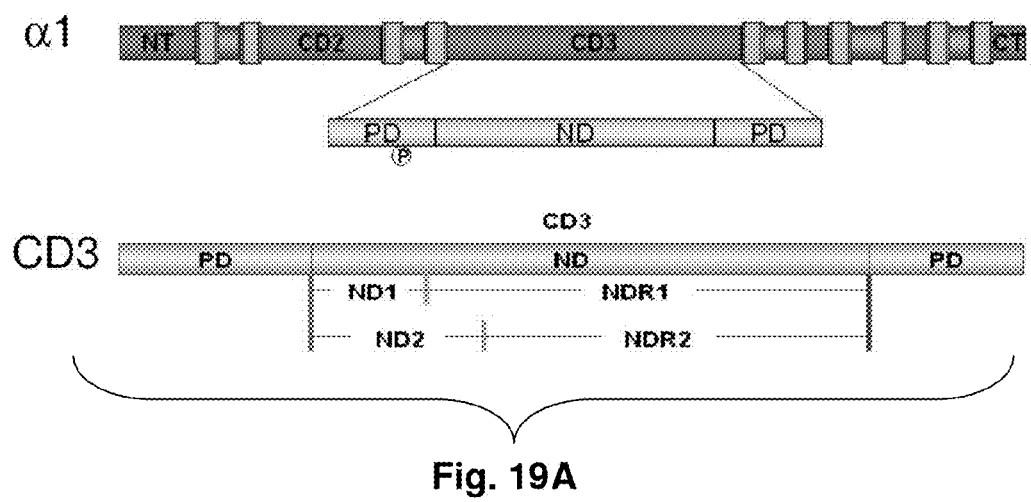
Fig. 19A
ND1 sequence:
LTQNRMTVAHMWSDNQIHEADTTENQSGVSFDKTSATWLALSRIAGLCNRAVFQANQ
Fig. 19B
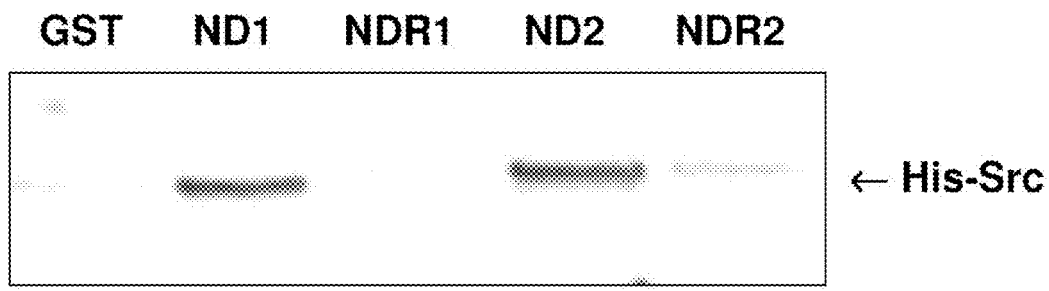
Fig. 19C

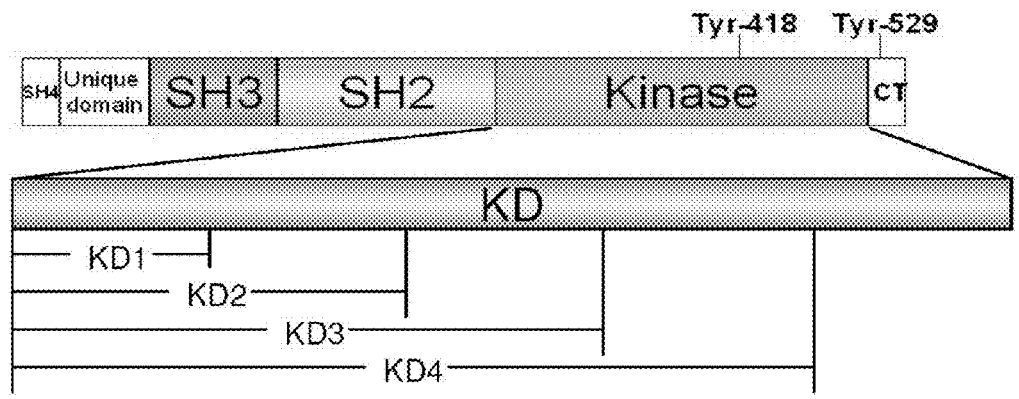
Fig. 20A
B KD1 sequence
LRLEVKLGQGCFGEVWMGTWNGTTRVAIKTLKPGTMSPEAFLQEAQVMKKLRHE
Fig. 20B
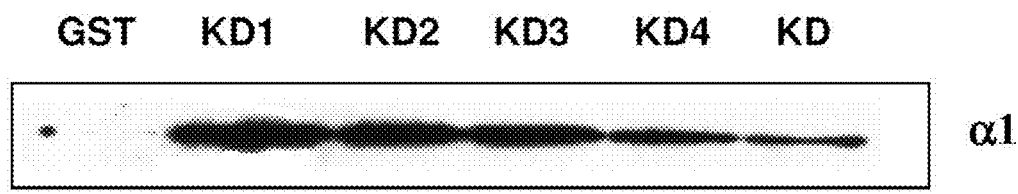
Fig. 20C

TABLE 1

Targets and oligo sequences of human Na/K ATPase-α1 subunit-specific siRNAs

The target sequences are marked by bold letters.

| siRNA | Target sequence | Oligo inserts |
|---|---|---|
| A1 | 467 agatcatgaatccttcaa | sense, 5'-tcgagagatcatgaatccttcaattcaagagattgaaggattccatgatctttttt-3';<br>anti-sense, 5'-ctagaaaaaagatcatggaatccttcaatctcttgaattgaaggattccatgatctc-3' |
| A2 | 1449 ctccaccaacaagtaccag | sense, 5'-tcgagctccaccaacaagtaccagttcaagagactggtacttgttggtggagtttttt-3';<br>anti-sense, 5'-ctagaaaaaactccaccaacaagtaccagtctcttgaactggtacttgttggtggagc-3' |
| A3 | 1896 ggtcatcatggtcacagga | sense, 5'-tcgagggtcatcatggtcacaggattcaagagatcctgtgaccatgatgacctttttt-3';<br>anti-sense, 5'-ctagaaaaaaggtcatcatggtcacaggatctcttgaatcctgtgaccatgatgaccc-3' |
| A4 | 2793 ggtcgtctgatctttgata | sense, 5'-tcgagggtcgtctgatctttgatattcaagagatatcaaagatcagacgaccttttt-3';<br>anti-sense, 5'-ctagaaaaaaggtcgtctgatctttgatatctcttgatatcaaagatcagacgaccc-3' |

Fig. 25

TABLE 2

Relative α1 subunit protein content and the composition of DNA constructs used in different cell lines

| Cell lines | Relative α1 content (mean ± S.E.) | DNA constructs used in transfection |
|---|---|---|
| P-11 | * | pSuppressor, pBade-puro |
| A1 | 100 | pSuppressor, pBade-puro |
| A4-11 | 97.4 ± 2.1 | pSuppressor-A1 siRNA, pBade-puro |
| TCN23-19 | 44.1 ± 2.3 | pSuppressor-A4 siRNA, pBade-puro |
| PY-17 | 12.0 ± 4 | pSuppressor-A4 siRNA, pBade-puro |
| PY-17-AAC-M1-19 (AAC-19) | 7.5 ± 3.0 | pSuppressor-A4 siRNA, pBade-puro, pEYFP |
|  | 93.7 ± 9.9 | pSuppressor-A4 siRNA, pBade-puro, pEYFP, pRc/CMV-α1AACm1 (rat α1) |

Fig. 26

TABLE 3
Na/K-ATPase activity in different cell lines

| Cell line | Activity |
|---|---|
| | % |
| P-11 | 100 |
| PY-17 | 20.8 ± 3.7 |
| AAC-19 | 92.2 ± 6.4 |

Fig. 27

TAT (13AA):      GRKKR RQRRR PPQ
AP (16AA):       RQIKIWFQNR RMKWKK

Fig. 28

TAT_P3: GRKKRRQRRRPPQSATWLALSRIAGLCNRAVFQ
AP_P3:  RQIKIWFQNRRMKWKKSATWLALSRIAGLCNRAVFQ

Fig. 29A

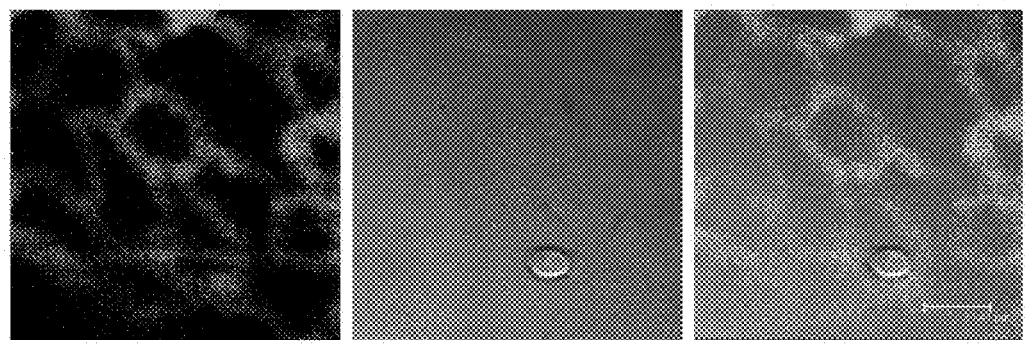

FITC-TAT-P3 mainly distributed near the plasma membrane of DU-145. DU-145 cells were exposed to 1μM FITC-TAT-P3 for 30min, then checked with fluorescence microscopy.

Fig. 29C

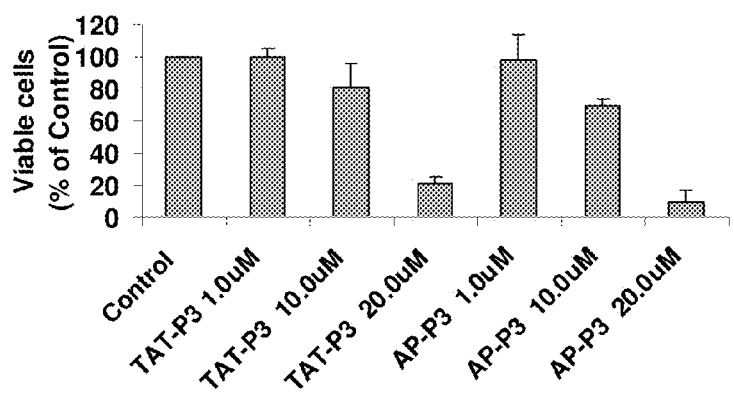

Cell toxicity of CPP conjugated P3 peptides. DU145 cells were plated at $1\times10^5$ cells per well in 12-well tissue culture plates over night, then exposed to TAT-P3 or AP-P3 with indicated concentrations for 24 hr. Viable cells were counted by Trypan blue staining. n=2

Fig. 29D

| SEQ ID | Swiss Prot Access No. | Name | Sequence |
|---|---|---|---|
| 1 | | ND1/CANFA | LTQNRMTVAHMWSDNQIHEADTTENQSGVSFDKTSATWLALSRI AGLCNRAVFQANQ |
| 2 | P50997 | P3/CANFA | SATWLALSRIAGLCNRAVFQ |
| 3 | P05023 | P3/HUMAN | SATWLALSRIAGLCNRAVFQ |
| 4 | P05024 | P3/PIG | SATWLALSRIAGLCNRAVFQ |
| 5 | P04074 | P3/SHEEP | SATWLALSRIAGLCNRAVFQ |
| 6 | P06685 | P3/RAT | SATWFALSRIAGLCNRAVFQ |
| 7 | P09572 | P3/CHICK | SATWLALSRIAGLCNRAVFQ |
| 8 | P30714 | P3/BUFMA | SPTWTALARIAGLCNRAVFP |
| 9 | Q92123 | P3/XENLA | SPTWTALSRVAGLCNRAVFQ |
| 10 | Q92030 | P3/ANGAN | SATWAALARIAGLCNRAVFL |
| 11 | P25489 | P3/CATCO | SDTWASLARIAGLCNRAVFL |
| 12 | P05025 | P3/TORCA | SLSWNALSRIAALCNRAVFQ |
| 13 | AAF98360 | P3/DANIO | SPTWAALARVAGLCNRAVFR |
| 14 | P50993 | P3/HUMAN | SPTWTALSRIAGLCNRAVFK |
| 15 | P06686 | P3/RAT | SPTWTALSRIAGLCNRAVFK |
| 16 | P24797 | P3/CHICK | SPTWAALSRIAGLCNRAVFK |
| 17 | P13637 | P3/HUMAN | SHTWVALSHIAGLCNRAVFK |
| 18 | P06687 | P3/RAT | SHTWVALSHIAGLCNRAVFK |
| 19 | P24798 | P3/CHICK | SATWVALSHIAGLCNRAVFK |
| 20 | Q64541 | P3/RAT | SDTWFYLARIAGLCNRADFK |
| 21 | Q13733 | P3/HUMAN | SDTWFMLARIAGLCNRADFK |
| 22 | AAD43813 | P3/MUS | SDTWFYLARIAGLCNRADFK |
| 23 | O76154 | P3/DUGJA | SDTWKMLARISMLCNRAQFK |
| 24 | P13607 | P3/DROME | SPGFKALSRIATLCNRAEFK |
| 25 | Q27766 | P3/CTEFE | SPGFKALARIATLCNRAEFK |
| 26 | P28744 | P3/ARTSF | SAGWKALVKIAALCSRAEFK |
| 27 | P17326 | P3/ARTSF | SKGFPELIRVASLCSRAEFK |
| 28 | P35317 | P3/HYDAT | SLTWKSLAKVAALCSRAEFK |
| 29 | Q27461 | P3/CAFEL | GASFEALVRIASLCNRAEFK |
| 30 | O45240 | P3/CAFEL | KEDSYQKLLRCATLCSRSHFRV |
| 31 | Q95024 | P3/DICDI | TPTCAALLNVGACCNRADFDRLEG |
| 32 | P09626 | P3/RAT | SETWRALCRVLTLCNRAAFK |
| 33 | Q64578 | P3/RAT | STYADGLVELATICALCNDSSLDFN |
| 34 | | KD1/CANFA | LRLEVKLGQGCFGEVWMGTWNGTTRVAIKTLKPGTMSPEAFLQ EAQVMKKLRHE |
| 35 | | A1/DNA | agatcatggaatccttcaa |
| 36 | | A2/DNA | ctccaccaacaagtaccag |
| 37 | | A3/DNA | ggtcatcatggtcacagga |
| 38 | | A4/DNA | ggtcgtctgatctttgata |
| 39 | | A1 sense/DNA | 5'-tcgagagatcatggaatccttcaattcaagagattgaaggattccatgatcttttt-3' |
| 40 | | A1 anti-sense/DNA | 5'-ctagaaaaagatcatggaatccttcatctcttgaattgaaggattccatgatctc-3' |
| 41 | | A2 sense/DNA | 5'-tcgagctccaccaacaagtaccagttcaagagactggtacttgttggtggagttttt-3' |
| 42 | | A2 anti-sense/DNA | 5'-ctagaaaaactccaccaacaagtaccagtctcttgaactggtacttgttggtggagc-3' |
| 43 | | A3 sense/DNA | 5'-tcgagggtcatcatggtcacaggattcaagagatcctgtgaccatgatgacctttt-3' |

Fig. 30A

| 44 | | A3 anti-sense/DNA | 5'-ctagaaaaaggtcatcatggtcacaggatctcttgaatcctgtgaccatgatgaccc-3' |
|---|---|---|---|
| 45 | | A4 sense/DNA | 5'-tcgagggtcgtctgatctttgatattcaagagatatcaaagatcagacgaccttttt-3' |
| 46 | | A4 anti-sense/DNA | 5'-ctagaaaaaggtcgtctgatctttgatatctcttgaatatcaaagatcagacgaccc-3' |
| 47 | | TAT | GRKKR RQRRR PPQ |
| 48 | | AP | RQIKIWFQNR RMKWKK |
| 49 | | TAT-P3 | GRKKRRQRRRPPQSATWLALSRIAGLCNRAVFQ |
| 50 | | AP-P3 | RQIKIWFQNRRMKWKKSATWLALSRIAGLCNRAVFQ |
| 51 | P05024 | NT (6-90)/PIG | MGKGVGRDKY EPAAVSEHGD KKKAKKERDM DELKKEVSMD DHKLSLDELH RKYGTDLSRG LTPARAAEIL ARDGPNALTP PPTTPEWVKF |
| 52 | P05024 | CD2 (152-288)/PIG | SSKIMESFKNMVPQQALVIRNGEKMSINAEEVVVGDLVEVKGGDRIP ADLRIISANGCKVDNSSLTGESEPQTRSPDFTNENPLETRNIAFFSTNC VEGTARGIVVYTGDRTVMGRIATLASGLEGGQTPIAAEIEH |
| 53 | P05024 | CD3 (350-784)/PIG | A RKNCLVKNLE AVETLGSTST ICSDKTGTLT QNRMTVAHMW SDNQIHEADT TENQSGVSFD KTSATWLALS RIAGLCNRAV FQANQENLPI LKRAVAGDAS ESALLKCIEL CCGSVKEMRE RYTKIVEIPF NSTNKYQLSI HKNPNTAEPR HLLVMKGAPE RILDRCSSIL IHGKEQPLDE ELKDAFQNAY LELGGLGERV LGFCHLFLPD EQFPEGFQFD TDDVNFPLDN LCFVGLISMI DPPRAAVPDA VGKCRSAGIK VIMVTGDHPI TAKAIAKGVG IISEGNETVE DIAARLNIPV SQVNPRDAKA CVVHGSDLKD MTSEQLDDIL KYHTEIVFAR TSPQQKLIIV EGCQRQGAIV AVTGDGVNDS PASKKADIGV AMGIAGSDVS KQAADMILLD DNFASIVTGV EEGRLIFDNL KKSIAYTLTS NIPE |
| 54 | | H/K ATPase CD3 (348-778) | TVT VCLSLTAKRL ASKNCVVKNL EAVETLGSTS VICSDKTGTL TQNRMTVSHL WFDNHIHTAD TTEDQSGQTF DQSSETWRAL CRVLTLCNRA AFKSGQDAVP VPKRIVIGDA SETALLKFSE LTLGNAMGYR DRFPKVCEIP FNSTNKFQLS IHTLEDPRDP RHLLVMKGAP ERVLERCSSI LIKGQELPLD EQWREAFQTA YLSLGGLGER VLGFCQLYLN EKDYPPGYTF DVEAMNFPSS GLCFAGLVSM IDPPRATVPD AVLKCRTAGI RVIMVTGDHP ITAKAIAASV GIISEGSETV EDIAARLRMP VDQVNKKDAR ACVINGMQLK DMDPSELVEA LRTHPEMVFA RTSPQQKLVI VESCQRLGAI VAVTGDGVND SPALKKADIG VAMGIAGSDA AKNAADMILL DDNFASIVTG VEQGRLIF |
| 55 | | SERCA2-CD3 (322-768) | GTRRMAKKN AIVRSLPSVE TLGCTSVICS DKTGTLTTNQ MSVCRMFILD KVEGDTCSLN EFTITGSTYA PIGEVQKDDK PVKCHQYDGL VELATICALC NDSALDYNEA KGVYEKVGEA TETALTCLVE KMNVFDTELK GLSKIERANA CNSVIKQLMK KEFTLEFSRD RKSMSVYCTP NKPSRTSMSK MFVKGAPEGV IDRCTHIRVG STKVPMTPGV KQKIMSVIRE WGSGSDTLRC LALATHDNPL RREEMHLEDS ANFIKYETNL TFVGCVGMLD PPRIEVASSV KLCRQAGIRV IMITGDNKGT AVAICRRIGI FGQDEDVTSK AFTGREFDEL SPSAQRDACL NARCFARVEP SHKSKIVEFL QSFDEITAMT GDGVNDAPAL KKSEIGIAMG SGTAVAKTAS EMVLADDNFS TIVAAVEEGR AIYNNMKQFI RYLISSNV |

Fig. 30B

SEQUENCE LISTING

```
<160> NUMBER OF SEQ ID NOS: 55

<210> SEQ ID NO 1
<211> LENGTH: 57
<212> TYPE: PRT
<213> ORGANISM: Canis familiaris

<400> SEQUENCE: 1

Leu Thr Gln Asn Arg Met Thr Val Ala His Met Trp Ser Asp Asn Gln
1               5                   10                  15

Ile His Glu Ala Asp Thr Thr Glu Asn Gln Ser Gly Val Ser Phe Asp
            20                  25                  30

Lys Thr Ser Ala Thr Trp Leu Ala Leu Ser Arg Ile Ala Gly Leu Cys
        35                  40                  45

Asn Arg Ala Val Phe Gln Ala Asn Gln
    50                  55

<210> SEQ ID NO 2
<211> LENGTH: 20
<212> TYPE: PRT
<213> ORGANISM: Canis familiaris

<400> SEQUENCE: 2

Ser Ala Thr Trp Leu Ala Leu Ser Arg Ile Ala Gly Leu Cys Asn Arg
1               5                   10                  15

Ala Val Phe Gln
            20

<210> SEQ ID NO 3
<211> LENGTH: 20
<212> TYPE: PRT
<213> ORGANISM: Homo sapiens

<400> SEQUENCE: 3

Ser Ala Thr Trp Leu Ala Leu Ser Arg Ile Ala Gly Leu Cys Asn Arg
1               5                   10                  15

Ala Val Phe Gln
            20

<210> SEQ ID NO 4
<211> LENGTH: 20
<212> TYPE: PRT
<213> ORGANISM: Sus scrofa

<400> SEQUENCE: 4

Ser Ala Thr Trp Leu Ala Leu Ser Arg Ile Ala Gly Leu Cys Asn Arg
1               5                   10                  15

Ala Val Phe Gln
            20

<210> SEQ ID NO 5
<211> LENGTH: 20
<212> TYPE: PRT
<213> ORGANISM: Ovis aries

<400> SEQUENCE: 5

Ser Ala Thr Trp Leu Ala Leu Ser Arg Ile Ala Gly Leu Cys Asn Arg
1               5                   10                  15

Ala Val Phe Gln
            20
```

```
<210> SEQ ID NO 6
<211> LENGTH: 20
<212> TYPE: PRT
<213> ORGANISM: Rattus norvegicus

<400> SEQUENCE: 6

Ser Ala Thr Trp Phe Ala Leu Ser Arg Ile Ala Gly Leu Cys Asn Arg
1               5                   10                  15

Ala Val Phe Gln
            20

<210> SEQ ID NO 7
<211> LENGTH: 20
<212> TYPE: PRT
<213> ORGANISM: Gallus gallus

<400> SEQUENCE: 7

Ser Ala Thr Trp Leu Ala Leu Ser Arg Ile Ala Gly Leu Cys Asn Arg
1               5                   10                  15

Ala Val Phe Gln
            20

<210> SEQ ID NO 8
<211> LENGTH: 20
<212> TYPE: PRT
<213> ORGANISM: Bufo marinus

<400> SEQUENCE: 8

Ser Pro Thr Trp Thr Ala Leu Ala Arg Ile Ala Gly Leu Cys Asn Arg
1               5                   10                  15

Ala Val Phe Pro
            20

<210> SEQ ID NO 9
<211> LENGTH: 20
<212> TYPE: PRT
<213> ORGANISM: Xenopus laevis

<400> SEQUENCE: 9

Ser Pro Thr Trp Thr Ala Leu Ser Arg Val Ala Gly Leu Cys Asn Arg
1               5                   10                  15

Ala Val Phe Gln
            20

<210> SEQ ID NO 10
<211> LENGTH: 20
<212> TYPE: PRT
<213> ORGANISM: Anguilla anguilla

<400> SEQUENCE: 10

Ser Ala Thr Trp Ala Ala Leu Ala Arg Ile Ala Gly Leu Cys Asn Arg
1               5                   10                  15

Ala Val Phe Leu
            20

<210> SEQ ID NO 11
<211> LENGTH: 20
<212> TYPE: PRT
<213> ORGANISM: Catostomus commersonii

<400> SEQUENCE: 11

Ser Asp Thr Trp Ala Ser Leu Ala Arg Ile Ala Gly Leu Cys Asn Arg
1               5                   10                  15
```

Ala Val Phe Leu
            20

<210> SEQ ID NO 12
<211> LENGTH: 20
<212> TYPE: PRT
<213> ORGANISM: Torpedo californica

<400> SEQUENCE: 12

Ser Leu Ser Trp Asn Ala Leu Ser Arg Ile Ala Ala Leu Cys Asn Arg
1               5                   10                  15

Ala Val Phe Gln
            20

<210> SEQ ID NO 13
<211> LENGTH: 20
<212> TYPE: PRT
<213> ORGANISM: Danio rerio

<400> SEQUENCE: 13

Ser Pro Thr Trp Ala Ala Leu Ala Arg Val Ala Gly Leu Cys Asn Arg
1               5                   10                  15

Ala Val Phe Arg
            20

<210> SEQ ID NO 14
<211> LENGTH: 20
<212> TYPE: PRT
<213> ORGANISM: Homo sapiens

<400> SEQUENCE: 14

Ser Pro Thr Trp Thr Ala Leu Ser Arg Ile Ala Gly Leu Cys Asn Arg
1               5                   10                  15

Ala Val Phe Lys
            20

<210> SEQ ID NO 15
<211> LENGTH: 20
<212> TYPE: PRT
<213> ORGANISM: Rattus norvegicus

<400> SEQUENCE: 15

Ser Pro Thr Trp Thr Ala Leu Ser Arg Ile Ala Gly Leu Cys Asn Arg
1               5                   10                  15

Ala Val Phe Lys
            20

<210> SEQ ID NO 16
<211> LENGTH: 20
<212> TYPE: PRT
<213> ORGANISM: Gallus gallus

<400> SEQUENCE: 16

Ser Pro Thr Trp Ala Ala Leu Ser Arg Ile Ala Gly Leu Cys Asn Arg
1               5                   10                  15

Ala Val Phe Lys
            20

<210> SEQ ID NO 17
<211> LENGTH: 20
<212> TYPE: PRT
<213> ORGANISM: Homo sapiens

<400> SEQUENCE: 17

Ser His Thr Trp Val Ala Leu Ser His Ile Ala Gly Leu Cys Asn Arg
1               5                   10                  15

Ala Val Phe Lys
            20

<210> SEQ ID NO 18
<211> LENGTH: 20
<212> TYPE: PRT
<213> ORGANISM: Rattus norvegicus

<400> SEQUENCE: 18

Ser His Thr Trp Val Ala Leu Ser His Ile Ala Gly Leu Cys Asn Arg
1               5                   10                  15

Ala Val Phe Lys
            20

<210> SEQ ID NO 19
<211> LENGTH: 20
<212> TYPE: PRT
<213> ORGANISM: Gallus gallus

<400> SEQUENCE: 19

Ser Ala Thr Trp Val Ala Leu Ser His Ile Ala Gly Leu Cys Asn Arg
1               5                   10                  15

Ala Val Phe Lys
            20

<210> SEQ ID NO 20
<211> LENGTH: 20
<212> TYPE: PRT
<213> ORGANISM: Rattus norvegicus

<400> SEQUENCE: 20

Ser Asp Thr Trp Phe Tyr Leu Ala Arg Ile Ala Gly Leu Cys Asn Arg
1               5                   10                  15

Ala Asp Phe Lys
            20

<210> SEQ ID NO 21
<211> LENGTH: 20
<212> TYPE: PRT
<213> ORGANISM: Homo sapiens

<400> SEQUENCE: 21

Ser Asp Thr Trp Phe Met Leu Ala Arg Ile Ala Gly Leu Cys Asn Arg
1               5                   10                  15

Ala Asp Phe Lys
            20

<210> SEQ ID NO 22
<211> LENGTH: 20
<212> TYPE: PRT
<213> ORGANISM: Mus musculus

<400> SEQUENCE: 22

Ser Asp Thr Trp Phe Tyr Leu Ala Arg Ile Ala Gly Leu Cys Asn Arg
1               5                   10                  15

Ala Asp Phe Lys
            20

```
<210> SEQ ID NO 23
<211> LENGTH: 20
<212> TYPE: PRT
<213> ORGANISM: Dugesia japonica

<400> SEQUENCE: 23

Ser Asp Thr Trp Lys Met Leu Ala Arg Ile Ser Met Leu Cys Asn Arg
1               5                   10                  15

Ala Gln Phe Lys
            20

<210> SEQ ID NO 24
<211> LENGTH: 20
<212> TYPE: PRT
<213> ORGANISM: Drosophila melanogaster

<400> SEQUENCE: 24

Ser Pro Gly Phe Lys Ala Leu Ser Arg Ile Ala Thr Leu Cys Asn Arg
1               5                   10                  15

Ala Glu Phe Lys
            20

<210> SEQ ID NO 25
<211> LENGTH: 20
<212> TYPE: PRT
<213> ORGANISM: Ctenocephalides felis

<400> SEQUENCE: 25

Ser Pro Gly Phe Lys Ala Leu Ala Arg Ile Ala Thr Leu Cys Asn Arg
1               5                   10                  15

Ala Glu Phe Lys
            20

<210> SEQ ID NO 26
<211> LENGTH: 20
<212> TYPE: PRT
<213> ORGANISM: Ambrosia artemisiifolia

<400> SEQUENCE: 26

Ser Ala Gly Trp Lys Ala Leu Val Lys Ile Ala Ala Leu Cys Ser Arg
1               5                   10                  15

Ala Glu Phe Lys
            20

<210> SEQ ID NO 27
<211> LENGTH: 20
<212> TYPE: PRT
<213> ORGANISM: Ambrosia artemisiifolia

<400> SEQUENCE: 27

Ser Lys Gly Phe Pro Glu Leu Ile Arg Val Ala Ser Leu Cys Ser Arg
1               5                   10                  15

Ala Glu Phe Lys
            20

<210> SEQ ID NO 28
<211> LENGTH: 20
<212> TYPE: PRT
<213> ORGANISM: Hydra attenuata

<400> SEQUENCE: 28

Ser Leu Thr Trp Lys Ser Leu Ala Lys Val Ala Ala Leu Cys Ser Arg
```

```
1               5                    10                   15

Ala Glu Phe Lys
            20

<210> SEQ ID NO 29
<211> LENGTH: 20
<212> TYPE: PRT
<213> ORGANISM: Caenorhabditis elegans

<400> SEQUENCE: 29

Gly Ala Ser Phe Glu Ala Leu Val Arg Ile Ala Ser Leu Cys Asn Arg
1               5                   10                  15

Ala Glu Phe Lys
            20

<210> SEQ ID NO 30
<211> LENGTH: 22
<212> TYPE: PRT
<213> ORGANISM: Caenorhabditis elegans

<400> SEQUENCE: 30

Lys Glu Asp Ser Tyr Gln Lys Leu Leu Arg Cys Ala Thr Leu Cys Ser
1               5                   10                  15

Arg Ser His Phe Arg Val
            20

<210> SEQ ID NO 31
<211> LENGTH: 24
<212> TYPE: PRT
<213> ORGANISM: Dictyostelium discoideum

<400> SEQUENCE: 31

Thr Pro Thr Cys Ala Ala Leu Leu Asn Val Gly Ala Cys Cys Asn Arg
1               5                   10                  15

Ala Asp Phe Asp Arg Leu Glu Gly
            20

<210> SEQ ID NO 32
<211> LENGTH: 20
<212> TYPE: PRT
<213> ORGANISM: Rattus norvegicus

<400> SEQUENCE: 32

Ser Glu Thr Trp Arg Ala Leu Cys Arg Val Leu Thr Leu Cys Asn Arg
1               5                   10                  15

Ala Ala Phe Lys
            20

<210> SEQ ID NO 33
<211> LENGTH: 25
<212> TYPE: PRT
<213> ORGANISM: Rattus norvegicus

<400> SEQUENCE: 33

Ser Thr Tyr Ala Asp Gly Leu Val Glu Leu Ala Thr Ile Cys Ala Leu
1               5                   10                  15

Cys Asn Asp Ser Ser Leu Asp Phe Asn
            20                  25

<210> SEQ ID NO 34
<211> LENGTH: 54
<212> TYPE: PRT
```

<213> ORGANISM: Canis familiaris

<400> SEQUENCE: 34

Leu Arg Leu Glu Val Lys Leu Gly Gln Gly Cys Phe Gly Glu Val Trp
1               5                   10                  15

Met Gly Thr Trp Asn Gly Thr Thr Arg Val Ala Ile Lys Thr Leu Lys
            20                  25                  30

Pro Gly Thr Met Ser Pro Glu Ala Phe Leu Gln Glu Ala Gln Val Met
        35                  40                  45

Lys Lys Leu Arg His Glu
    50

<210> SEQ ID NO 35
<211> LENGTH: 19
<212> TYPE: DNA
<213> ORGANISM: Homo sapiens

<400> SEQUENCE: 35
agatcatgga atccttcaa                                              19

<210> SEQ ID NO 36
<211> LENGTH: 19
<212> TYPE: DNA
<213> ORGANISM: Homo sapiens

<400> SEQUENCE: 36
ctccaccaac aagtaccag                                              19

<210> SEQ ID NO 37
<211> LENGTH: 19
<212> TYPE: DNA
<213> ORGANISM: Homo sapiens

<400> SEQUENCE: 37
ggtcatcatg gtcacagga                                              19

<210> SEQ ID NO 38
<211> LENGTH: 19
<212> TYPE: DNA
<213> ORGANISM: Homo sapiens

<400> SEQUENCE: 38
ggtcgtctga tctttgata                                              19

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tcgagagatc atggaatcct tcaattcaag agattgaagg attccatgat ctttttt    57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctagaaaaaa gatcatggaa tccttcaatc tcttgaattg aaggattcca tgatctc       57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcgagctcca ccaacaagta ccagttcaag agactggtac ttgttggtgg agttttt       57

<210> SEQ ID NO 42
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctagaaaaac tccaccaaca agtaccagtc tcttgaactg gtacttgttg gtggagc       57

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcgagggtca tcatggtcac aggattcaag agatcctgtg accatgatga ccttttt       57

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctagaaaaag gtcatcatgg tcacaggatc tcttgaatcc tgtgaccatg atgaccc       57

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcgagggtcg tctgatcttt gatattcaag agatatcaaa gatcagacga ccttttt       57

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
ctagaaaaag gtcgtctgat ctttgatatc tcttgaatat caaagatcag acgaccc        57
```

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Arg Lys Lys Arg Arg Gln Arg Arg Arg Pro Pro Gln
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Gln Ile Lys Ile Trp Phe Gln Asn Arg Arg Met Lys Trp Lys Lys
1               5                   10                  15

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Lys Lys Arg Arg Gln Arg Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Gln Ile Lys Ile Trp Phe Gln Asn Arg Arg Met Lys Trp Lys Lys
1               5                   10                  15

Ser Ala Thr Trp Leu Ala Leu Ser Arg Ile Ala Gly Leu Cys Asn Arg
            20                  25                  30

Ala Val Phe Gln
        35

<210> SEQ ID NO 51
<211> LENGTH: 90
<212> TYPE: PRT
<213> ORGANISM: Sus scrofa

<400> SEQUENCE: 51

Met Gly Lys Gly Val Gly Arg Asp Lys Tyr Glu Pro Ala Ala Val Ser
1               5                   10                  15

```
Glu His Gly Asp Lys Lys Ala Lys Lys Glu Arg Asp Met Asp Glu
            20                  25                  30

Leu Lys Lys Glu Val Ser Met Asp Asp His Lys Leu Ser Leu Asp Glu
         35                  40                  45

Leu His Arg Lys Tyr Gly Thr Asp Leu Ser Arg Gly Leu Thr Pro Ala
 50                  55                  60

Arg Ala Ala Glu Ile Leu Ala Arg Asp Gly Pro Asn Ala Leu Thr Pro
65                  70                  75                  80

Pro Pro Thr Thr Pro Glu Trp Val Lys Phe
                 85                  90
```

<210> SEQ ID NO 52
<211> LENGTH: 137
<212> TYPE: PRT
<213> ORGANISM: Sus scrofa

<400> SEQUENCE: 52

```
Ser Ser Lys Ile Met Glu Ser Phe Lys Asn Met Val Pro Gln Gln Ala
1               5                   10                  15

Leu Val Ile Arg Asn Gly Glu Lys Met Ser Ile Asn Ala Glu Glu Val
            20                  25                  30

Val Val Gly Asp Leu Val Glu Val Lys Gly Gly Asp Arg Ile Pro Ala
         35                  40                  45

Asp Leu Arg Ile Ile Ser Ala Asn Gly Cys Lys Val Asp Asn Ser Ser
 50                  55                  60

Leu Thr Gly Glu Ser Glu Pro Gln Thr Arg Ser Pro Asp Phe Thr Asn
65                  70                  75                  80

Glu Asn Pro Leu Glu Thr Arg Asn Ile Ala Phe Phe Ser Thr Asn Cys
                85                  90                  95

Val Glu Gly Thr Ala Arg Gly Ile Val Val Tyr Thr Gly Asp Arg Thr
                100                 105                 110

Val Met Gly Arg Ile Ala Thr Leu Ala Ser Gly Leu Glu Gly Gly Gln
            115                 120                 125

Thr Pro Ile Ala Ala Glu Ile Glu His
        130                 135
```

<210> SEQ ID NO 53
<211> LENGTH: 435
<212> TYPE: PRT
<213> ORGANISM: Sus scrofa

<400> SEQUENCE: 53

```
Ala Arg Lys Asn Cys Leu Val Lys Asn Leu Glu Ala Val Glu Thr Leu
1               5                   10                  15

Gly Ser Thr Ser Thr Ile Cys Ser Asp Lys Thr Gly Thr Leu Thr Gln
            20                  25                  30

Asn Arg Met Thr Val Ala His Met Trp Ser Asp Asn Gln Ile His Glu
         35                  40                  45

Ala Asp Thr Thr Glu Asn Gln Ser Gly Val Ser Phe Asp Lys Thr Ser
 50                  55                  60

Ala Thr Trp Leu Ala Leu Ser Arg Ile Ala Gly Leu Cys Asn Arg Ala
65                  70                  75                  80

Val Phe Gln Ala Asn Gln Glu Asn Leu Pro Ile Leu Lys Arg Ala Val
                85                  90                  95

Ala Gly Asp Ala Ser Glu Ser Ala Leu Leu Lys Cys Ile Glu Leu Cys
                100                 105                 110
```

```
Cys Gly Ser Val Lys Glu Met Arg Glu Arg Tyr Thr Lys Ile Val Glu
        115                 120                 125

Ile Pro Phe Asn Ser Thr Asn Lys Tyr Gln Leu Ser Ile His Lys Asn
        130                 135                 140

Pro Asn Thr Ala Glu Pro Arg His Leu Val Met Lys Gly Ala Pro
145                 150                 155                 160

Glu Arg Ile Leu Asp Arg Cys Ser Ser Ile Leu Ile His Gly Lys Glu
                165                 170                 175

Gln Pro Leu Asp Glu Glu Leu Lys Asp Ala Phe Gln Asn Ala Tyr Leu
            180                 185                 190

Glu Leu Gly Gly Leu Gly Glu Arg Val Leu Gly Phe Cys His Leu Phe
        195                 200                 205

Leu Pro Asp Glu Gln Phe Pro Glu Gly Phe Gln Phe Asp Thr Asp Asp
    210                 215                 220

Val Asn Phe Pro Leu Asp Asn Leu Cys Phe Val Gly Leu Ile Ser Met
225                 230                 235                 240

Ile Asp Pro Pro Arg Ala Ala Val Pro Asp Ala Val Gly Lys Cys Arg
                245                 250                 255

Ser Ala Gly Ile Lys Val Ile Met Val Thr Gly Asp His Pro Ile Thr
            260                 265                 270

Ala Lys Ala Ile Ala Lys Gly Val Gly Ile Ile Ser Glu Gly Asn Glu
        275                 280                 285

Thr Val Glu Asp Ile Ala Ala Arg Leu Asn Ile Pro Val Ser Gln Val
    290                 295                 300

Asn Pro Arg Asp Ala Lys Ala Cys Val Val His Gly Ser Asp Leu Lys
305                 310                 315                 320

Asp Met Thr Ser Glu Gln Leu Asp Asp Ile Leu Lys Tyr His Thr Glu
                325                 330                 335

Ile Val Phe Ala Arg Thr Ser Pro Gln Gln Lys Leu Ile Ile Val Glu
            340                 345                 350

Gly Cys Gln Arg Gln Gly Ala Ile Val Ala Val Thr Gly Asp Gly Val
        355                 360                 365

Asn Asp Ser Pro Ala Ser Lys Lys Ala Asp Ile Gly Val Ala Met Gly
    370                 375                 380

Ile Ala Gly Ser Asp Val Ser Lys Gln Ala Ala Asp Met Ile Leu Leu
385                 390                 395                 400

Asp Asp Asn Phe Ala Ser Ile Val Thr Gly Val Glu Glu Gly Arg Leu
                405                 410                 415

Ile Phe Asp Asn Leu Lys Lys Ser Ile Ala Tyr Thr Leu Thr Ser Asn
            420                 425                 430

Ile Pro Glu
        435

<210> SEQ ID NO 54
<211> LENGTH: 431
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 54

Thr Val Thr Val Cys Leu Ser Leu Thr Ala Lys Arg Leu Ala Ser Lys
1               5                   10                  15

Asn Cys Val Val Lys Asn Leu Glu Ala Val Glu Thr Leu Gly Ser Thr
```

```
                    20                  25                  30
Ser Val Ile Cys Ser Asp Lys Thr Gly Thr Leu Thr Gln Asn Arg Met
                35                  40                  45
Thr Val Ser His Leu Trp Phe Asp Asn His Ile His Thr Ala Asp Thr
            50                  55                  60
Thr Glu Asp Gln Ser Gly Gln Thr Phe Asp Gln Ser Ser Glu Thr Trp
65                  70                  75                  80
Arg Ala Leu Cys Arg Val Leu Thr Leu Cys Asn Arg Ala Ala Phe Lys
                    85                  90                  95
Ser Gly Gln Asp Ala Val Pro Val Pro Lys Arg Ile Val Ile Gly Asp
                100                 105                 110
Ala Ser Glu Thr Ala Leu Leu Lys Phe Ser Glu Leu Thr Leu Gly Asn
                115                 120                 125
Ala Met Gly Tyr Arg Asp Arg Phe Pro Lys Val Cys Glu Ile Pro Phe
            130                 135                 140
Asn Ser Thr Asn Lys Phe Gln Leu Ser Ile His Thr Leu Glu Asp Pro
145                 150                 155                 160
Arg Asp Pro Arg His Leu Leu Val Met Lys Gly Ala Pro Glu Arg Val
                    165                 170                 175
Leu Glu Arg Cys Ser Ser Ile Leu Ile Lys Gly Gln Glu Leu Pro Leu
                180                 185                 190
Asp Glu Gln Trp Arg Glu Ala Phe Gln Thr Ala Tyr Leu Ser Leu Gly
                195                 200                 205
Gly Leu Gly Glu Arg Val Leu Gly Phe Cys Gln Leu Tyr Leu Asn Glu
            210                 215                 220
Lys Asp Tyr Pro Pro Gly Tyr Thr Phe Asp Val Glu Ala Met Asn Phe
225                 230                 235                 240
Pro Ser Ser Gly Leu Cys Phe Ala Gly Leu Val Ser Met Ile Asp Pro
                    245                 250                 255
Pro Arg Ala Thr Val Pro Asp Ala Val Leu Lys Cys Arg Thr Ala Gly
                260                 265                 270
Ile Arg Val Ile Met Val Thr Gly Asp His Pro Ile Thr Ala Lys Ala
                275                 280                 285
Ile Ala Ala Ser Val Gly Ile Ile Ser Glu Gly Ser Glu Thr Val Glu
            290                 295                 300
Asp Ile Ala Ala Arg Leu Arg Met Pro Val Asp Gln Val Asn Lys Lys
305                 310                 315                 320
Asp Ala Arg Ala Cys Val Ile Asn Gly Met Gln Leu Lys Asp Met Asp
                    325                 330                 335
Pro Ser Glu Leu Val Glu Ala Leu Arg Thr His Pro Glu Met Val Phe
                340                 345                 350
Ala Arg Thr Ser Pro Gln Gln Lys Leu Val Ile Val Glu Ser Cys Gln
                355                 360                 365
Arg Leu Gly Ala Ile Val Ala Val Thr Gly Asp Gly Val Asn Asp Ser
            370                 375                 380
Pro Ala Leu Lys Lys Ala Asp Ile Gly Val Ala Met Gly Ile Ala Gly
385                 390                 395                 400
Ser Asp Ala Ala Lys Asn Ala Ala Asp Met Ile Leu Leu Asp Asp Asn
                    405                 410                 415
Phe Ala Ser Ile Val Thr Gly Val Glu Gln Gly Arg Leu Ile Phe
                420                 425                 430

<210> SEQ ID NO 55
```

```
<211> LENGTH: 447
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Gly Thr Arg Arg Met Ala Lys Lys Asn Ala Ile Val Arg Ser Leu Pro
1               5                   10                  15

Ser Val Glu Thr Leu Gly Cys Thr Ser Val Ile Cys Ser Asp Lys Thr
            20                  25                  30

Gly Thr Leu Thr Thr Asn Gln Met Ser Val Cys Arg Met Phe Ile Leu
        35                  40                  45

Asp Lys Val Glu Gly Asp Thr Cys Ser Leu Asn Glu Phe Thr Ile Thr
50                  55                  60

Gly Ser Thr Tyr Ala Pro Ile Gly Glu Val Gln Lys Asp Asp Lys Pro
65                  70                  75                  80

Val Lys Cys His Gln Tyr Asp Gly Leu Val Glu Leu Ala Thr Ile Cys
                85                  90                  95

Ala Leu Cys Asn Asp Ser Ala Leu Asp Tyr Asn Glu Ala Lys Gly Val
            100                 105                 110

Tyr Glu Lys Val Gly Glu Ala Thr Glu Thr Ala Leu Thr Cys Leu Val
        115                 120                 125

Glu Lys Met Asn Val Phe Asp Thr Glu Leu Lys Gly Leu Ser Lys Ile
130                 135                 140

Glu Arg Ala Asn Ala Cys Asn Ser Val Ile Lys Gln Leu Met Lys Lys
145                 150                 155                 160

Glu Phe Thr Leu Glu Phe Ser Arg Asp Arg Lys Ser Met Ser Val Tyr
                165                 170                 175

Cys Thr Pro Asn Lys Pro Ser Arg Thr Ser Met Ser Lys Met Phe Val
            180                 185                 190

Lys Gly Ala Pro Glu Gly Val Ile Asp Arg Cys Thr His Ile Arg Val
        195                 200                 205

Gly Ser Thr Lys Val Pro Met Thr Pro Gly Val Lys Gln Lys Ile Met
210                 215                 220

Ser Val Ile Arg Glu Trp Gly Ser Gly Ser Asp Thr Leu Arg Cys Leu
225                 230                 235                 240

Ala Leu Ala Thr His Asp Asn Pro Leu Arg Arg Glu Glu Met His Leu
                245                 250                 255

Glu Asp Ser Ala Asn Phe Ile Lys Tyr Glu Thr Asn Leu Thr Phe Val
            260                 265                 270

Gly Cys Val Gly Met Leu Asp Pro Pro Arg Ile Glu Val Ala Ser Ser
        275                 280                 285

Val Lys Leu Cys Arg Gln Ala Gly Ile Arg Val Ile Met Ile Thr Gly
290                 295                 300

Asp Asn Lys Gly Thr Ala Val Ala Ile Cys Arg Arg Ile Gly Ile Phe
305                 310                 315                 320

Gly Gln Asp Glu Asp Val Thr Ser Lys Ala Phe Thr Gly Arg Glu Phe
                325                 330                 335

Asp Glu Leu Ser Pro Ser Ala Gln Arg Asp Ala Cys Leu Asn Ala Arg
            340                 345                 350

Cys Phe Ala Arg Val Glu Pro Ser His Lys Ser Lys Ile Val Glu Phe
        355                 360                 365

Leu Gln Ser Phe Asp Glu Ile Thr Ala Met Thr Gly Asp Gly Val Asn
```

-continued

```
            370                 375                 380
Asp Ala Pro Ala Leu Lys Lys Ser Glu Ile Gly Ile Ala Met Gly Ser
385                 390                 395                 400

Gly Thr Ala Val Ala Lys Thr Ala Ser Glu Met Val Leu Ala Asp Asp
                405                 410                 415

Asn Phe Ser Thr Ile Val Ala Ala Val Glu Glu Gly Arg Ala Ile Tyr
                420                 425                 430

Asn Asn Met Lys Gln Phe Ile Arg Tyr Leu Ile Ser Ser Asn Val
                435                 440                 445
```

NA+/K+-ATPASE-SPECIFIC PEPTIDE INHIBITORS/ACTIVATORS OF SRC AND SRC FAMILY KINASES

CROSS-REFERENCE TO RELATED APPLICATIONS

This application is a divisional application of Ser. No. 12/446,856 filed Apr. 23, 2009, now U.S. Pat. No. 8,283,441, which claims the benefit of PCT application No. PCT/US07/23011, filed Oct. 31, 2007, published, which claims priority to U.S. Provisional Application No. 60/855,482, filed Oct. 21, 2006, the disclosures of which are incorporated herein by reference.

STATEMENT REGARDING FEDERALLY SPONSORED RESEARCH

This invention was made with government support under Grant numbers HL-036573 and HL-067963 awarded by National Institutes of Health. The government has certain rights in the invention.

TECHNICAL FIELD AND INDUSTRIAL APPLICABILITY OF THE INVENTION

The identified peptides are useful as therapeutics and/or as a protomer for developing better therapeutics for treatments of cancer and other diseases in which Src and Src family kinases are either highly elevated or genetically and/or functionally reduced. These disease states include, but not limited to, leukemia, prostate and breast cancers, ischemia/reperfusion injury, uremic cardiomyopathy, hypertension, cardiac fibrosis, and comprised myocardial contractility. Moreover, as evidenced by the identified peptides, it is feasible to utilize the newly discovered Na+/K+-ATPase/Src receptor complex as a target for developing novel receptor agonists and antagonists as well as new Src and Src family kinase inhibitors and activators.

BACKGROUND OF THE INVENTION

Cardiotonic steroids (CTS) consist of a group of chemicals that specifically bind to the Na+/K+-ATPase. They include plant-derived digitalis drugs such as digoxin and ouabain and vertebrate-derived aglycone such as bufalin and marinobufagenin. Recent studies have identified both ouabain and marinobufagenin as endogenous steroids whose production and secretion are regulated by multiple physiological and pathological stimuli including angiotensin II and epinephrine in humans. These steroids can activate protein kinases and regulate cell growth, gene expression, intracellular calcium, and reactive oxygen species (ROS) concentrations, thus playing important roles in the control of renal and cardiovascular functions, protection of ischemia/reperfusion injury and stimulation or inhibition of cell growth.

Src family kinases are 52-62-kDa membrane-associated nonreceptor tyrosine kinases and they participate in several tyrosine phosphorylation-related signaling pathways in response to various extracellular ligands. Src, for example, contains at least three important protein interaction domains. The SH3 domain binds to polyproline motifs and the SH2 domain interacts with the phosphorylated tyrosine residues. The kinase domain reacts with the nucleotide and phosphorylates the substrate. Binding of protein ligands to the SH3 or SH2 domain can activate Src. Proteins that bind with kinase domain of Src were also reported to be capable of regulating Src activity.

Na+/K+-ATPase, the molecular machinery of the cellular sodium pump, belongs to a family of evolutionarily ancient enzymes that couple the hydrolysis of ATP to membrane ion translocation. It is now believed that the Na+/K+-ATPase has dual functions. It not only pumps Na+ and K+ across cell membranes, but also relays the extracellular CTS signal to intracellular compartments via activation of different protein kinases.

Specifically, the inventors discovered that the Na+/K+-ATPase interacts with Src and Src family kinases to form a functional receptor. Binding of ouabain to this receptor activates Src, which in turn phosphorylates various effectors, resulting in the assembly and activation of different pathways including the Ras/Raf/ERK1/2 and phospholipase C/protein kinase C cascades as well as increases in intracellular Ca2+ and cellular ROS production. The activation of these signaling pathways eventually leads to changes in cardiac and renal functions, stimulation of cell proliferation and tissue fibrosis, protection of tissue against ischemia/reperfusion injury and inhibition of cancer cell growth. These effects occur in a tissue/cell-specific manner.

Because Src and Src family kinases play an important role in cellular signal transduction, many researchers are engaged in searching for kinase-specific and pathway-specific inhibitors. So far, many inhibitors have been developed, and most of them are developed as ATP analogs that compete for ATP binding to these kinases, resulting in inhibition of kinase activity. However, the lack of pathway specificity is a major disadvantage of the current Src inhibitors. Since Src and Src family kinases are essential for many cellular functions, a generic inhibition could compromise the overall benefit of the treatment. In the past, this has been evident by severe side effects of these inhibitors in animal studies. In addition, some of these inhibitors exhibit cross-activity toward receptor tyrosine kinases.

Cardiotonic steroids have been used as drugs to treat congestive heart failure and other cardiac diseases because they increase intracellular Ca2+ and thus contractility. However, these chemicals not only activate Na+/K+-ATPase-related cellular signaling pathways, but also inhibit the ion pumping function of Na+/K+-ATPase. The latter contributes to their clinical side effects and limits the clinical applications of these drugs. Endogenous cardiotonic steroids are hormones that regulate renal and cardiovascular functions. Over-stimulation of the newly discovered Na+/K+-ATPase/Src by these hormones is known to cause high blood pressure and induce abnormal cell proliferation in renal epithethial cells as well as induce tissue fibrosis.

Considering the above-mentioned concerns, it is clear that there remains a need in the art for a method of developing a pathway (e.g., Na+/K+-ATPase)-specific Src inhibitor or activator that can be used to block endogenous CTS-activated Src pathways or stimulate the Na+/K+-ATPase-associated Src to mimic the CTS effect without inhibiting the ion pumping function of Na+/K+-ATPase. Moreover, there is a need for targeting the newly discovered Na+/K+-ATPase/Src receptor complex to develop novel agonists or antagonists of the receptor so that the receptor function of Na+/K+-ATPase/Src complex can be either stimulated for treating diseases such as congestive heart failure and ischemia/reperfusion injury or inhibited for treating diseases such as tissue fibrosis and cancer.

There is also a need for assays to monitor Src interaction with the Na+/K+-ATPase and kinase enzymatic activities that are sensitive, simple to use, and adaptable to high-throughput screening methods.

There is also a need for a method for isolating operationally defined ligands involved in protein-protein interactions and for optimally identifying an exhaustive set of modular domain-containing proteins implicated in binding with the ligands.

If such a method were available, however, such a method would be useful for the isolation of any polypeptide having a functioning version of any functional domain of interest.

Such a general method would be of tremendous utility in that whole families of related proteins each with its own version of the functional domain of interest could be identified. Knowledge of such related proteins would contribute greatly to our understanding of various physiological processes, including cell growth or death, malignancy, renal/cardiovascular function and immune reactions, to name a few.

Such a method would also contribute to the development of increasingly more effective therapeutic, diagnostic, or prophylactic agents having fewer side effects.

According to the present invention, just such a method is provided.

SUMMARY OF THE INVENTION

In one aspect, provided herein is a method for regulating Src and its downstream signaling pathway comprising binding between Src and Na+/K+-ATPase.

In another aspect, provided herein is a receptor for inducing ouabain-provoked signal transduction comprising a complex of the Na+/K+-ATPase/Src or Src family kinase.

In another aspect, provided herein is a target comprising interacting sites between the Na+/K+-ATPase and Src or Src family kinases.

In another aspect, provided herein is a pharmaceutical composition for regulation of various signaling pathways involved in control of cell growth, mobility, production of reactive oxygen species (ROS), por-collagen synthesis, and muscle contraction, the composition comprising one or more Src and Src family kinases, inhibitors or activators. In certain embodiments, the composition comprises one or more peptides or peptide fragments that inhibit or stimulate the signaling function of Na+/K+-ATPase and do not inhibit the ion pumping function of Na+/K+-ATPase. Also, in certain embodiments, the inhibitors do not directly compete with ATP.

In another aspect, provided herein is an Src inhibitor or activator comprising Na+/K+-ATPase or Src sequence which interfers with the interaction between Src and Na+/K+-ATPase, acts via a different mechanism from ATP analogues, and is pathway (Na+/K+-ATPase) specific.

In another aspect, provided herein is a therapeutic composition comprising at least one peptide Src inhibitor or activator as described herein.

In another aspect, provided herein is a method for developing small molecules that mimic the peptide inhibitor or activator, acts via a different mechanism from ATP analogues, and is pathway (Na+/K+-ATPase) specific.

In another aspect, provided herein is a signal transducer comprising Na+/K+-ATPase which mediates one or more signaling pathways that are related to cancer cell growth, cardiac fibrosis, ischemia/reperfusion injury, muscle contraction, or uremic cardiomyopathy.

In another aspect, provided herein is a composition comprising a functional domain found in either Src or the Na+/K+-ATPase alpha 1 subunit, wherein Na+/K+-ATPase-mediated inhibition of Src is due to the interaction between the N domain of the alpha subunit or the alpha subunits of other P-type ATPases and the Src kinase domain.

In another aspect, provided herein is a composition comprising the ND1 peptide, or fragments thereof.

In another aspect, provided herein is a peptide derived from ND1 which is sufficient to bind and inhibit Src activity as well as other Src family kinases, including, but not limited to, Lyn.

In another aspect, provided herein is a peptide derived from a Src kinase domain (KD1) or similar domains from other Src family kinases capable of binding with Na+/K+-ATPase and effective in activating the Na+/K+-ATPase-inhibited Src by competing the binding motif for Src.

In another aspect, provided herein is a peptide useful to activate or inhibit Na+/K+-ATPase pathway-specific Src or Src family kinases.

In another aspect, provided herein are Src inhibitors and/or activators comprising a peptide or fragment thereof that targets a region that i) specifically interact with Na+/K+-ATPase or Src, other than competing for ATP binding, and ii) provides a pathway-specific modulation of Src activity.

In another aspect, provided herein are isoform-specific Src inhibitors and/or activators for individual Src family kinases comprising a kinase having a sequence, or fragment thereof, developed using one or more alpha subunits of Na+/K+-ATPase that also bind the kinase domain.

In another aspect, provided herein is a small molecule comprising the isoform-specific Src inhibitors and/or activators as described herein.

In another aspect, provided herein is a rapid screen assay for large scale and high out-put screen comprising the interaction between Na+/K+-ATPase and at least one Src or Src family kinase.

In another aspect, provided herein is a method of treating a protein kinase-associated disease state, the method comprising administering a therapeutically effective amount of at least one composition as described herein to a subject in need thereof.

In another aspect, provided herein is a method wherein the disease state involves a non-receptor tyrosine kinase or a receptor tyrosine kinase employing Src or Src family kinase as an effector.

In another aspect, provided herein is a method wherein the disease state involves a cellular tyrosine kinase comprising Src.

In another aspect, provided herein is a method wherein the disease state comprises a cancer or a renal or a cardiovascular-related disease.

In another aspect, provided herein is a composition of matter comprising: a) a peptide having a length from five to fifty amino acids, the peptide comprising a motif selected from the group comprising any of the peptide sequences described herein and b) a first detectable moiety, wherein the first detectable moiety is associated with the peptide.

In another aspect, provided herein is a composition comprising or developed based on the sequence as shown in FIG. 19B [SEQ ID NO: 1].

In another aspect, provided herein is a composition comprising or developed based on the sequence as shown in FIG. 20B [SEQ ID NO: 34].

In another aspect, provided herein is a composition comprising or developed based on the peptide sequence as shown in FIG. 24A [SEQ ID NO: 2].

In another aspect, provided herein is a composition comprising or developed based on the structure information of the interaction between the Na+/K+-ATPase and Src or Src family kinases.

In another aspect, provided herein is a small molecule Src inhibitor or activator developed to target or based on the interaction between the Na+/K+-ATPase and Src or Src family kinases.

In another aspect, provided herein is a Src inhibitor or activator developed based on the interaction between H+/K+-ATPase or other P-ATPases and Src or Src family kinases.

In another aspect, provided herein is a method of developing either agonists or antagonists of the identified Na+/K+-ATPase/Src receptor complex.

In another aspect, provided herein is a composition comprising an agonist or antagonist developed based on the Na+/K+-ATPase/Src complex.

In another aspect, provided herein is a therapeutic composition comprising at least one agonist or antagonist as described herein.

In another aspect, provided herein is a method for manipulating cellular Na+/K+-ATPase in cultured cells comprising transfecting cells with the A4 siRNA expression vector, whereby the expression of Na/K-ATPase in the cloned cells is reduced.

In another aspect, provided herein is a method for at least partially silencing the expression of endogenous α1 in cultured cells comprising transfecting cells with the A4 siRNA expression vector, whereby the expression of α1 in the cloned cells is reduced.

In another aspect, provided herein is a method for depleting endogenous Na+/K+-ATPase without requiring the use of ouabain to force the expression of the transfected Na+/K+-ATPase, comprising using A4 siRNA to silence the α1 expression in cells derived from a desired species including human and pig.

In another aspect, provided herein is an expression vector comprising GST-NT (amino acid residue 6-90) [SEQ ID NO: 51].

In another aspect, provided herein is an expression vector comprising GST-CD2 (amino acid residue 152-288) [SEQ ID NO: 52].

In another aspect, provided herein is an expression vector comprising GST-CD3 (amino acid residue 350-785) [SEQ ID NO: 53].

In another aspect, provided herein is a construct comprising GST-H+/K+-CD3. [SEQ ID NO: 54].

In another aspect, provided herein is a construct comprising GST-SERCA-CD3. [SEQ ID NO: 55].

In another aspect, provided herein is a siRNA-based assay configured to determine the effect of changes in the amount and properties of the Na+/K+-ATPase on both basal and ouabain-stimulated Src activity.

In another aspect, provided herein is α1-depleted cells useful for determining signaling functions of an exogenous/mutant α1 made by transfecting the knockdown cells with a α1 expression vector in which A4 siRNA-targeted sequence was silently mutated wherein the exogenous α1 is knocked in and expression of α1 is restored, not only the total cellular Na+/K+-ATPase protein but also the Na+/K+-ATPase activity.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent with color drawings will be provided by the United States Patent and Trademark Office upon request and payment of necessary fee. FIGS. 1A and B. Interaction between Na+/K+-ATPase and Src in LLCPK1 cells.

FIG. 1A. Colocalization of the Na+/K+-ATPase (red) and Src (green) in LLC-PK1 cells at a resolution of 1024×1024 pixels. Left and center images showed the membrane localization of the Na+/K+-ATPase α1 and Src, respectively, and the merged image (right) showed the colocalization of these two proteins. Scale bar, 20 μm.

FIGS. 2A and 2B. The Coomassie blue-stained GST-Src and purified Na+/K+-ATPase (PKE). FIG. 2B shows that the α1 and β1 subunits are associated in a 1:1 molar ratio and account for more than 90% of protein contents in the purified Na+/K+-ATPase preparation.

FIG. 2C. A representative Western blot from three independent experiments showing the pulldown products probed with anti-Na+/K+-ATPase α1 antibody.

FIG. 2D. The same pulldown assay as in C was performed, and 650 ng (one-third of the total input) of the purified Na+/K+-ATPase (PKE) was directly loaded as an input control.

FIG. 3A. Schematic presentation of structures of Src.

FIG. 3B. Coomassie blue staining of GST-Src, GST-SH2, GST-SH3, GST-SH3SH2, and GST-kinase.

FIG. 3C. Binding of GST-Src, GST-SH3SH2, GST-kinase, GST-SH2, but not GST-SH3, domains to the Na+/K+-ATPase. An aliquot (2 μg) of the purified Na+/K+-ATPase was used for each binding assay. The same experiments were repeated three times.

FIG. 4A. Schematic presentation of α1 subunit of Na+/K+-ATPase. NT, N-terminus; CD2, cytosolic domain 2; CD3, cytosolic domain 3; PD, phosphorylation domain; ND, nucleotide-binding domain; CT, C-terminus.

FIG. 4B. A representative Western blot of four independent experiments shows the binding of purified Src (lacking of first 84 amino acids) to the CD3, but not the NT of the α1 subunit when 200 ng of Src was used.

FIG. 4C. A Western blot showing that Src was pulled down by GST-CD3 of Na+/K+-ATPase (Na/K) and H+/K+-ATPase (H/K), but not SERCA from 1 mg LLC-PK1 cell lysates.

FIG. 4D. A Western blot showing the domain interaction between the Na+/K+-ATPase and Src. Different GST-fused Na+/K+-ATPase domain constructs were incubated with either His-tagged SH3SH2 domain or kinase domain of Src, and the pulldown products were analyzed by Western blot.

FIG. 5A. Indicated amount of purified Na+/K+-ATPase (PKE) were incubated with recombinant Src (4.5 U) for 30 min in PBS, then 2 mM ATP/Mg2+ was added and incubated for another 5 min. After the samples were resolved on SDS-PAGE, the membranes were probed with antibodies as indicated. * p<0.05; ** p<0.01 compared with control.

Figure 5A:
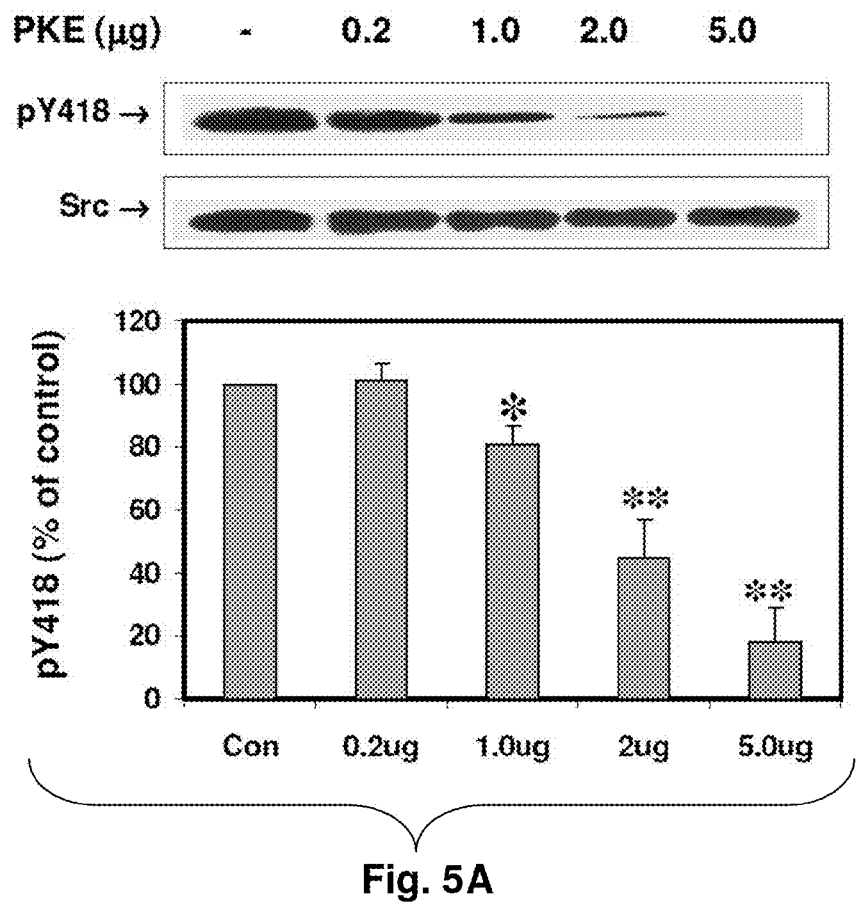
FIGS. 5A-B. Regulation of Src by the Na+/K+-ATPase and GST-CD3.
Figure 5B:
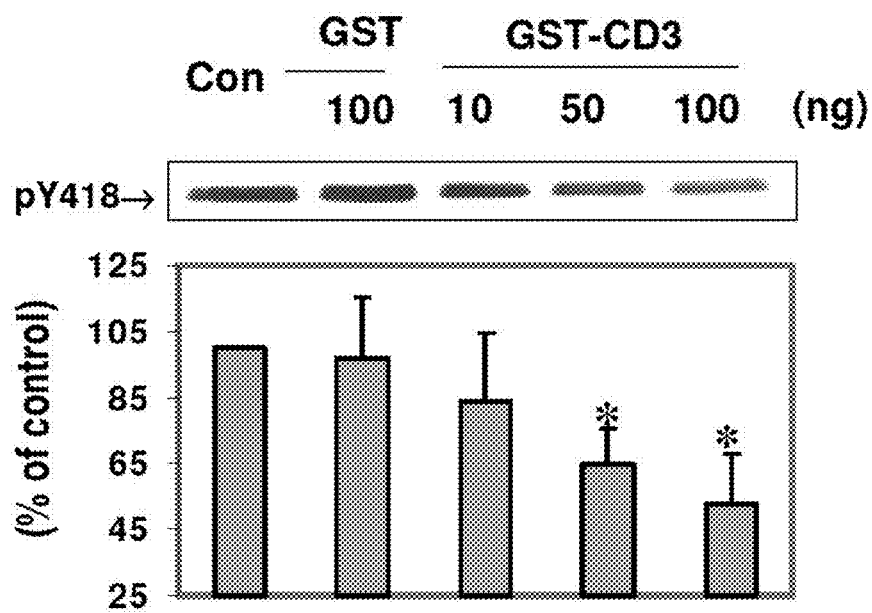

FIG. 5B. GST (100 ng) or different amount of GST-CD3 was incubated with recombinant Src (4.5 U) for 30 min in PBS. The phosphorylation of Src was analyzed as in A. Values are mean±SE of at least four independent experiments. * p<0.05 compared with control.

Figure 6A:
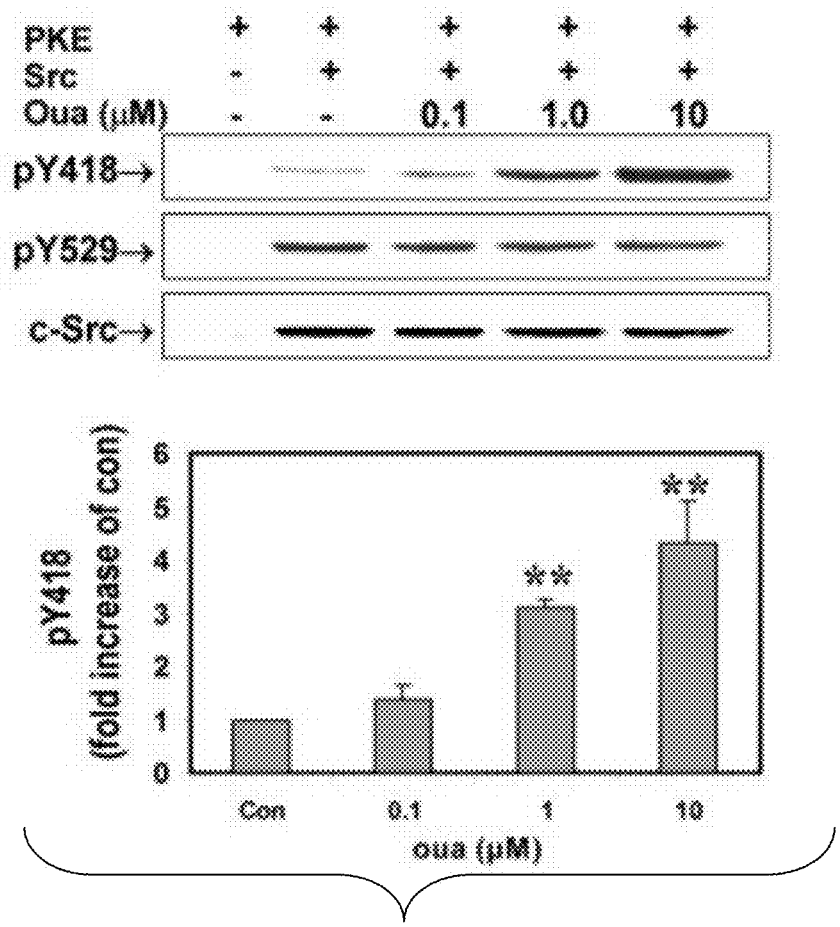
Figure 6B:
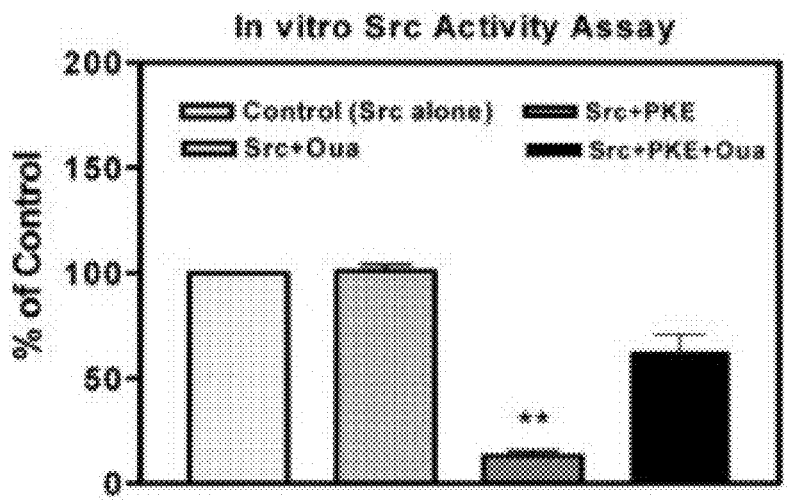
Figure 6C:
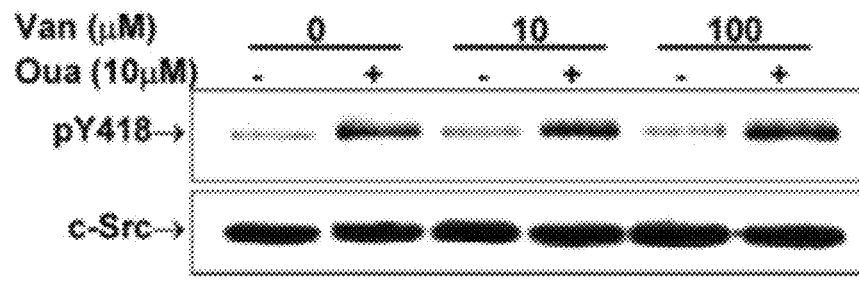

FIGS. 6A-C. Stimulation of the Na+/K+-ATPase/Src complex by ouabain:

FIG. 6A. The preformed Na+/K+-ATPase/Src complex was treated with different concentrations of ouabain in the presence of 2 mM ATP/Mg2+ for 5 min, and the phosphorylated Src was analyzed using site-specific antibodies as indicated. Values are mean±SE of at least four independent experiments. ** p<0.01 compared with control.

FIG. 6B. Src or Src/Na+/K+-ATPase complex was treated with 10 μM ouabain, and the Src activity was measured. ** p<0.01 compared with control.

FIG. 6C. A representative Western blot of four experiments showing the effects of ouabain and vanadate on the Na+/K+-ATPase/Src complex. A similar experiment as in A was repeated to assess the effects of either vanadate (Van) or vanadate plus ouabain (Oua) on Src phosphorylation.

Figure 7A:
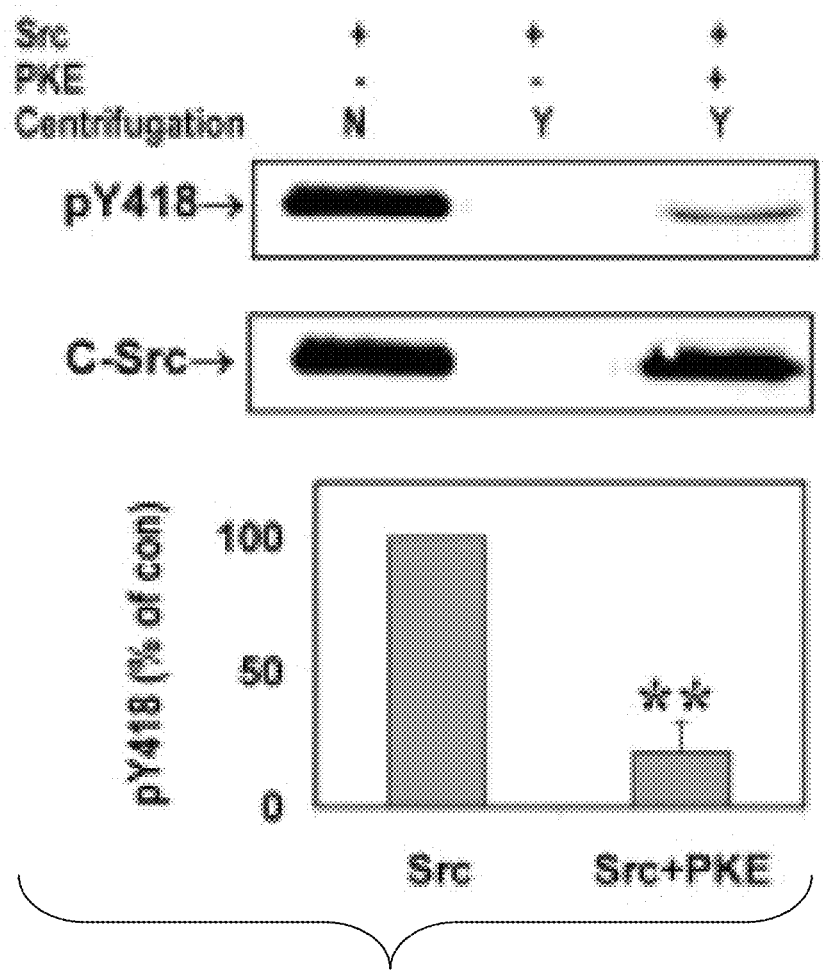

FIGS. 7A-D. Activation of Src by freeing the kinase domain from the Na+/K+-ATPase:

FIG. 7A. A control experiment showing that Src could be cosedimented with Na+/K+-ATPase. Src (4.5 U) incubated with or without 5 μg Na+/K+-ATPase in 0.5 ml PBS was centrifuged at 100,000×g for 30 min. The pellets were resuspended in PBS and subjected to phosphorylation assay as described in Materials and Methods. As an input control, 4.5 U of Src were directly suspended in PBS and assayed for pY418 phosphorylation. ** p<0.01.

Figure 7B:
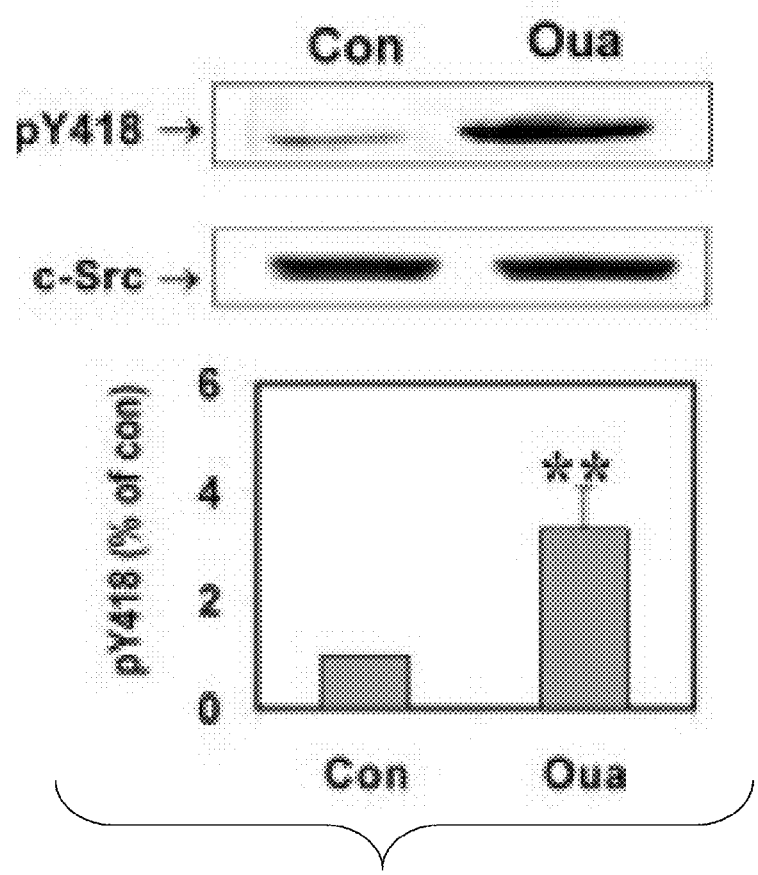

FIG. 7B. Src (4.5 U) was preincubated with 5 μg of the purified Na+/K+-ATPase in PBS and then exposed to 10 μM ouabain for 15 min. Both control and ouabain-treated Na+/K+-ATPase/Src complexes were then collected by centrifugation, resuspended in PBS, and subjected to phosphorylation assay as in A. Two representative Western blots are shown in A and B, and the values are mean±SE of at least three independent experiments. ** p<0.01.

Figure 7C:
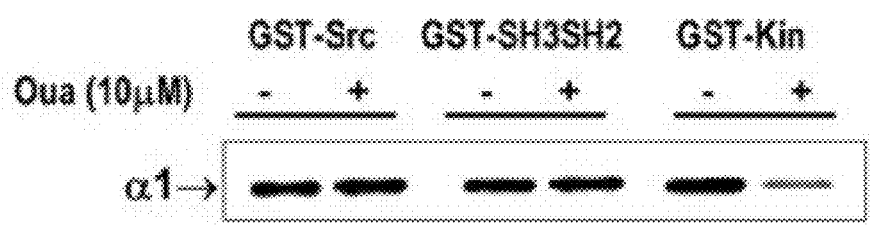

FIG. 7C. A representative Western blot of four separate experiments showing that ouabain induced the release of the kinase domain from the Na+/K+-ATPase. GST-Src, GST-SH3SH2, or GST-kinase was incubated with 1 μg purified Na+/K+-ATPase for 30 min at room temperature in 500 μl PBS. Complexes were then pulled down on glutathione beads, washed three times, resuspended in 500 μl PBS, and exposed to 10 μM ouabain for 15 min. The beads were then washed for three more times using PBS, and the pulled down Na+/K+-ATPase was analyzed by Western blot using anti-α1 antibody FIG. 7D. A representative Western blot of three independent experiments showing the activation of Src by GST-kinase domain fusion protein. GST, GST-SH3SH2, or GST-kinase (5 μg each) was preincubated with 2 μg of the purified Na+/K+-ATPase for 15 min at room temperature. Recombinant Src (4.5 U) was then added to the mixture for additional 30 min. Phosphorylation reaction was started by addition of 2 mM ATP/Mg2+ and Src pY418 was measured as in A.

Figure 8A:
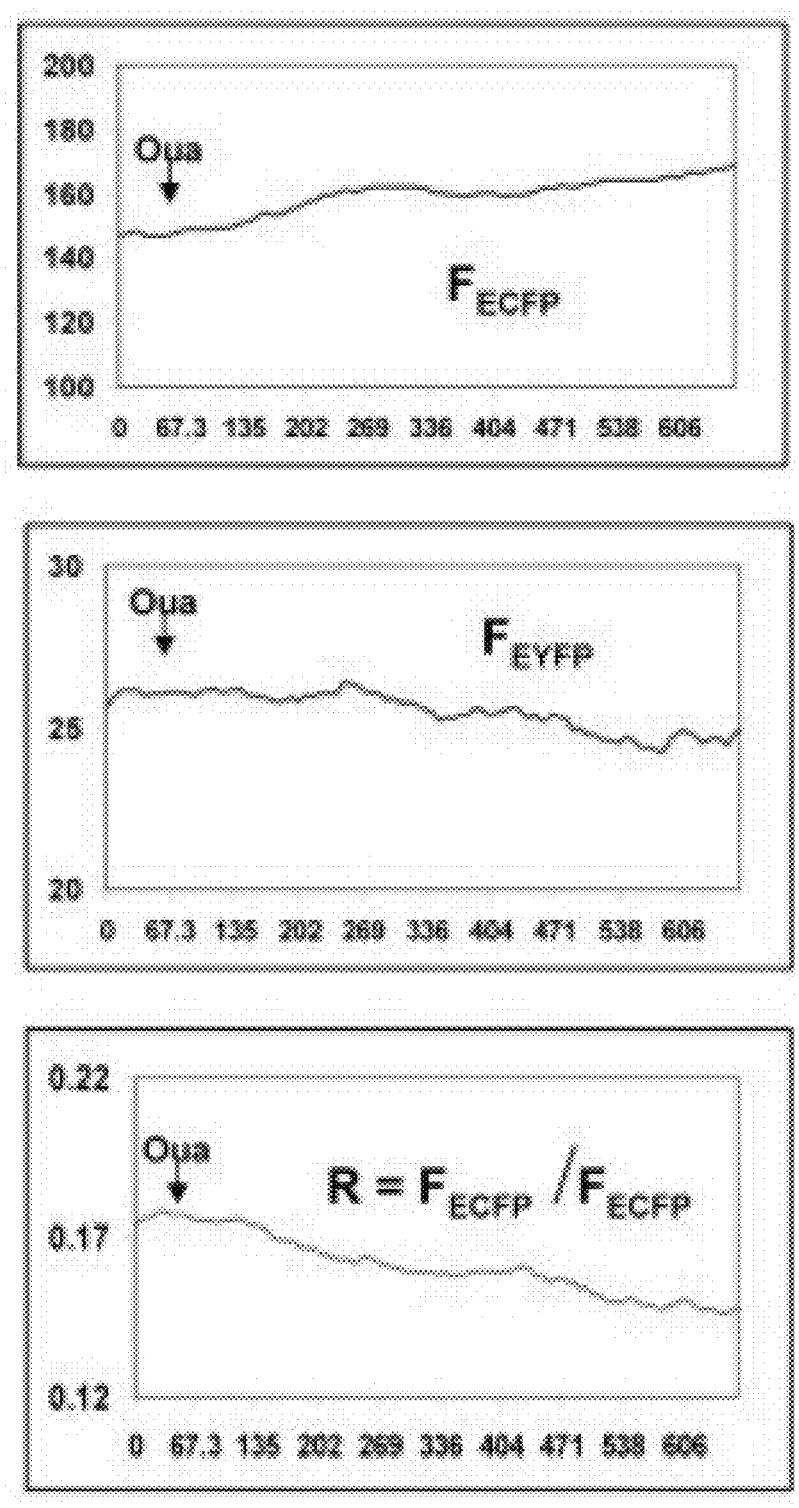
Figure 8B:
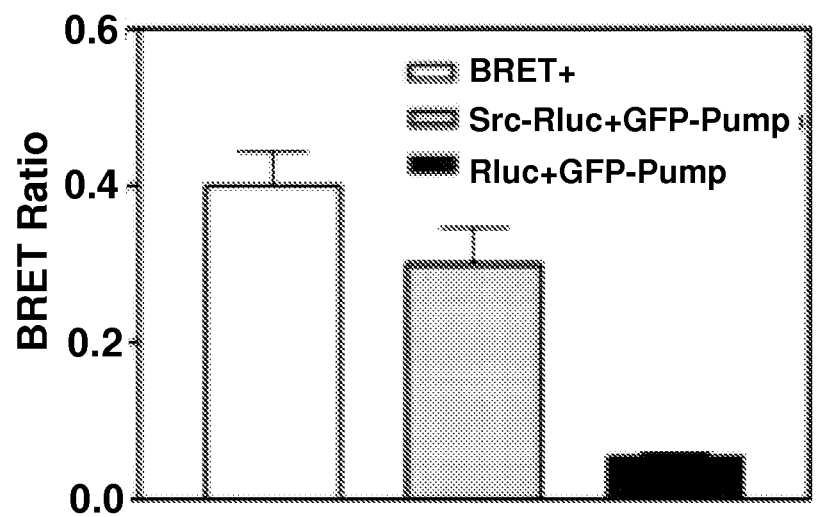
Figure 8C:
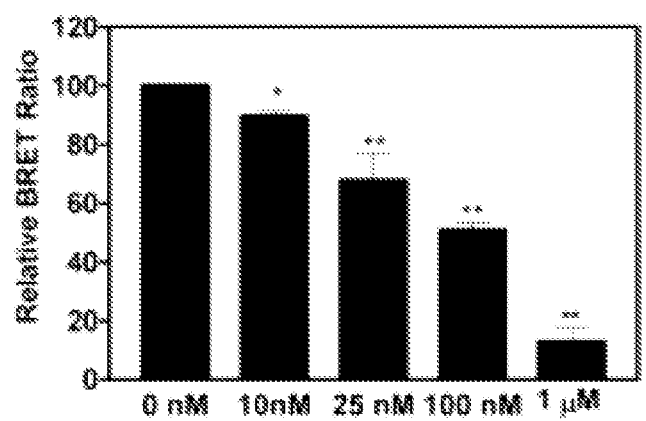

FIGS. 8A-C. Ouabain dissociates Src kinase domain from the Na+/K+-ATPase in live cells:

FIG. 8A. A representative trace of ouabain-induced changes in FRET signal in an LLC-PK1 cell.

FIG. 8B. 293T cells were cotransfected with Src-Rluc and GFP-α1. 293T cells transfected with Rluc-GFP fusion protein were used as a positive control, and cells that cotransfected with Rluc and GFP-Na+/K+-ATPase were used as a negative control.

FIG. 8C. Ouabain treatment reduced BRET signal between GFP-Na+/K+-ATPase and Src-Rluc in a dose-dependent manner. Values are mean±SE of at least four experiments. * p<0.05; ** p<0.01.

Figure 9A:
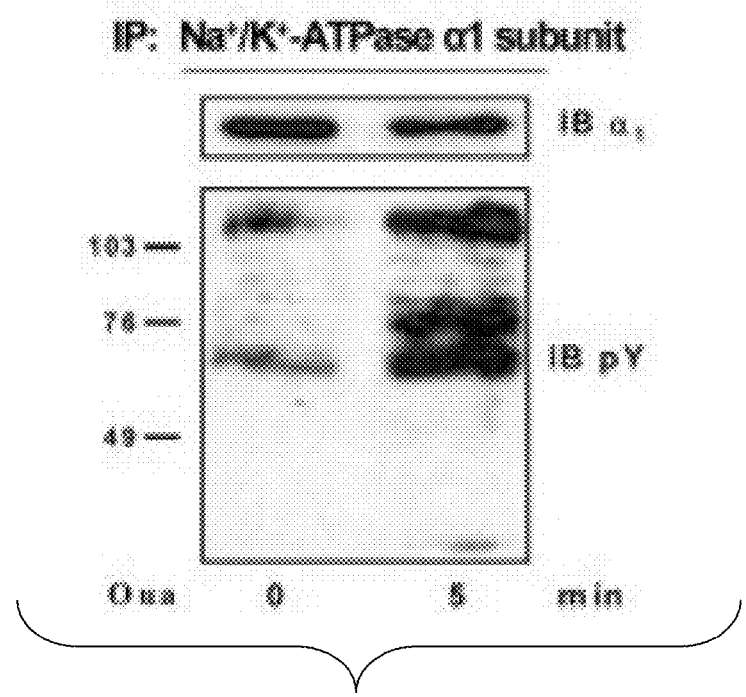

FIGS. 9A-D. Ouabain-activated Na+/K+-ATPase/Src phosphorylates and recruits downstream effectors;

FIG. 9A. LLC-PK1 cells were treated with 1 μM ouabain for 5 min, and cell lysates were immunoprecipitated with anti-α1 antibody and analyzed for tyrosine phosphorylated proteins.

Figure 9B:
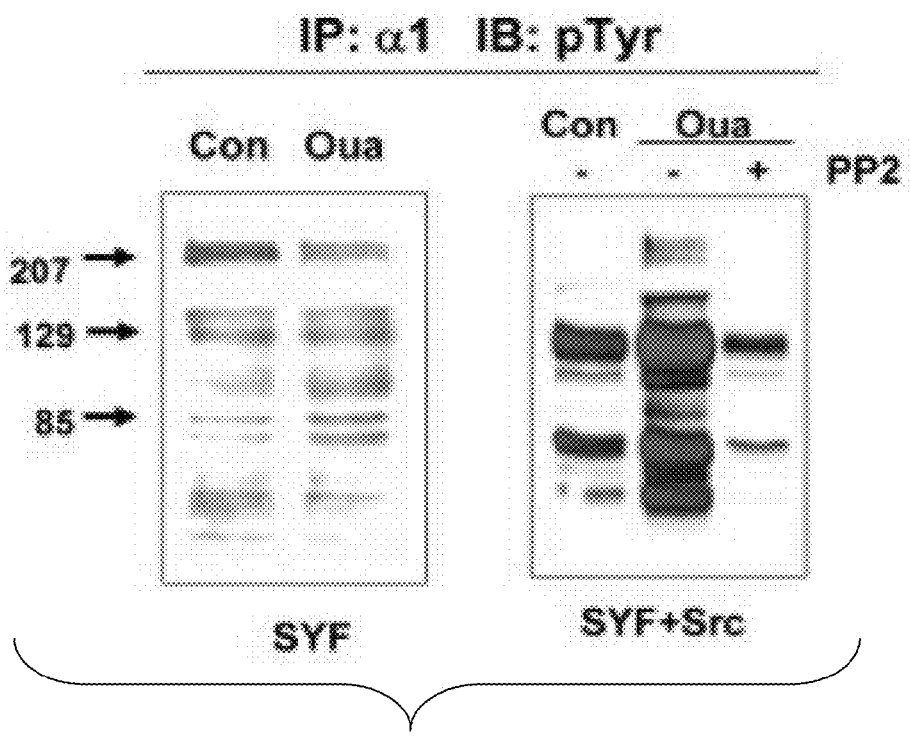

FIG. 9B. Both SYF and SYF+Src cells were treated with 100 μM ouabain for 5 min and analyzed as in A. Representative Western blots of three experiments are shown in both A and B.

Figure 9C:
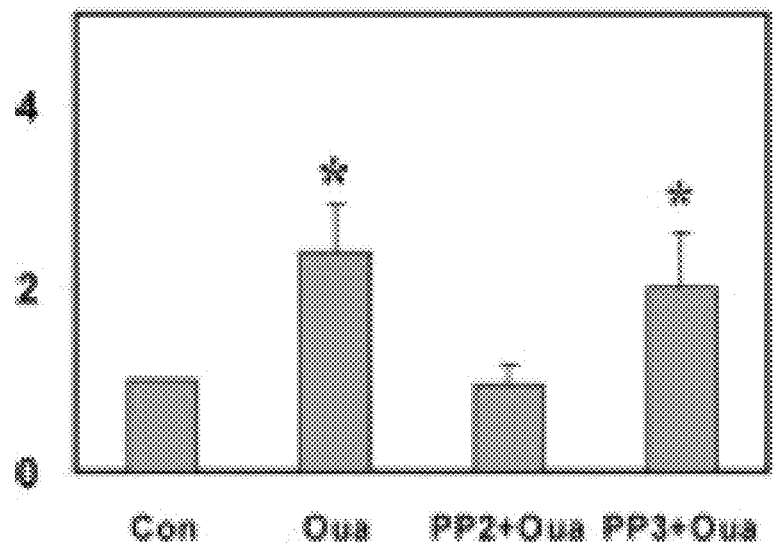

FIG. 9C. Inhibition of Src blocks ouabain-induced recruitment of Src to the Na+/K+-ATPase signaling complex. LLC-PK1 cells were pretreated with 1 μM PP2 or PP3 for 15 min and then exposed to 1 μM ouabain for 5 min. Cell lysates were immunoprecipitated and analyzed. Values are mean±SE of at least four independent experiments. * p<0.05.

Figure 9D:
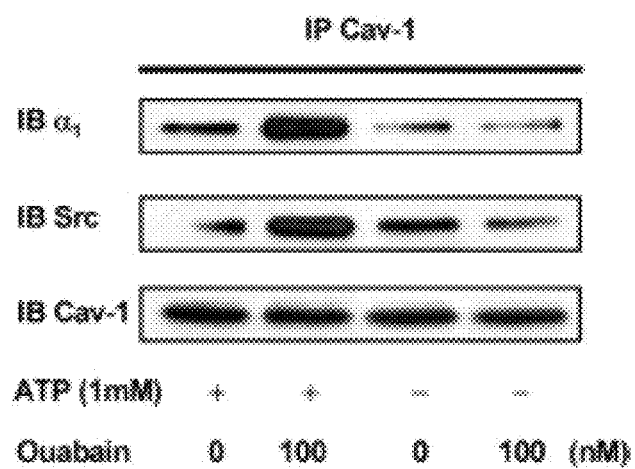

FIG. 9D. Caveolae were isolated and treated with 100 nM ouabain for 5 min in the presence or absence of 2 mM ATP as previously described (Wang et al., 2004). Afterward, caveolae were lysed in RIPA buffer, and the lysates were cleared by centrifugation and immunoprecipitated with anti-caveolin-1 antibody. Immunoprecipitates were probed for the α1, Src, and caveolin-1 by Western blot. A representative Western blot of three independent experiments is shown.

Figure 10A:
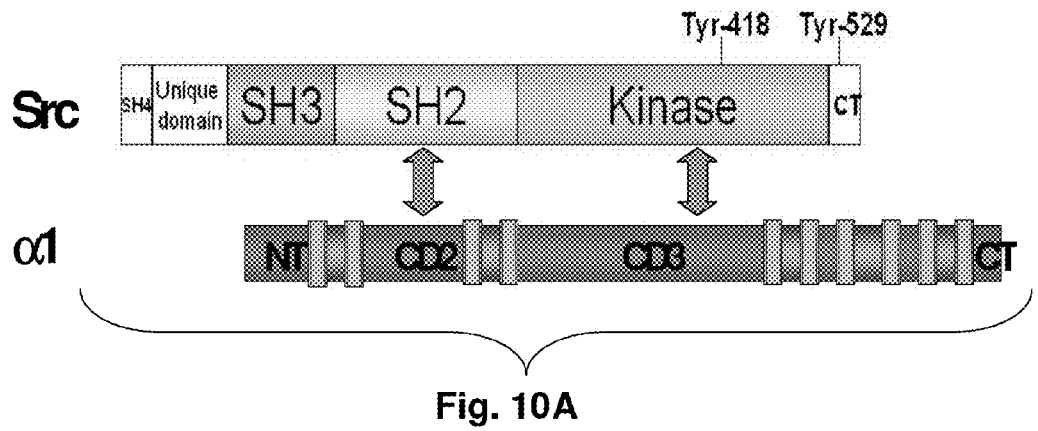
Figure 10B:
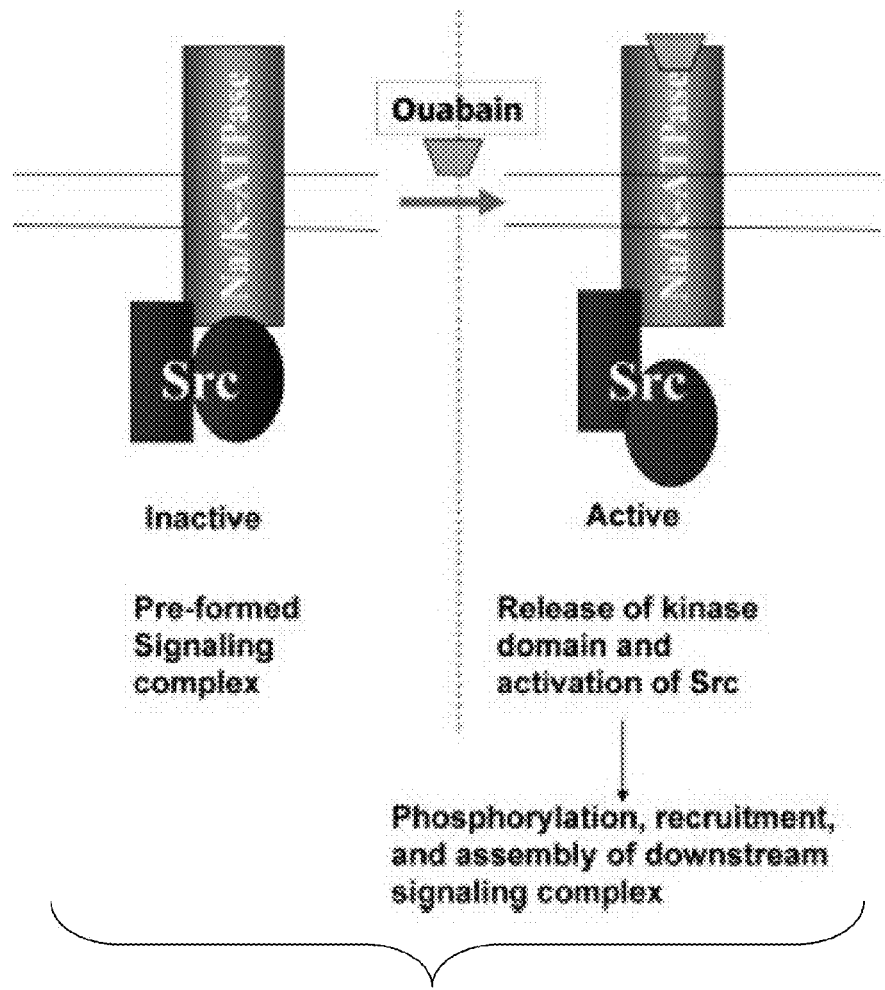

FIG. 10. Schematic presentation shows the identified interactions between the Na+/K+-ATPase and Src (A) and how ouabain regulates the Na+/K+-ATPase/Src receptor complex (B).

Figure 11A:
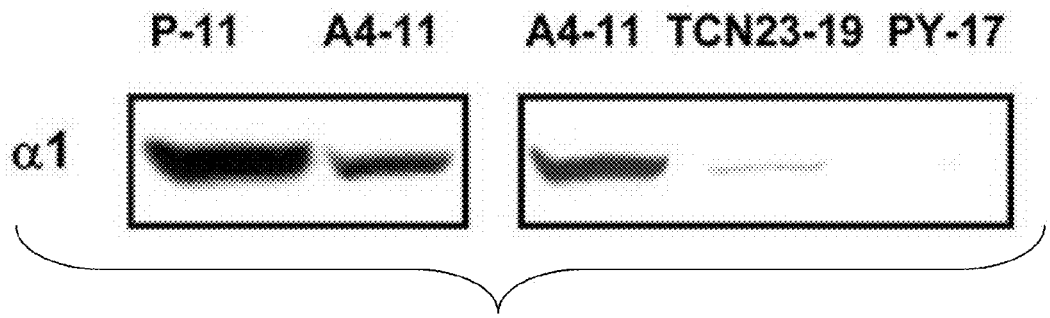
Figure 11B:
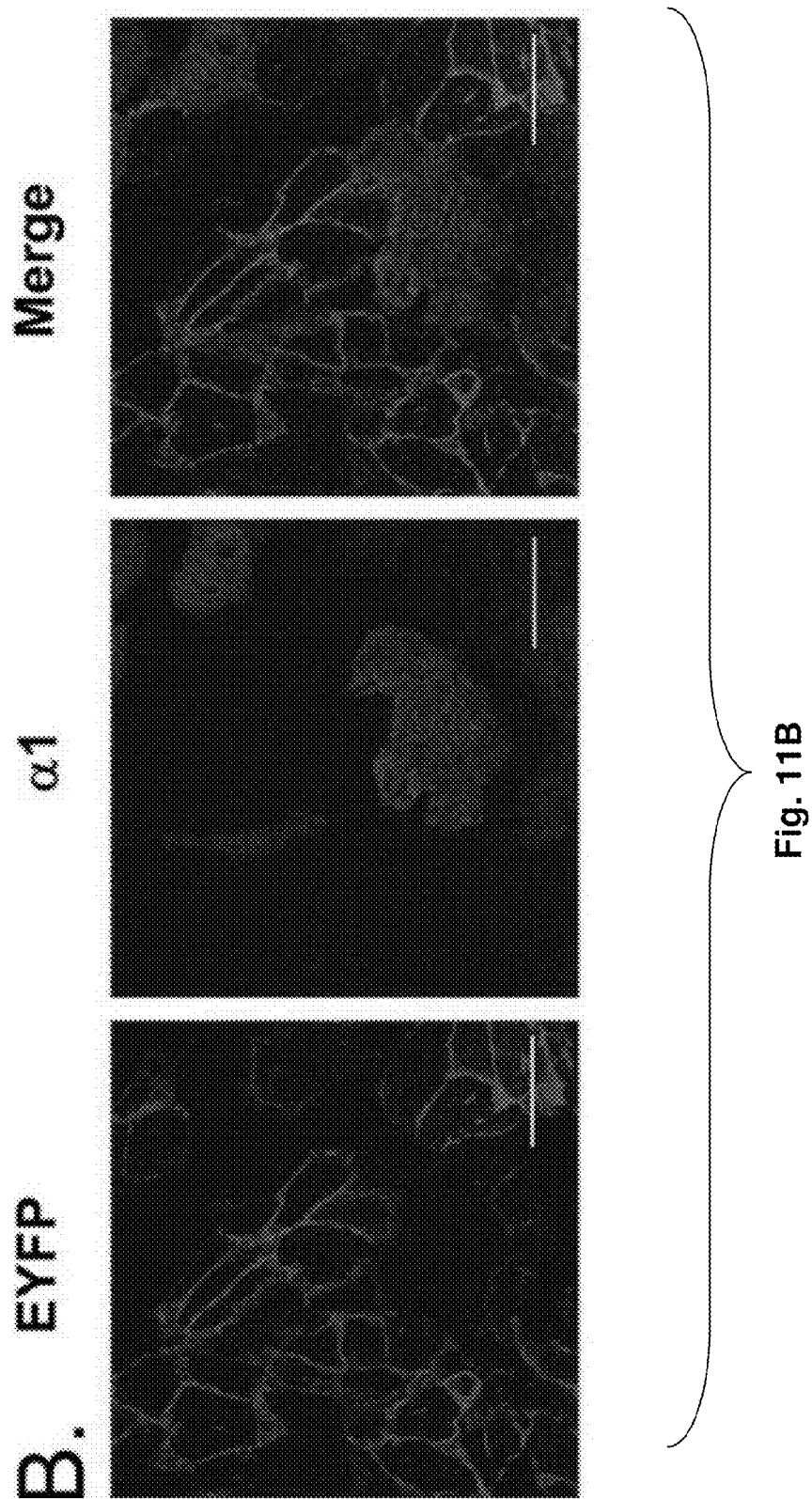

FIGS. 11A-B. Silencing of the endogenous Na+/K+-ATPase by siRNA:

FIG. 11A. Total cell lysates (30 μg/lane) from different cell lines were separated by SDS-PAGE and analyzed by Western blot for the expression of the α1 subunit of the Na+/K+-ATPase. A representative Western blot is shown (see quantitative data in Table 2).

FIG. 11B. P-11 and PY-17 cells were mixed, co-cultured for 24 h, and then immunostained with anti-α1 antibody (clone C464.6) as described under "Experimental Procedures." The scale bar represents 50 μm.

Figure 12A:
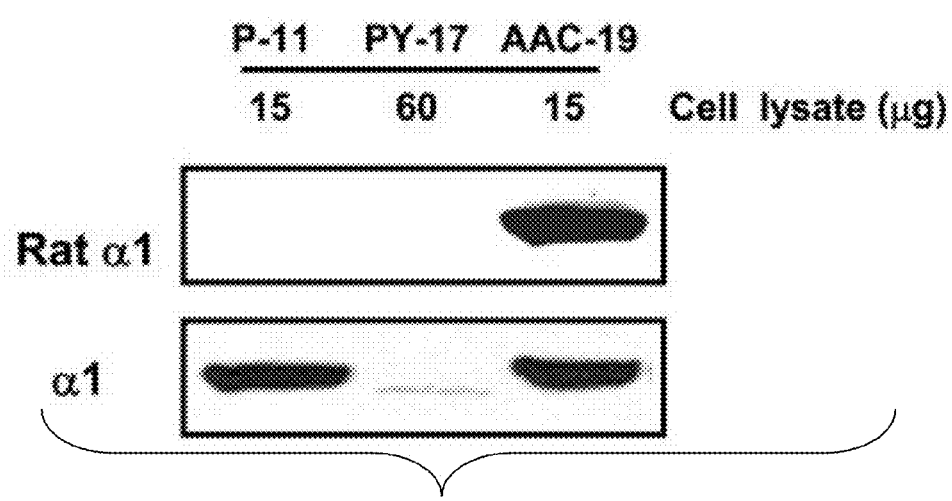

FIGS. 12A-B. Expression of the Na+/K+-ATPase in AAC-19 cells.

Figure 12:
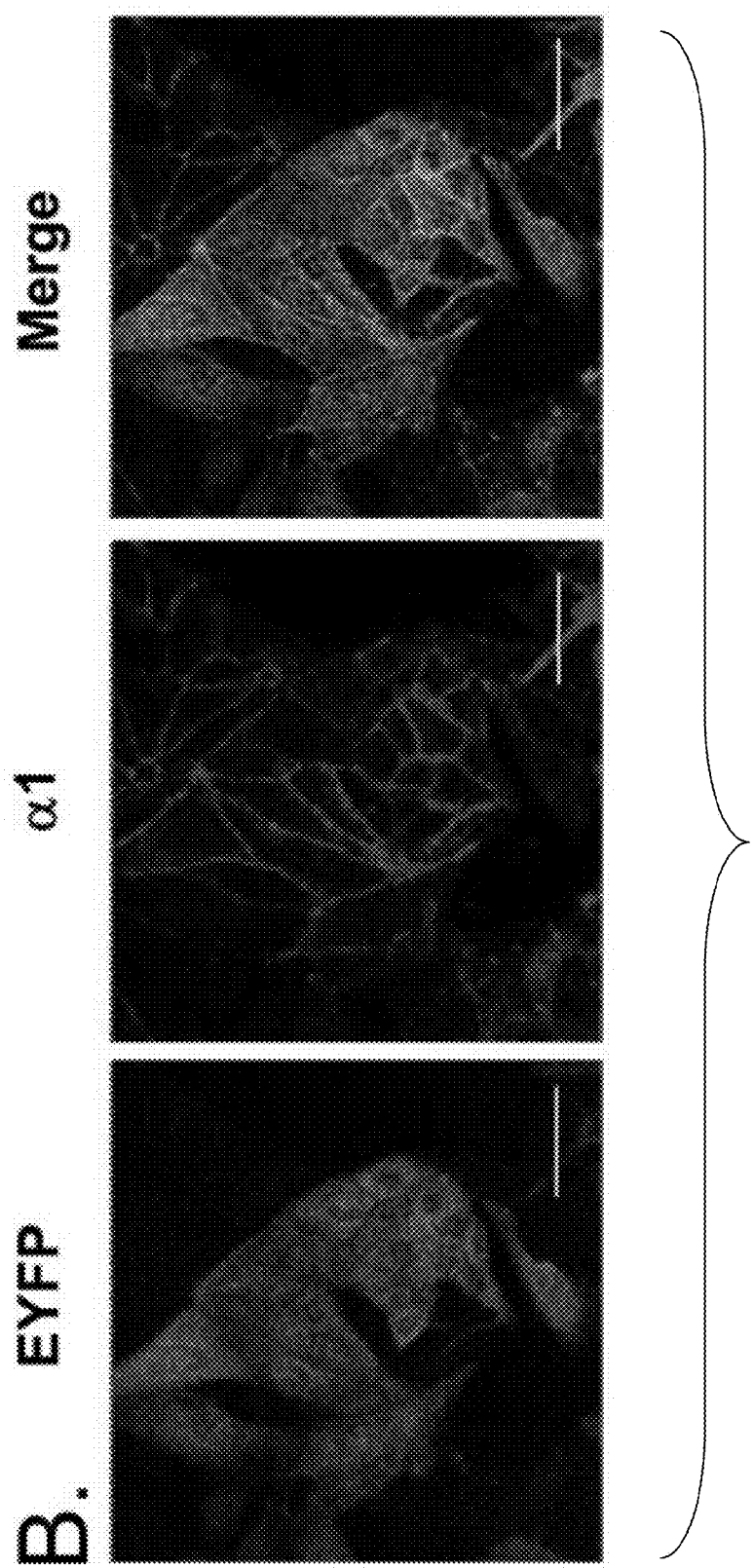

FIG. 12 A. Clone AAC-19 was generated by transfecting PY-17 cells with a rat α1-expressing vector as described under "Experimental Procedures." Cell lysates (15 μg from P-11 and AAC-19 and 60 μg from PY-17) were separated by SDS-PAGE and analyzed by Western blot. The blot was first probed with antibody α6F that recognizes both pig and rat α1 subunits, then striped, and reprobed with the anti-NASE that specifically reacts with rat α1.

FIG. 12 B. P-11 and AAC-19 cells were mixed, co-cultured for 24 h, and immunostained with anti-α1 antibody (clone C464.6) as described under "Experimental Procedures." The scale bar represents 50 μm.

Figure 13:
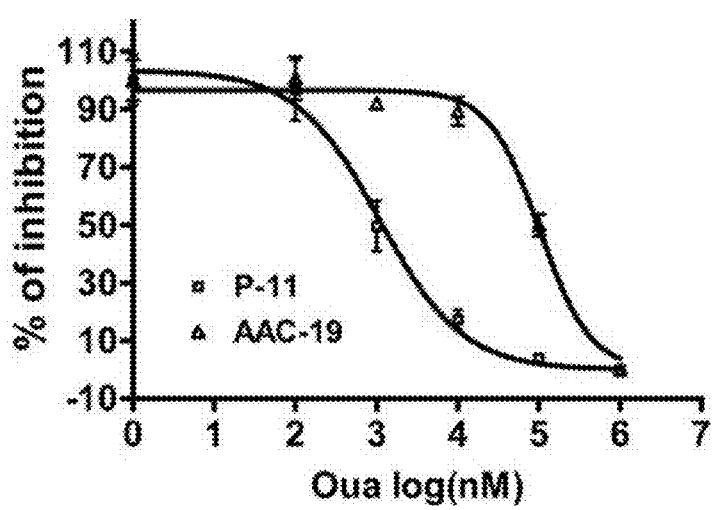

FIG. 13. Concentration-dependent effects of ouabain (oua) on the Na+/K+-ATPase activity. Whole cell lysates from P-11 and AAC-19 cells were prepared and assayed for the Na+/K+-ATPase activity as described under "Experimental Procedures." Data are shown as percentage of control, and each point is presented as mean±S.E. of four independent experiments. Curve fit analysis was performed by GraphPad software.

Figure 14A:
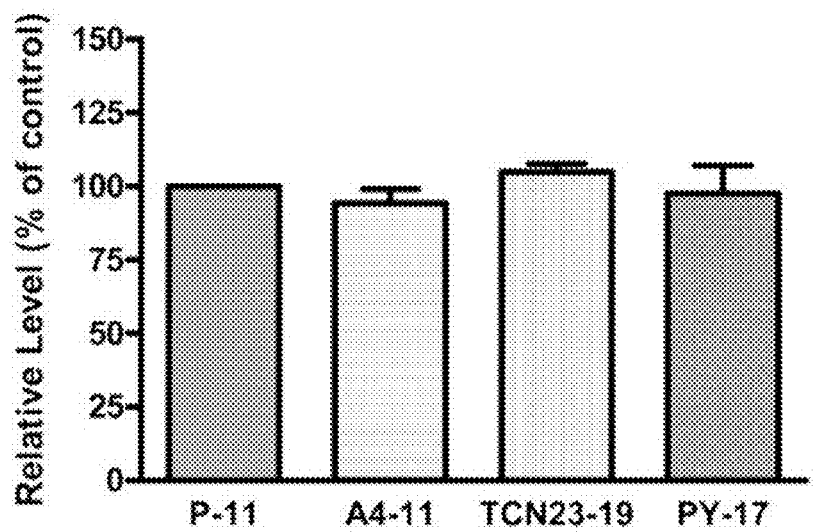
Figure 14B:
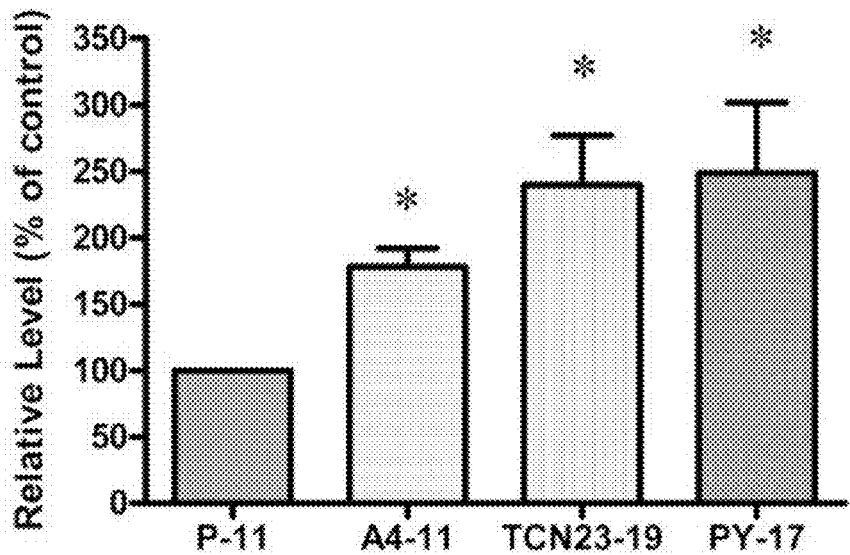
Figure 14C:
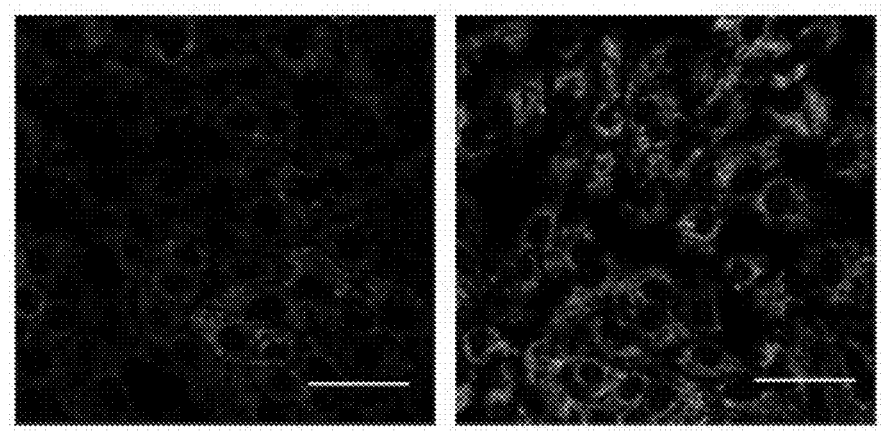

FIGS. 14A-C. Regulation of Src activity by Na+/K+-ATPase:

FIGS. 14A and 14B—cell lysates (30 μg/lane) from different cell lines were separated by SDS-PAGE and analyzed by either anti-c-Src (B-12) or anti-Tyr(P)$^{418}$-Src antibody. The quantitative data are mean±S.E. from four separate experiments. *, $p<0.05$ versus P-11.

FIG. 14C. Cultured P-11 and TCN23-19 cells were serum-starved for 12 h and immunostained by anti-Tyr(P)$^{418}$-Src antibody. The images were collected as described under "Experimental Procedures." The scale bar represents 50 μm.

Figure 15A:
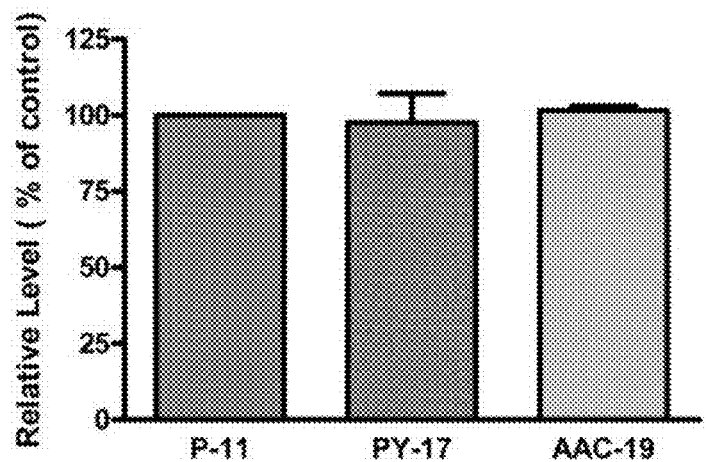
Figure 15B:
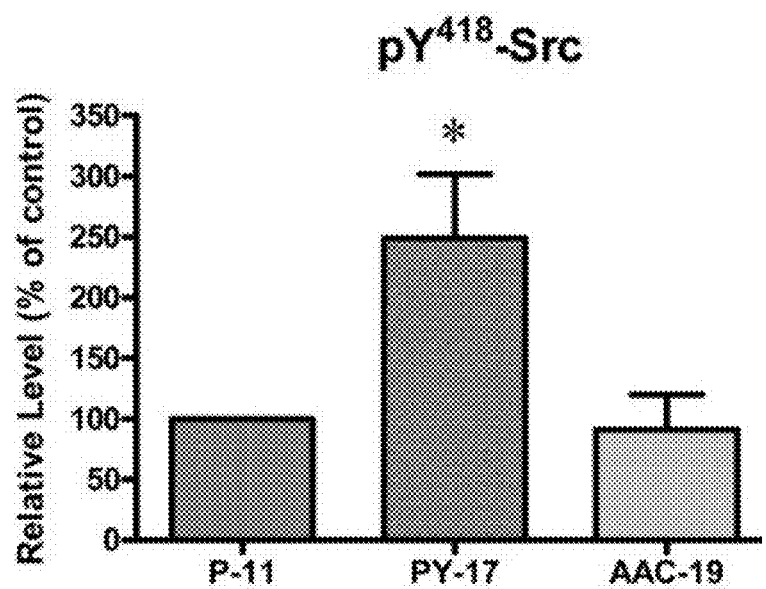

FIGS. 15A-D. Regulation of Src activity by the pumping-null Na+/K+-ATPase:

FIGS. 15A and 15B. Cell lysates (30 μg/lane) from different cell lines were separated by SDS-PAGE and analyzed by either anti-c-Src (B-12) or anti-Tyr(P)$^{418}$-Src antibody. The quantitative data are mean±S.E. from four separate experiments. *, $p<0.05$ versus P-11.

Figure 15C:
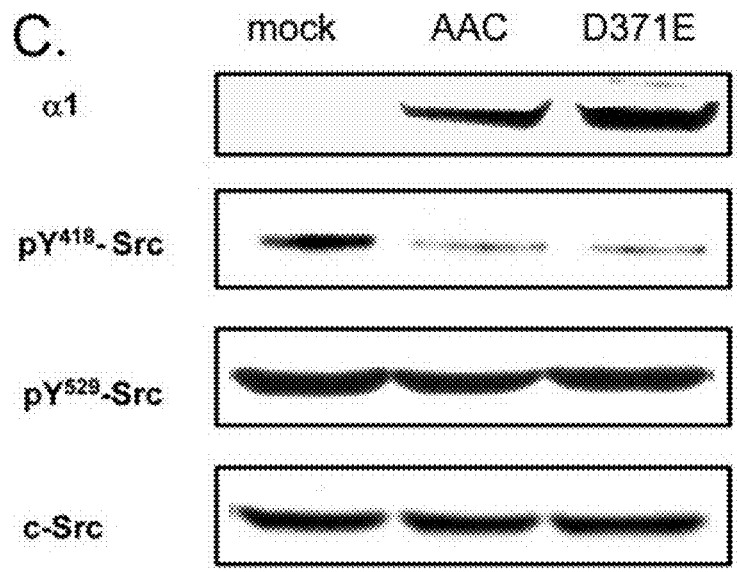

FIG. 15C. PY-17 cells were transiently transfected with either an empty vector (mock), silently mutated wild-type rat α1 (AAC), or the D371E mutant. After 36 h, the transfected cells were lysed and analyzed by Western blot using specific antibodies as indicated. A representative Western blot is shown, and the same experiments were repeated four times.

Figure 15D:
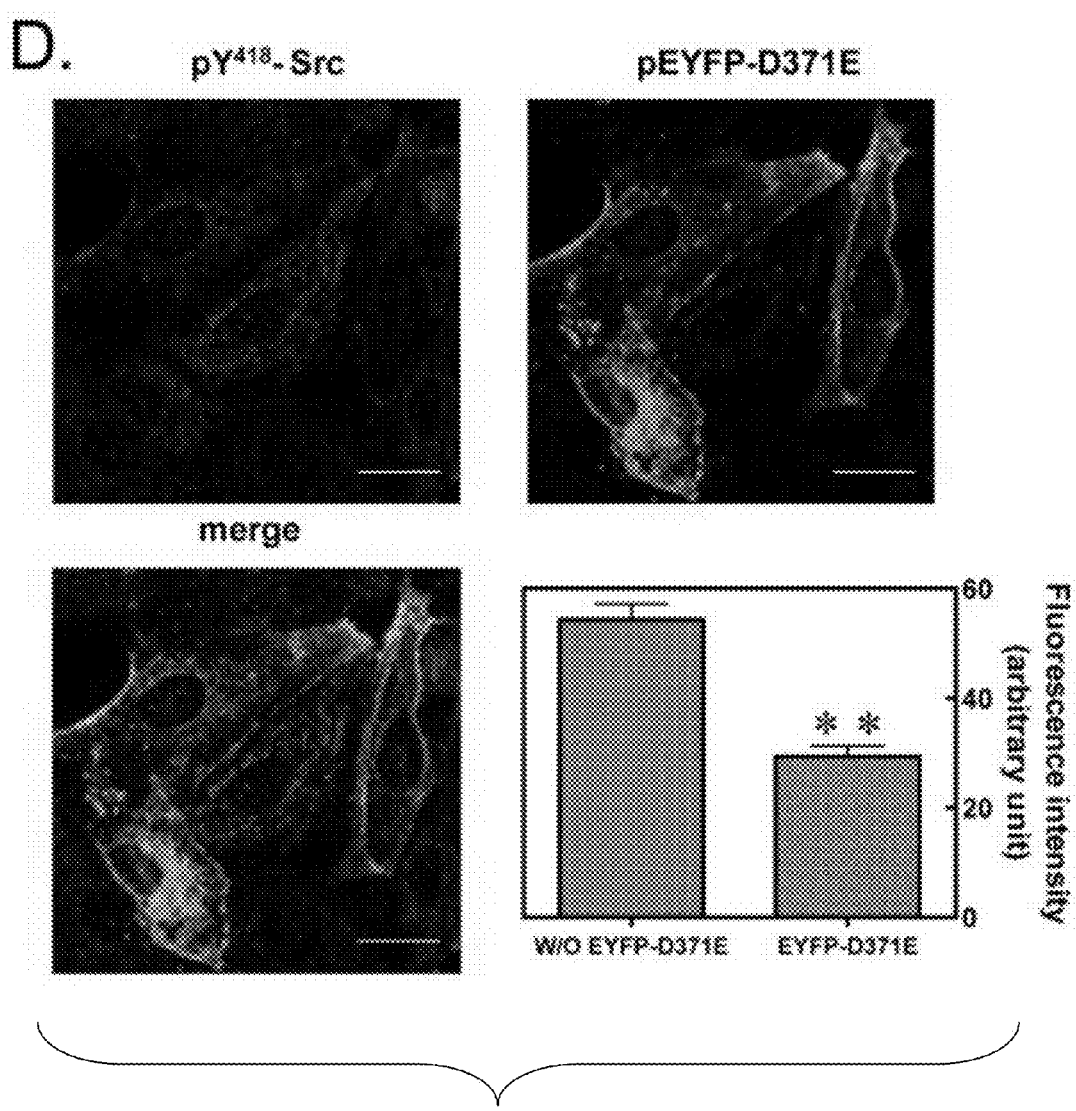

FIG. 15D. TCN23-19 cells were transiently transfected with a vector expressing EYFP-fused α1 D371E mutant (pEYFP-D371E). After 24 h, cells were serum-starved for 12 h and then immunostained with anti-Tyr(P)$^{418}$-Src antibody. Images from a representative experiment show that expression of mutant pEYFP-D371E reduced the intensity of red (Tyr(P)$^{418}$-Src) fluorescence (comparing the green and nearby non-green cells). The quantitative data of Tyr(P)$^{418}$-Src were collected from 40 different microscope vision fields in four independent experiments and expressed as mean± S.E. **, $p<0.01$. The scale bar represents 22 μm; W/O, without.

Figures 16A, 16B:
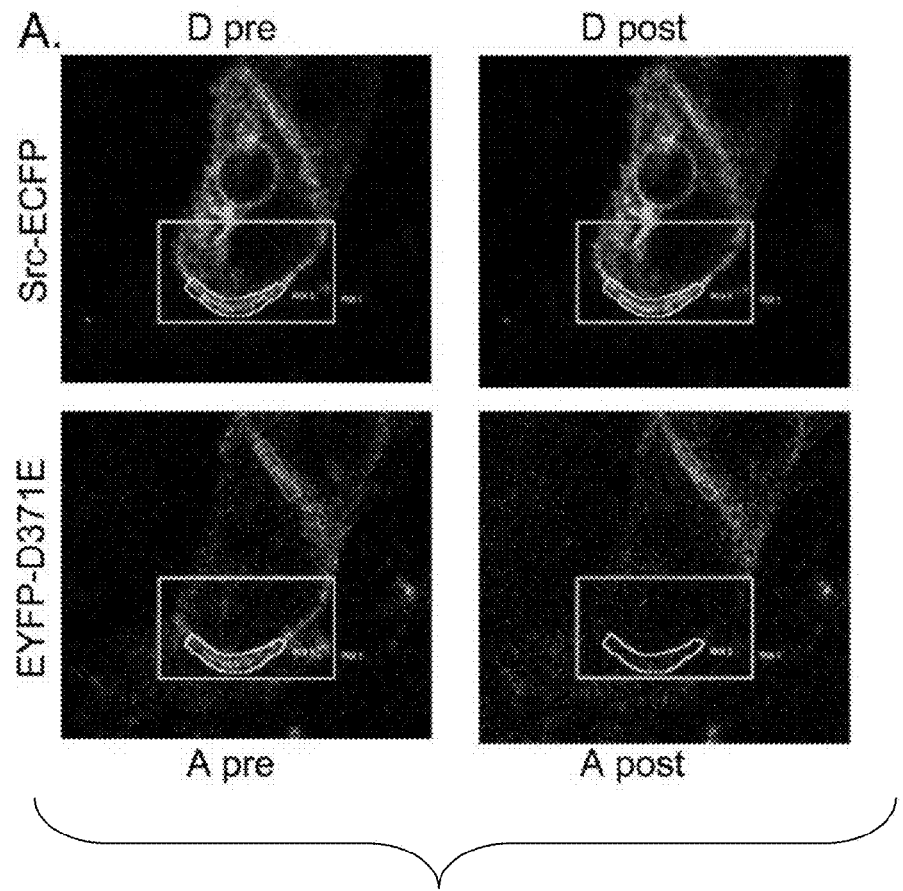

FIGS. 16A-B. Interaction between Src and the pumping-null Na+/K+-ATPase:

FIGS. 16A and 16B. TCN23-19 cells were co-transfected with Src-ECFP and EYFP-rat α1 mutant (D371E) expression vectors. After 24 h, FRET analysis was performed as described under "Experimental Procedures." Boxed ROI__1 (green) was photobleached, and the ROI$_{13}$ 3 (yellow) membrane area was analyzed for FRET. The boxed ROI__2 (purple) was selected and served as a non-bleaching control. The experiments were repeated three times, and a total of 20 cells were analyzed.

Figure 16C:
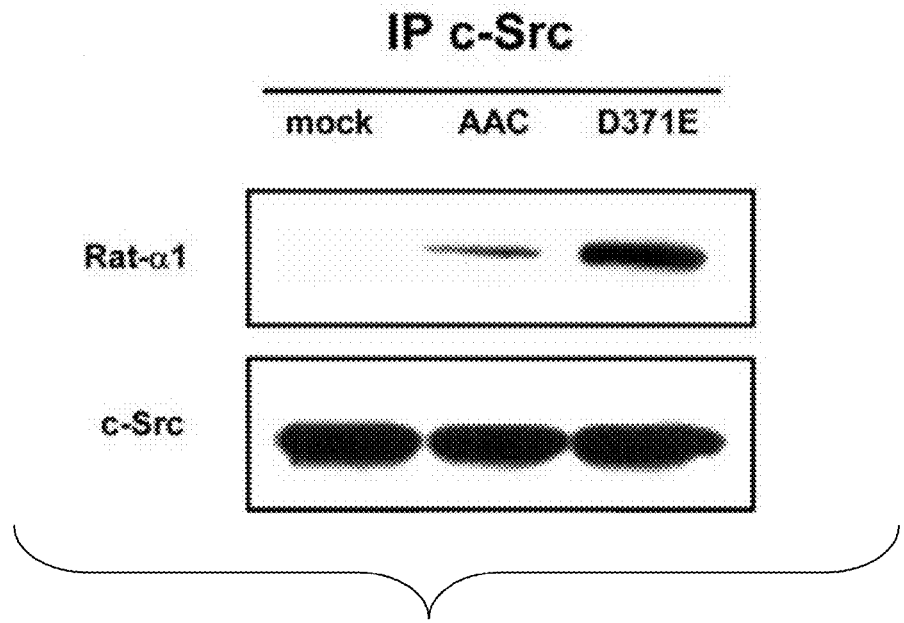

FIG. 16C. TCN23-19 cells were transiently transfected as in A with either silently mutated wild-type rat α1 (AAC) or rat α1 pumping-null mutant (D371E) expression vectors. After 36 h, cell lysates were prepared and subjected to immunoprecipitation using monoclonal anti-Src (clone GD11) antibody. Immunoprecipitates were then analyzed by Western blot using either anti-NASE antibody (for rat α1) or anti-c-Src (SRC2) antibody. The same experiments were repeated three times, and a representative Western blot is shown. IP, immunoprecipitate.

Figure 17A:
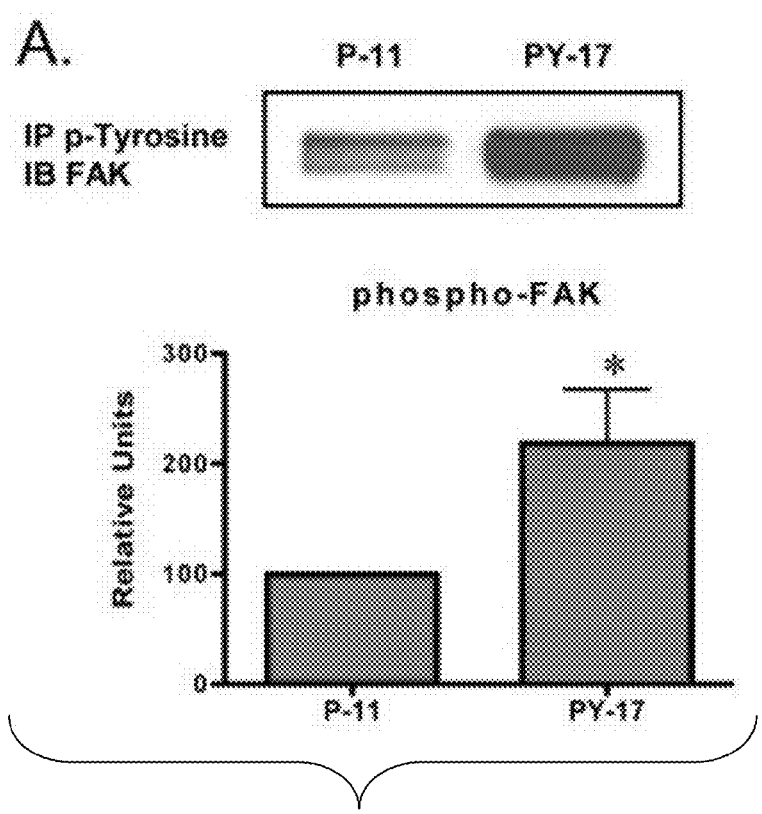

FIGS. 17A-E. Regulation of FAK phosphorylation by Src-interacting Na+/K+-ATPase:

FIG. 17A. Cultured P-11 and PY-17 cells were serum-starved for 12 h. Cell lysates were then immunoprecipitated using anti-phosphotyrosine antibody (4G10), and Immunoprecipitates were analyzed by anti-FAK antibody. The combined quantitative data were from three independent experiments.

Figure 17B:
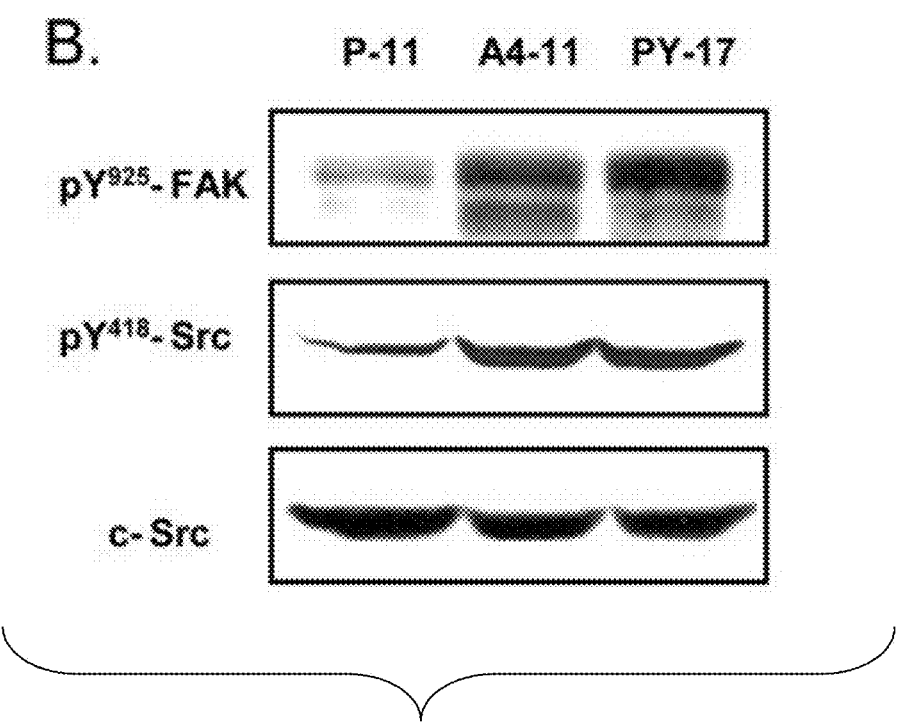

FIG. 17B. Cell lysates from different cell lines were separated by SDS-PAGE and analyzed by anti-Tyr(P)$^{925}$-FAK and anti-Tyr(P)$^{418}$-Src antibodies. The same membrane was striped and reprobed with anti-c-Src (B-12) antibody. A representative blot of three independent experiments is shown.

Figure 17C:
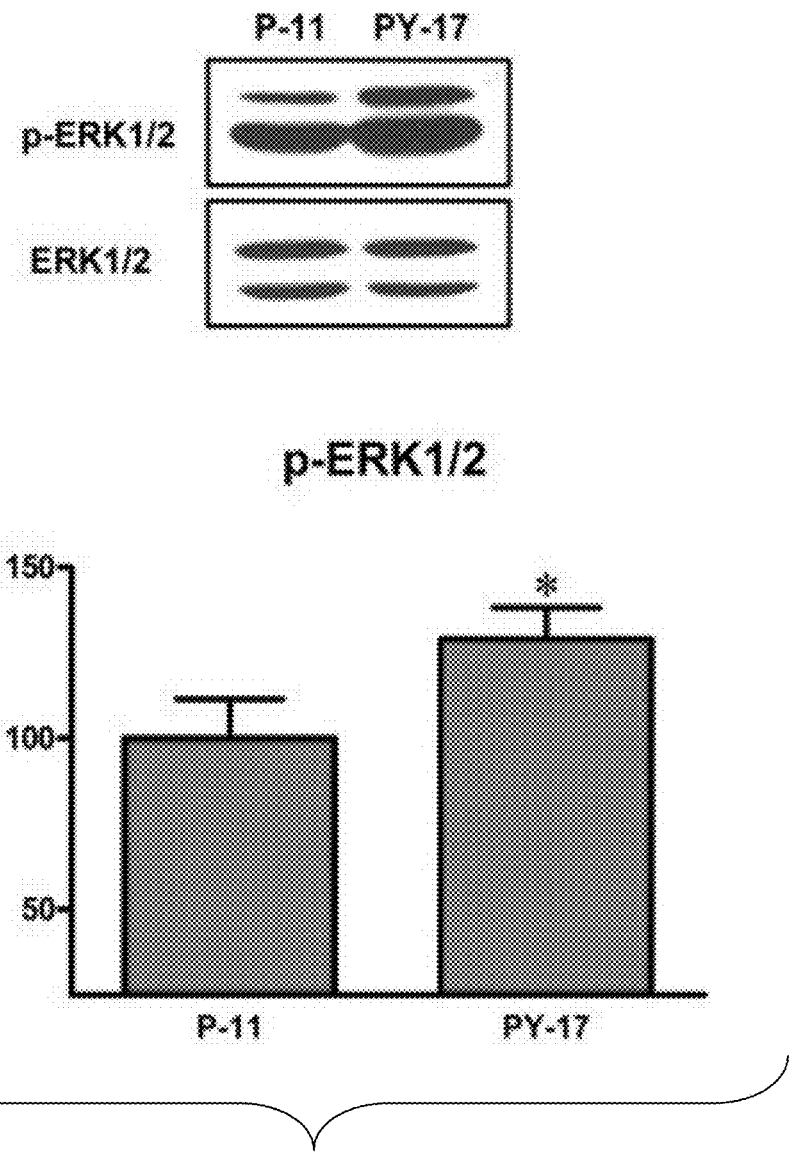

FIG. 17C. Cell lysates were analyzed by anti-pERK1/2 or anti-ERK1/2 antibody. The quantitative data (mean±S.E.) were calculated from four separate experiments as relative ratio of pERK/ERK.

Figure 17D:
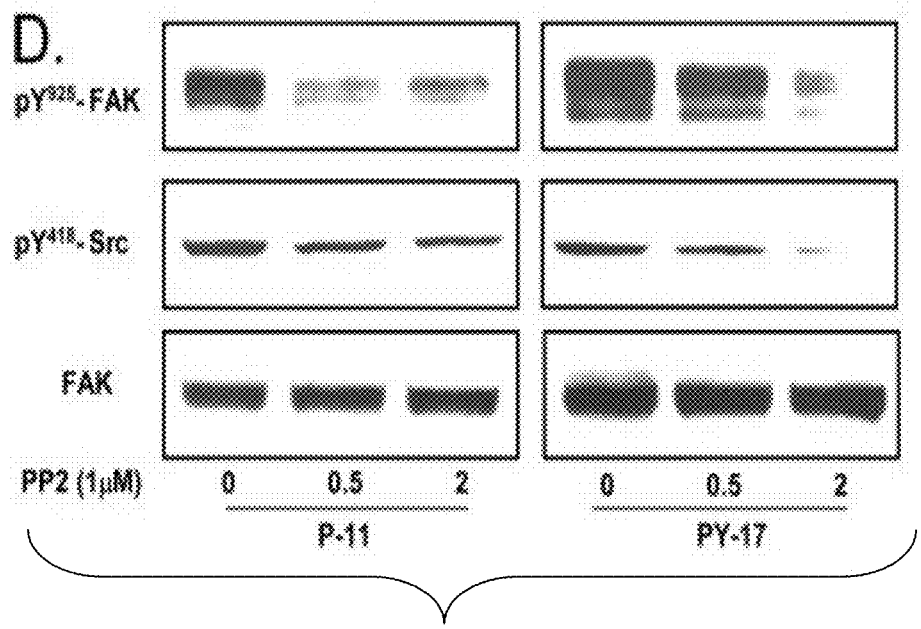

FIG. 17D. P-11 and PY-17 cells were treated with 1 μM PP2 for 0.5 and 2 h. FAK and Src activation was measured by using the specific antibodies. A representative Western blot is shown, and the same experiments were repeated three times.

Figure 17E:
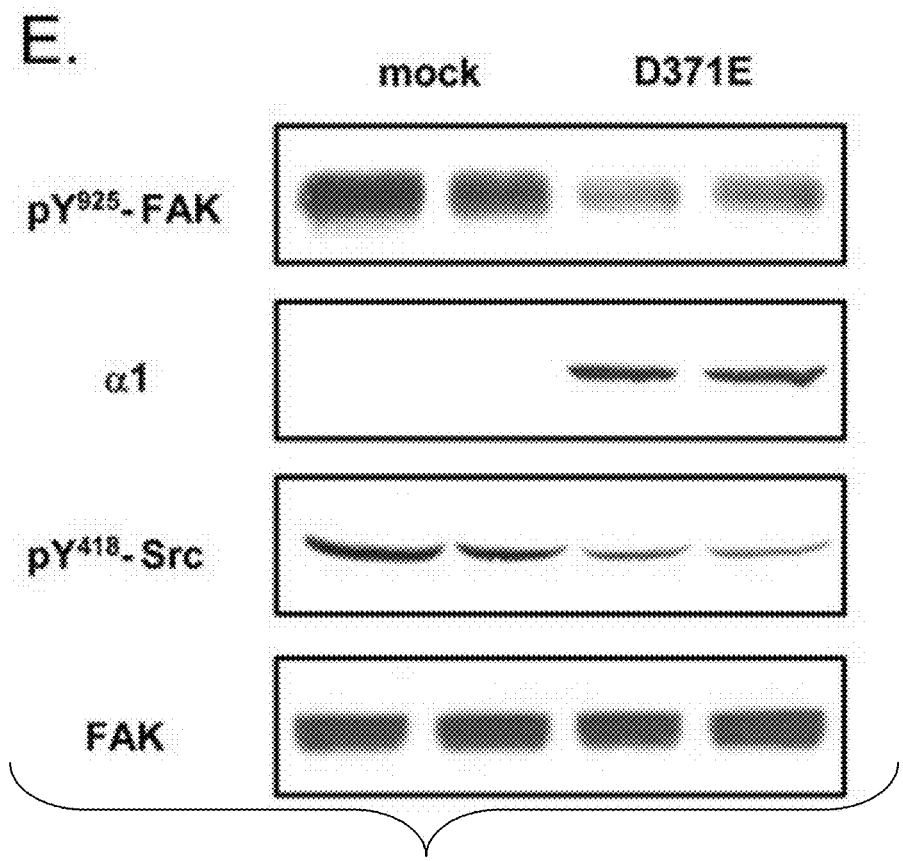

FIG. 17E. PY-17 cells were transiently transfected with either an empty vector (mock) or the D371E mutant. After 36 h, the transfected cells were lysed and analyzed by Western blot using specific antibodies as indicated. A representative Western blot is shown, and the same experiments were repeated three times. IP, immunoprecipitate; IB, immuno blot. *, $p<0.05$ versus P-11.

Figure 18A:
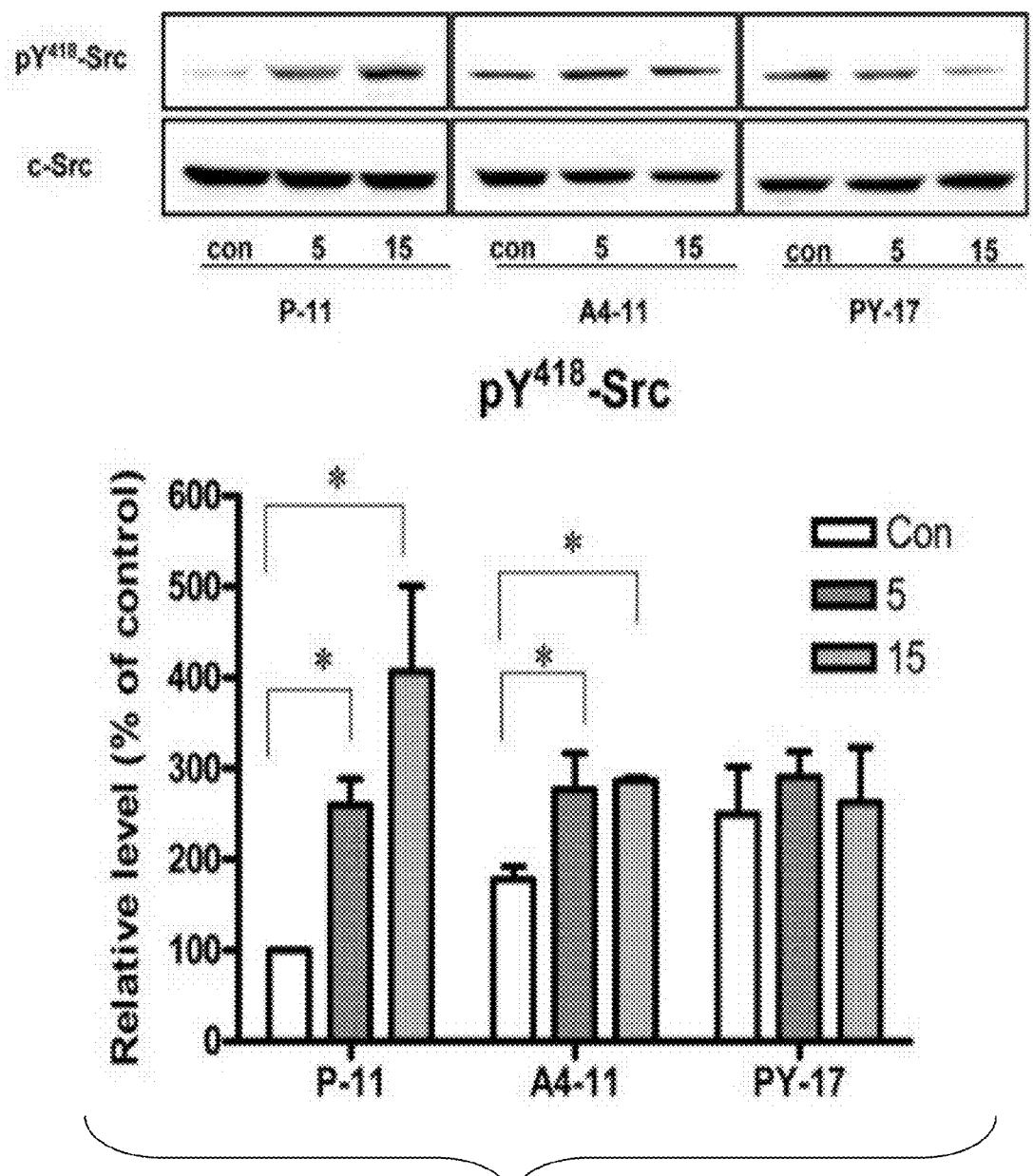
Figure 18B:
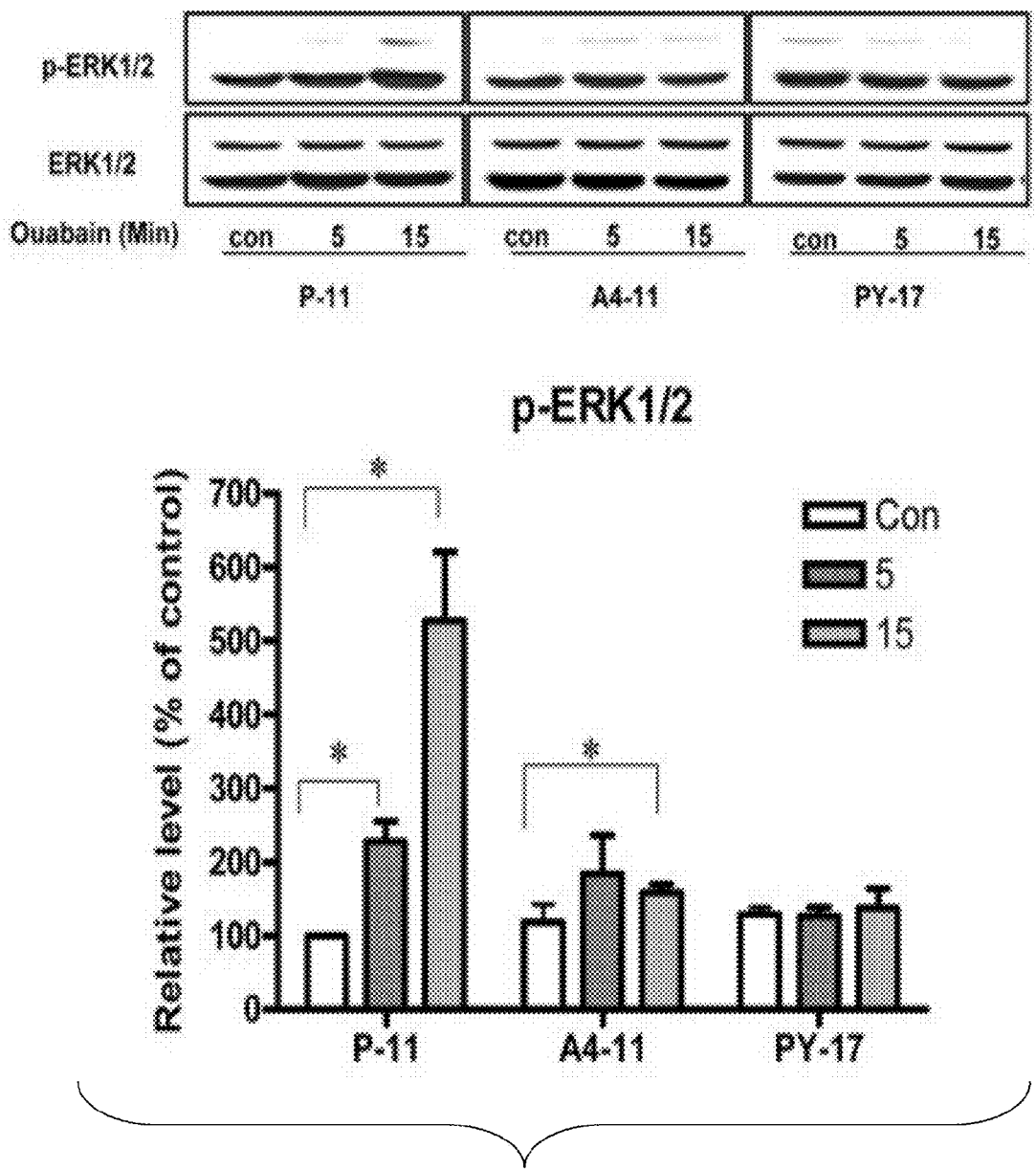
Figure 18C:
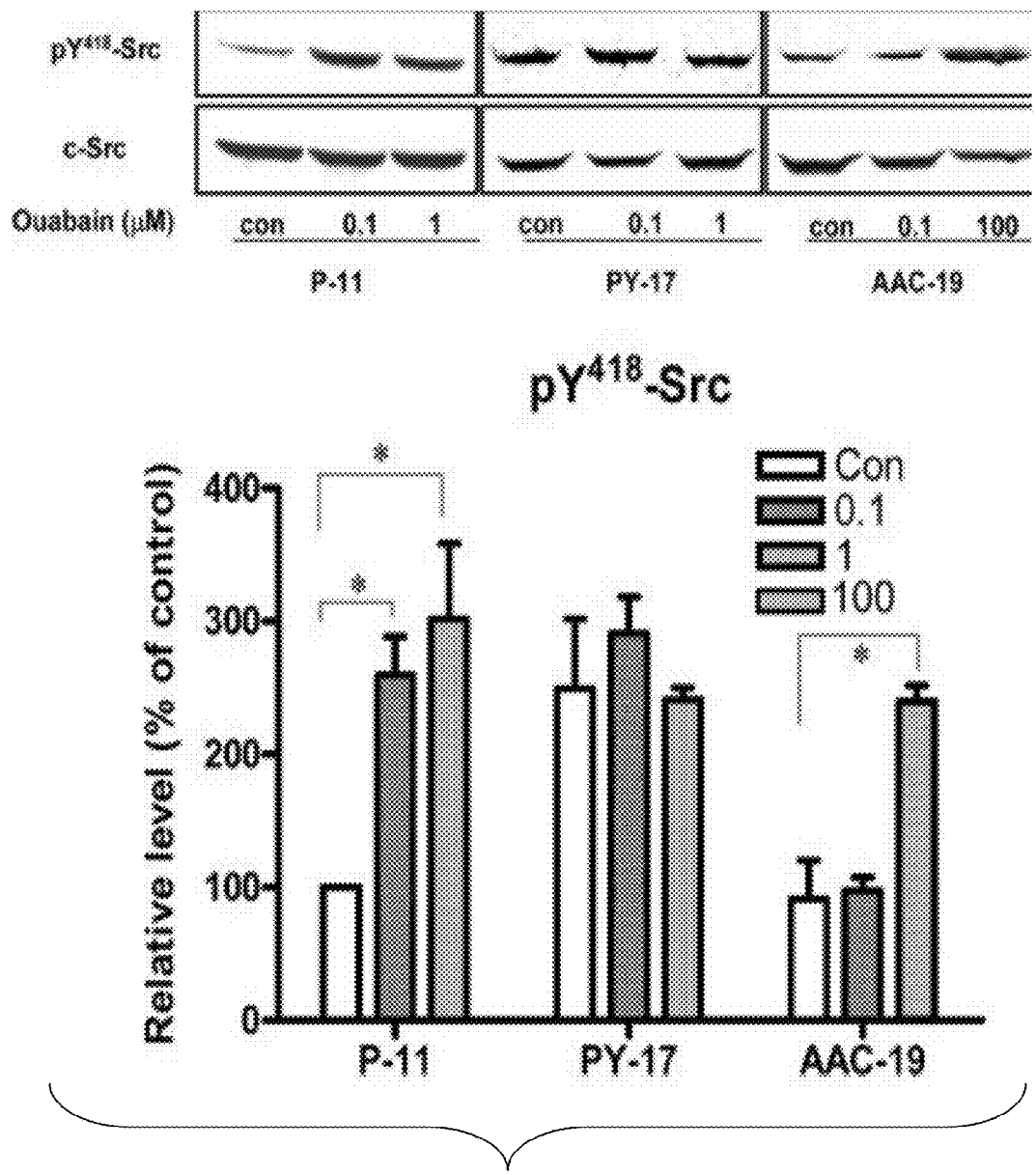
Figure 18D:
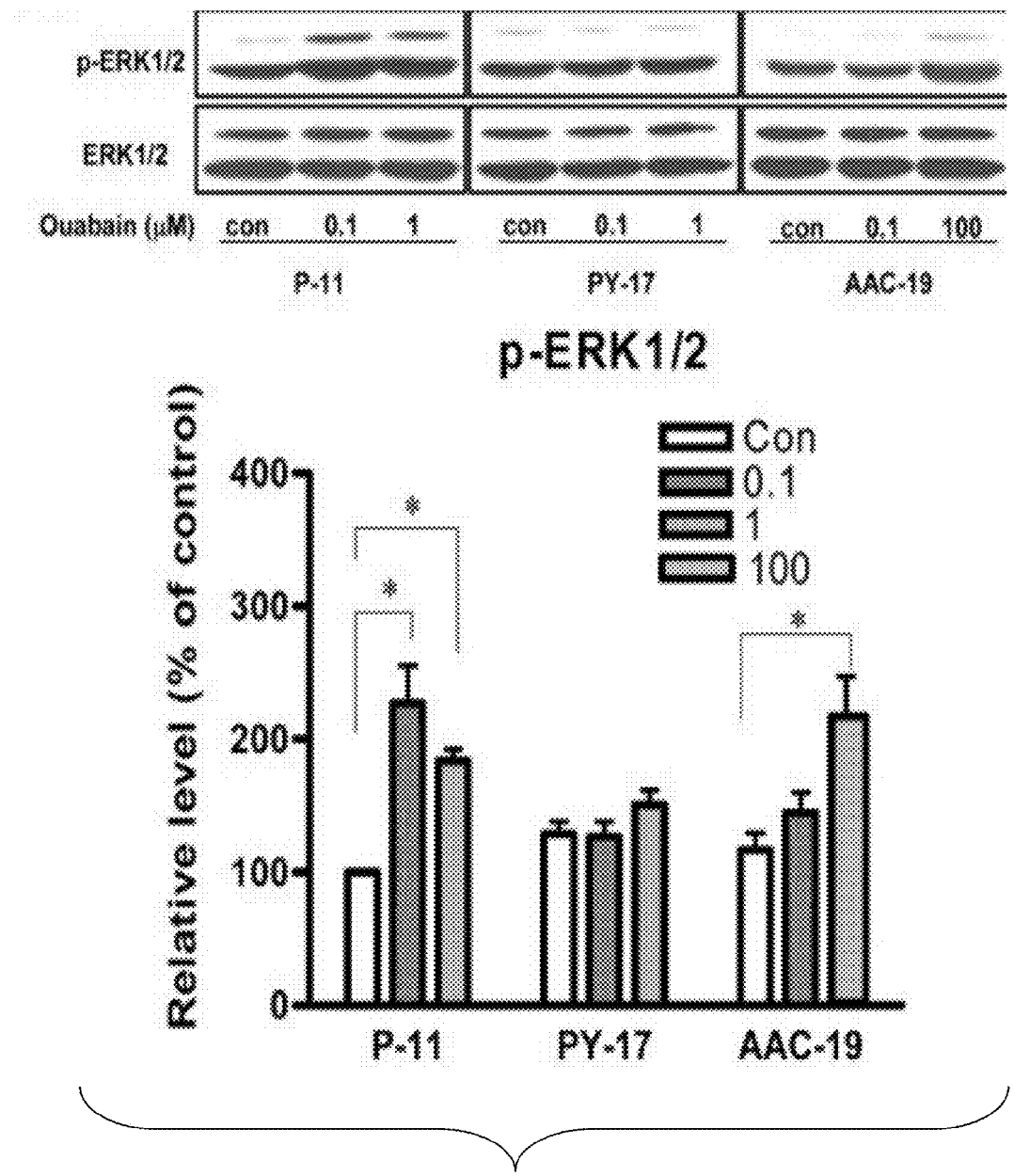

FIGS. 18A-D. Effects of ouabain on Src and ERK1/2:

FIGS. 18A and 18B. Cells were exposed to 100 nM ouabain for either 5 or 15 min, and the cell lysates (50 μg/lane) were analyzed by Western blot for active Src or active ERK1/2. Blots were probed first with anti-Tyr(P)$^{418}$-Src or anti-pERK antibody, then stripped, and reprobed for total Src or ERK1/2 to ensure equal loading.

FIGS. 18 C and 18D. Cells were treated with indicated concentrations of ouabain for 5 min, and total cell lysates were analyzed for Tyr (P)$^{418}$-Src and total Src or pERK1/2 and total ERK1/2 as in FIGS. 18A and 18B. A representative Western blot and combined quantitative data are shown. The quantitative data (relative ratio of pSrc/Src or pERK/ERK) from three independent experiments (mean±S.E.) were calculated relative to the control condition of P-11 cells. *, $p<0.05$ versus the respective control condition of each cell line. con, control.

FIGS. 19A-19D. Further mapping of specific domains in Na+/K+-ATPase that interact and inhibit Src:

FIG. 19A. Scheme of Na+/K+-ATPase α1 and CD3 domain.

FIG. 19B. Amino acid sequence of ND1 [SEQ ID NO: 1] [LTQNRMTVAHMWSDNQIHEADTTENQS-GVSFDKTSATWLALSRIAGLCNRAVFQA NQ].

FIG. 19C. In vitro binding assay using GST-tagged α1 truncations and His-Src.

Figure 19D:
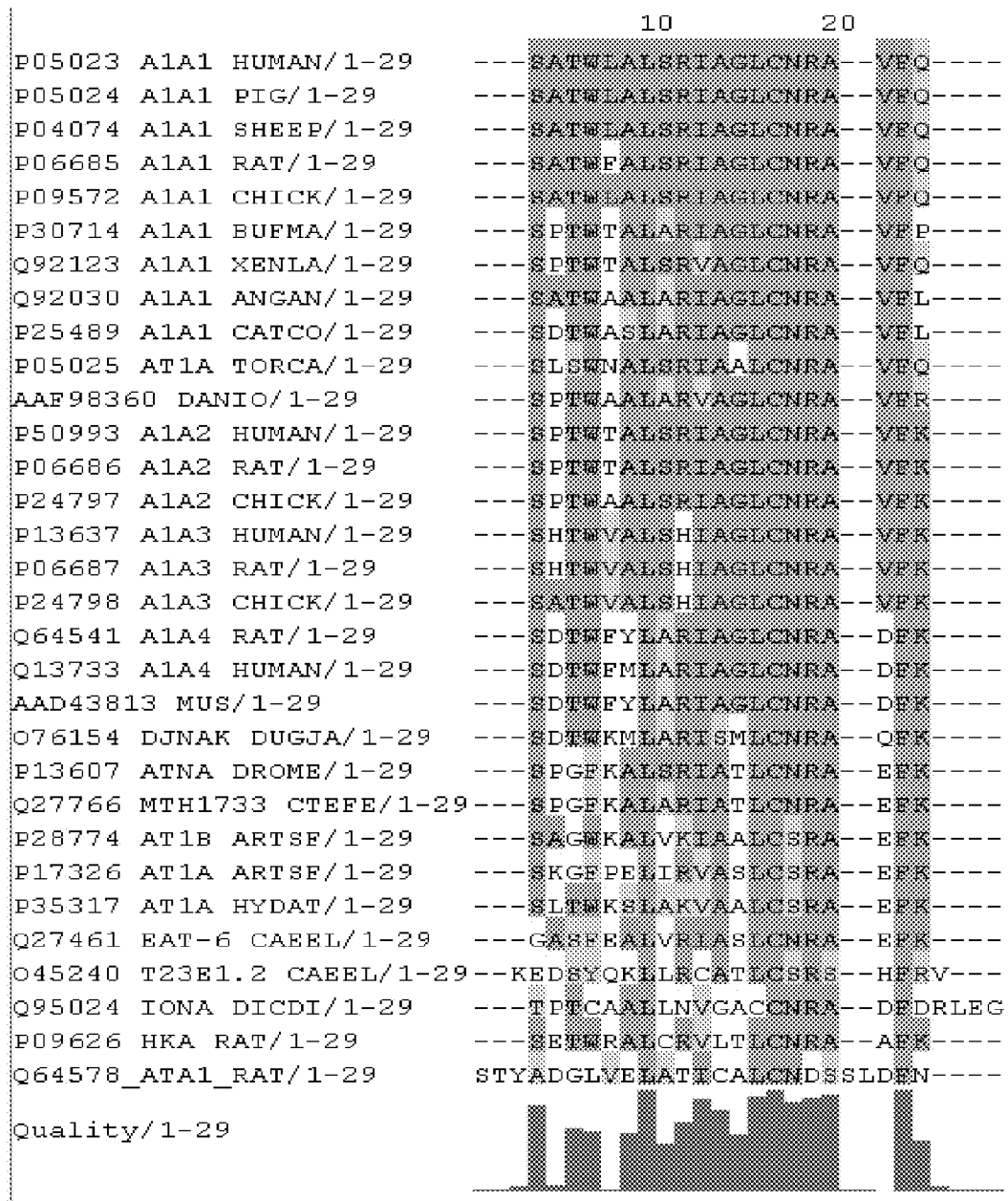

FIG. 19D. Sequences showing that ND1 peptide is conserved in different species and different isoforms of Na/K-ATPase (A part of sequence is shown and full length sequences can be obtained from Swiss Prot database according to the provided access No [SEQ ID NOS: 2-33].

FIGS. 20A-C. Further mapping of specific domains in Src that interact with Na+/K+-ATPase:

FIG. 20A. Schematic structure of Src and its kinase domain.

FIG. 20B. Amino acid sequence of KD1 [SEQ ID NO: 34] [LRLEVKLGQGCFGEVWMGTWNGTTR-VAIKTLKPGTMSPEAFLQEAQVMKKLRH E].

FIG. 20C. In vitro binding assay using GST-tagged Src truncations and purified Na+/K+-ATPase.

Figure 21:
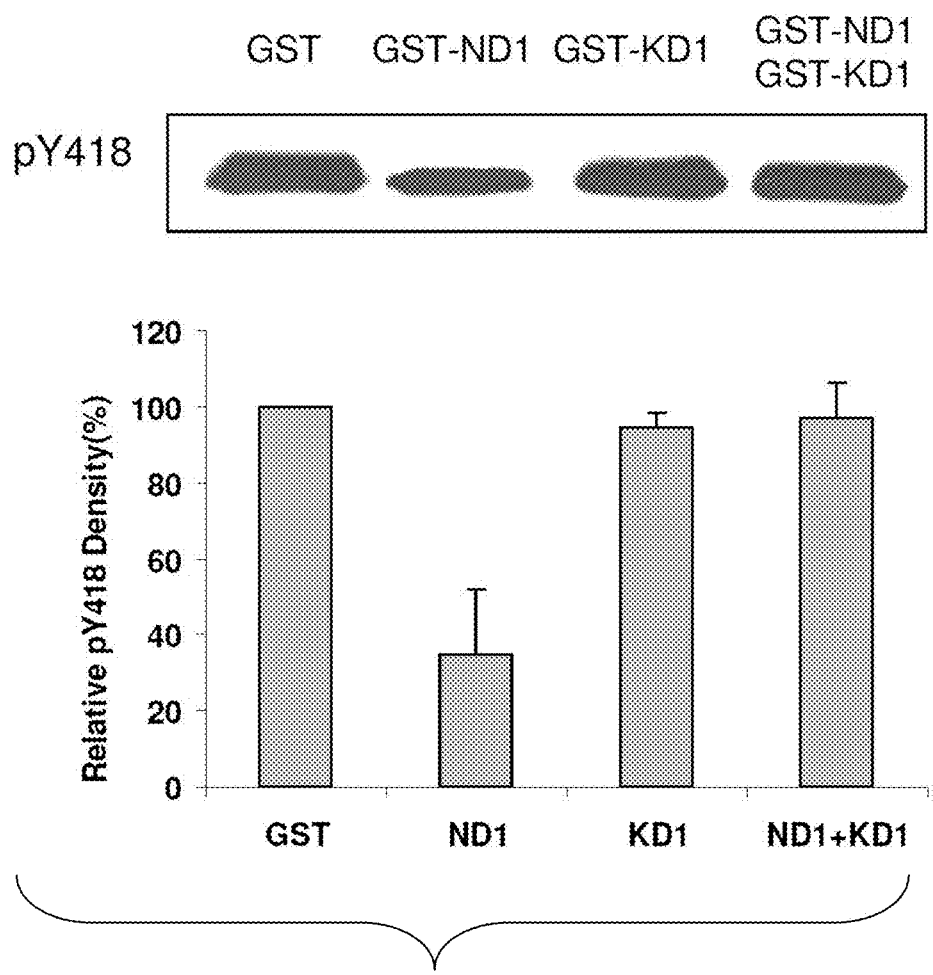

FIG. 21. Activity assay confirms that ND1 and KD1 are involved in Na+/K+-ATPase mediated regulation of Src.

Figure 22A:
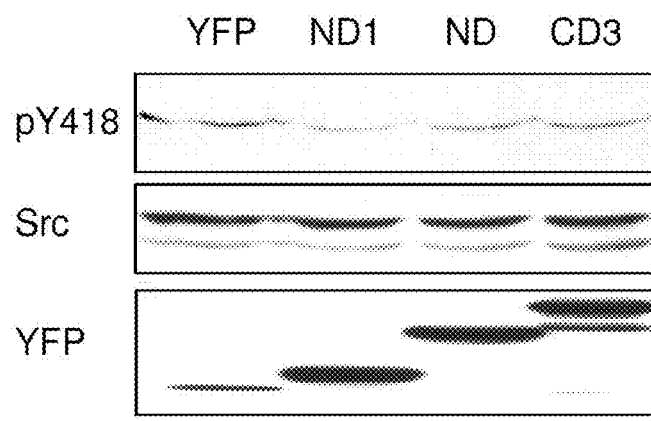
Figure 22B:
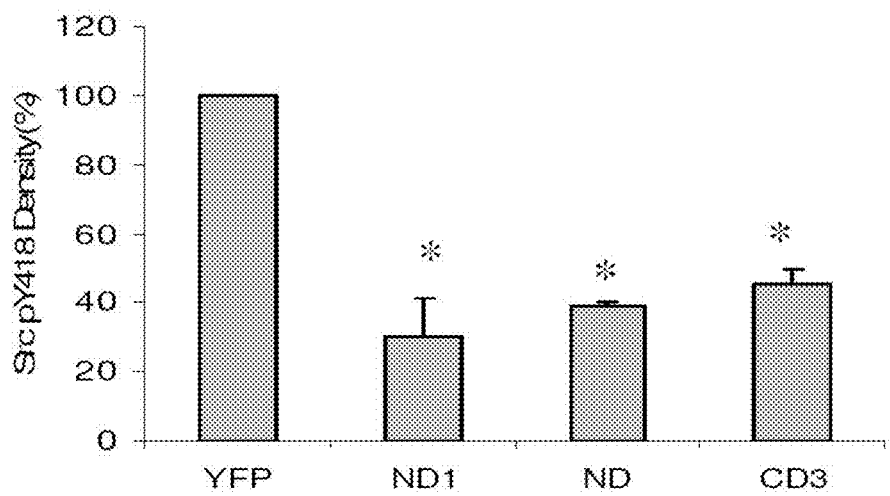

FIGS. 22A-B. ND1 is effective in blocking Src activity in live cells:

FIG. 22A. LLC-PK1 cells were transient-transfected with YFP-tagged ND1, ND, and CD3 for 24 h.

FIG. 22B. The quantitation data from three experiments. * p<0.05.

Figure 23:
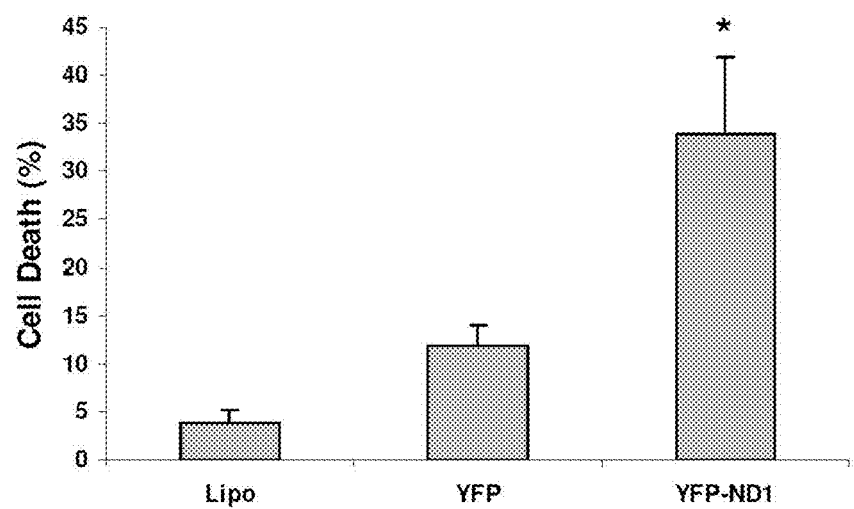

FIG. 23. YFP-ND1 inhibits human prostate cancer cell (DU145) growth.

Figure 24A:
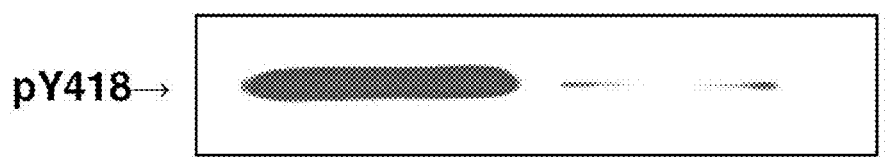
Figure 24B:
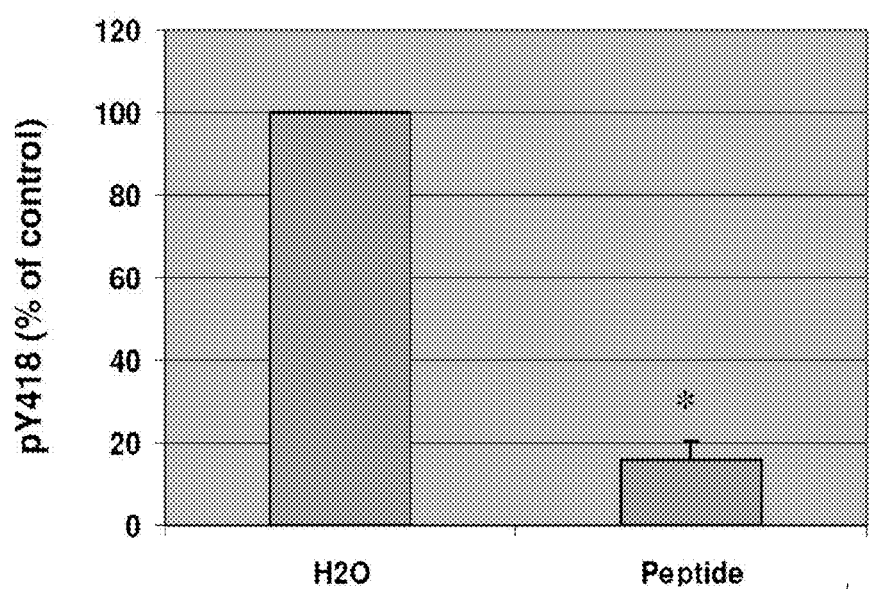

FIGS. 24A-24B. Mapping of a 20 amino acid peptide (P-3) from ND1 that inhibits Src:

FIG. 24A. Peptide sequence of P-3 [SEQ ID NO: 2] [SATWLALSRIAGLCNRAVFQ].

FIG. 24B. The results when purified Src was incubated with P-3 peptide at 37° C. for 20 min and 2 mM ATP was added for additional 5 min.

FIG. 25. Table 1—targets and oligo sequences of human Na+/K+-ATPase-α1 subunit-specific siRNAs where the target sequences are marked by bold letters, in order of listing where SEQ ID NOS:35-38 are the Target Sequence, and where SEQ ID NOS:39-46 are the Oligo inserts. (See FIG. 25—Table 4).

FIG. 26. Table 2—the relative α1 subunit protein content and the composition of DNA constructs used in difference cell lines.

FIG. 27. Table 3—Na+/K+-ATPase activity in different cell lines.

FIG. 28. Sequences of peptides penetratin (TAT) and helix of antennapedia (AP). [SEQ ID NOS: 47, 48].

FIGS. 29A-29D. TAT-P3 and AP-P3 inhibit Src and block DU145 cell growth.

Figure 29B:
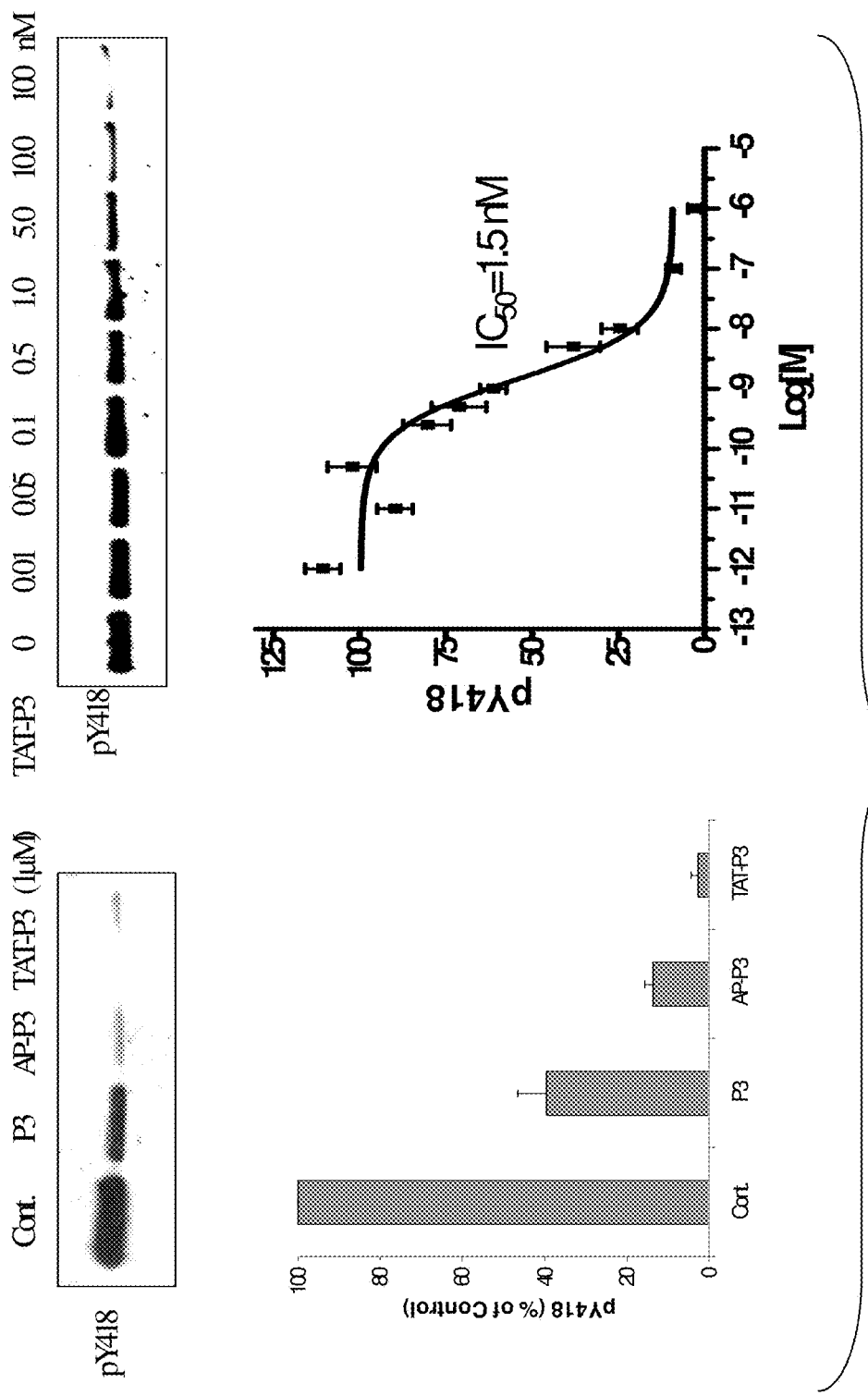

FIG. 29A shows the sequences of TAT or AP-tagged Src peptide inhibitors (TAT-P3 or AP-P3). [SEQ ID NOS: 49, 50]:

FIG. 29B shows that the new peptides inhibit Src in vitro.

FIG. 29C shows that a FITC-conjugated TAT-P3 is targeted to the cell membrane.

FIG. 29D shows that addition of TAT-P3 or AP-P3 to DU145 cells inhibited cell growth.

FIGS. 30A-B shows a table with the SEQ ID NOS: 1-55.

DETAILED DESCRIPTION OF THE PREFERRED EMBODIMENT

Src and Src family kinases are non-receptor tyrosine kinases that play an important role in regulation of various signaling pathways involved in control of cell growth, mobility, and muscle contraction. Moreover, our recent studies have shown that activation of Na/K-ATPase-associated Src by cardiotonic steroids protects the heart from ischemia/reperfusion injury. It also inhibits cancer cell growth and stimulates collagen synthesis in fibroblasts. Because Src family kinases are highly active in many types of cancer, pharmaceutical companies are interested in developing specific Src and Src-family kinase inhibitors. Most of the developed inhibitors are ATP analogs that directly compete with ATP.

In one aspect, the present invention relates to peptide Src inhibitors that include Na+/K+-ATPase which binds and inhibits Src. The peptide inhibitors not only act via a different mechanism from the ATP analogues, but also are pathway (Na+/K+-ATPase) specific. Thus, these peptides are useful for the development of effective therapeutics for cancer and other diseases in which Src or Na+/K+-ATPase/Src activity is abnormal. In addition, this invention relates to peptide Src activators that include a Src fragment which binds and prevents the Na+/K+-ATPase from inhibiting Src. Like cardiotonic steroids, these peptide activators can activate the Na+/K+-ATPase-associated Src. In contrast to cardiotonic steroids, they do not inhibit the pumping function of Na+/K+-ATPase. Thus, these activators are useful for the development of effective therapeutics for congestive heart failure, ischemia/reperfusion injury (e.g. myocardial infarction) and other diseases in which Src or Na+/K+-ATPase/Src activity is abnormal.

Cardiotonic steroids such as ouabain activates Src, resulting in protein tyrosine phosphorylation in many different types of cells. The inventors have now discovered that Src and the Na+/K+-ATPase interact via multiple domains to form a functional receptor complex. This interaction effectively keeps Src in an inactive state, indicating that the Na+/K+-ATPase is an effective Src inhibitor.

Since Na+/K+-ATPase, as a newly discovered signal transducer, mediates several signaling pathways that relate with cancer cell growth, cardiac fibrosis, ischemia/reperfusion injury and uremic cardiomyopathy, the inventors herein have now discovered that interfering of such interaction between Na+/K+-ATPase and Src provides useful treatment information for these diseases.

Detailed mapping of the functional domains in both Src and the Na+/K+-ATPase alpha 1 subunit reveals that the Na+/K+-ATPase-mediated inhibition of Src is due to the interaction between the N domain, Specifically the ND1 peptide, of the alpha subunit and the Src kinase domain, specifically the KD1 peptide.

Further analysis reveals that a 20 amino acid peptide (P-3) derived from ND1 is sufficient to bind and inhibit Src activity as well as other Src family kinases such as Lyn. Moreover, when a cell-penetrating peptide (e.g. TAT or AP) is attached to the Src-inhibitory peptide, this new peptide is fully capable of entering cells and inhibiting cellular Src activity. When tested in prostate cancer DU145 cells, these tagged peptide inhibitors are effective in blocking DU145 cell proliferation. The inventors also found that the KD1 derived from the Src kinase domain could bind with Na+/K+-ATPase and was effective in activating the Na+/K+-ATPase-inhibited Src by competing the binding motif for Src.

Thus, the inventors have developed peptides that are useful to either activate or inhibit Na+/K+-ATPase pathway-specific Src or Src family kinases. Moreover, the inventors have identified an interacting site (i.e. between the ND1 of subunits and KD1 of Src) that can be used as a target for developing other peptide and small molecule inhibitors or activators that are more potent, tissue specific or have better pharmacodynamic or pharmacokinetic properties.

In another aspect, the peptides represent new classes of Src inhibitors and/or activators. Because these peptides target the region that specifically interact with Na+/K+-ATPase other than generically competing for ATP binding, they are more specific and have less cross-reactivity with receptor tyrosine kinases. In addition, these peptides provide a pathway-specific modulation of Src activity, thus more narrowly (specifically) targeted. Furthermore, structure-functional studies will produce a more potent and specific inhibitor/activator for individual Src family kinases since each has different KD1 sequence. Since other alpha subunits of Na+/K+-ATPase also bind the kinase domain, it is possible to develop isoform-specific Src inhibitors. Finally, using the structural information, it is now possible to develop small molecules that have better pharmacokinetical and pharmacodynamical properties.

Sequence-based analysis of the Src inhibitor peptides or crystallization of the identified interacting domains may reveal the exact interface between Src and the Na+/K+-ATPase, which shall allow the development of new peptides or small molecules to either inhibit or activate Src. Using the identified interaction (the Na+/K+-ATPase/Src interaction or the subunit N domain/Src kinase domain interaction), a rapid screen assay can be developed for large scale and high out-put screen of additional peptides and small molecules. Genetic methods or chemicals or hormones could be used to either up or down regulate cellular Na+/K+-ATPases, thus inhibiting or activating cellular Src or Src family kinases.

In another aspect, the discovered Na+/K+-ATPase/Src receptor complex serves as a target for developing new agonists and antagonists of this receptor.

EXAMPLE I

Binding of Src to Na+/K+-ATPase Forms a Functional Signaling Complex

The Na+/K+-ATPase interacts with Src to form a functional signaling complex.

Materials And Methods

PP2, a Src kinase inhibitor, was obtained from Calbiochem (San Diego, Calif.). [γ-32P]ATP was obtained from New England Nuclear (Boston, Mass.). The antibodies used and their sources were as follows: The monoclonal anti-phosphotyrosine antibody (PY99), the monoclonal anti-Src antibody (B12), the goat anti-rabbit and the goat anti-mouse secondary antibodies were obtained from Santa Cruz Biotechnology (Santa Cruz, Calif.). The polyclonal anti-Src pY418 antibody and anti-Src pY529 were from Biosource International (Camarillo, Calif.). The monoclonal anti-His antibody was from Invitrogen (Carlsbad, Calif.). Purified recombinant Src and the assay kit for Src kinase activity, anti-phosphotyrosine antibody, and protein G Agarose were obtained from Upstate Biotechnology (Lake Placid, N.Y.). Plasmids pGFP2-C, pRluc-N, and DeepBlueC were purchased from Biosignal Packard (Montreal, Canada). Plasmids pEYFP-C1 and pECFP-N1 were purchased from Clontech (Palo Alto, Calif.), and pGEX-4T-1 and pTrc-His were from Invitrogen. All secondary antibodies were conjugated to horseradish peroxidase; therefore, the immunoreactive bands were developed using chemiluminescence (Pierce, Rockford, Ill.). Glutathione beads were from Amersham Bioscience (Uppsala, Sweden). The Optitran nitrocellulose membranes were obtained from Schleicher & Schuell (Keene, N.H.).

Plasmid Constructs

Figure 3A:
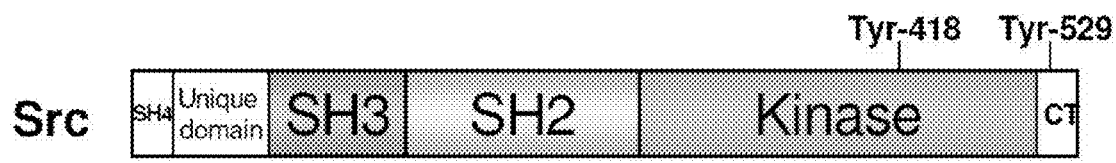
FIGS. 3A-C. Identification of the Src domains involved in the interaction with the Na+/K+-ATPase.
Figure 3B:
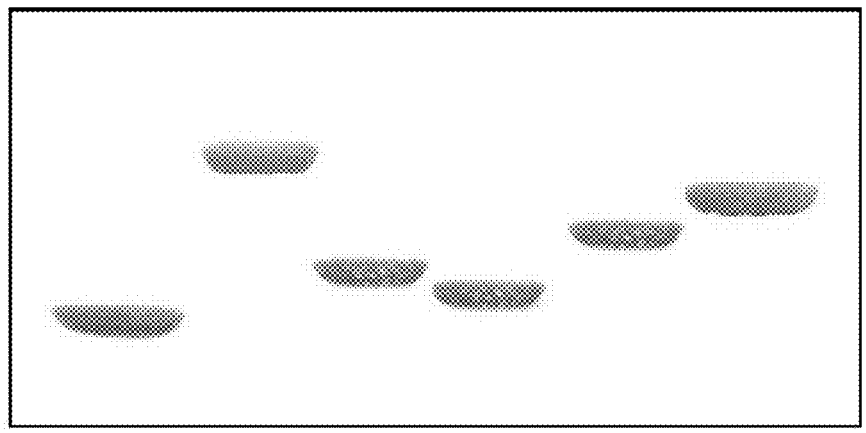

The preparation of chicken c-Src lacking the SH4 domain and GST-Src mutants were done (Ma et al., 2000). GST-NT (amino acid residue 6-90) [SEQ ID NO: 51], GST-CD2 (amino acid residue 152-288) [SEQ ID NO 52], and GST-CD3 (amino acid residue 350-785) [SEQ ID NO: 53] expression vectors were constructed based on the sequence of pig kidney Na+/K+-ATPase α1 subunit (see FIG. 3A).

GST-H+/K+-CD3 [SEQ ID NO: 54] and GST-SERCA-CD3 [SEQ ID NO: 55] were constructed based on the rat H+/K+-ATPase cDNA and rat cardiac SERCA 2a cDNA, respectively. His-tagged Src constructs were generated by excising the corresponding Src cDNA from the GST-Src vectors and then inserting them into pTrc-His A vector. Src-ECFP and Src-Rluc for fluorescence resonance energy transfer (FRET) and bioluminescence resonance energy transfer (BRET) assays were constructed by cloning the full-length c-Src in frame into pECFP-N1 or pRluc vector. The rat Na+/K+-ATPase α1 cDNA was excised from the expression vector provided by Dr. Pressley (Texas Tech University) and inserted in frame into pEYFP-C1, and the canine Na+/K+-ATPase α1 cDNA was cloned into pGFP2 vectors. All constructs were verified by DNA sequencing.

Cell Preparation, Culture, and Transient Transfection

Pig kidney proximal LLC-PK1, human embryo kidney 293T cells, and mouse fibroblast SYF and SYF+Src cells were obtained from American Type Culture Collection (Manassas, Va.) and cultured in DMEM medium containing 10% fetal bovine serum (FBS) and penicillin (100 U/ml)/streptomycin (100 gg/ml). LLC-PK1 cells and 293T cells were serum-starved for 24 h, whereas SYF and SYF+Src cells were cultured in the medium containing 0.5% FBS for 24 h and used for the experiments. Cells were transfected with various plasmids using Lipofectamine 2000 (Wang et al., 2004). Experiments were performed 24 h after transfection unless indicated otherwise.

Preparation of Src, Na+/K+-ATPase, GST-Fused Proteins, and His-Tagged Proteins

Src, without the first 85 amino acid residues, was purified from sf-9 cells as described (Ma et al., 2000) and used in the initial binding assays to ensure that Src binds to the Na+/K+-ATPase, but not the lipid composition in the purified Na+/K+-ATPase preparation. In subsequent experiments (e.g., phosphorylation and activity assays), purified recombinant full-length Src from Upstate Biotechnology was used. Na+/K+-ATPase was purified from pig kidney outer medulla using the Jorgensen method (Xie et al., 1996) and the preparations with specific activities between 1200 and 1400 μmol Pi/mg/h were used.

Under our experimental conditions either 100 μM vanadate or 10 μM ouabain caused a complete inhibition of the ATPase activity of the purified pig kidney Na+/K+-ATPase. GST fusion proteins or His-tagged proteins were expressed in *Escherichia coli* BL21 and purified on glutathione beads or nickel column.

Immunoprecipitation and GST Pulldown

Cells were lysed in RIPA buffer containing 1% Nonidet P40, 0.25% sodium deoxycholate, 150 mM NaCl, 1 mM EDTA, 1 mM phenylmethylsulfonyl fluoride, 1 mM sodium orthovanadate, 1 mM NaF, 10 μg/ml aprotinin, 10 μg/ml leupeptin, and 50 mM Tris-HCl (pH 7.4). Cell lysates were cleared by centrifugation at 16,000×g for 15 min, and the supernatants (1 mg) were either immunoprecipitated with anti-α1 antibody or incubated with different GST-fusion proteins. The complexes were then pulled down by either protein G agarose or glutathione beads (Ma et al., 2000; Haas et al., 2002) and analyzed by Western blot.

Src Kinase Activity

The Src kinase activity was assayed using a commercial kit (Haas et al., 2000). To determine how Na+/K+-ATPase affects Src kinase activity, the purified Src (4.5 U) was incubated with 5 μg of the purified Na+/K+-ATPase in the Src assay buffer for 30 min at room temperature. Afterward, both control Src or the Na+/K+-ATPase-bound Src were exposed to 10 μM ouabain and Src kinase activity was determined. In other experiments, the Src pY418 was measured by anti-pY418 antibody to indicate Src activation (Ma et al., 2000). To do so, the purified Src (4.5 U) was incubated with different amounts of the purified Na+/K+-ATPase or GST-Na+/K+ ATPase constructs in phosphate-buffered saline (PBS) for 30 min at 37° C. Afterward, 2 mM ATP/Mg2+ was added. The reaction continued for 5 min at 37° C. and was stopped by addition of SDS sample buffer.

In Vitro Binding Assay

The purified Na+/K+-ATPase was solubilized in 1% Triton X-100 PBS and centrifuged at 100,000×g for 30 min. The supernatant was collected for the binding assay. GST-fusion proteins (5 μg) were conjugated on glutathione beads and incubated with the solubilized Na+/K+-ATPase in 500 μl PBS in the presence of 0.5% Triton X-100 at room temperature for 30 min. The beads were washed with the same buffer for four times. The bound Na+/K+ ATPase was resolved on 10% SDS-PAGE and detected by Western blot. Reciprocal binding assay using GST-Na+/K+-ATPase constructs (5 μg) and purified Src lacking of first 85 amino acids (200 ng) or His-tagged Src constructs (100 ng) was done similarly. To test if native Na+/K+-ATPase binds Src, the above experiments were repeated in the absence of Triton X-100. To make the Na+/K+-ATPase/Src complex, 2-5 μg of the purified Na+/K+ ATPase was incubated with 4.5 U of Src (~10 ng) in PBS in the absence of Triton X-100 at room temperature for 30 min. The complex was either used for the experiments directly as indicated or collected by centrifugation at 100,000×g for 30 min. Control experiments showed that the Na+/K+ ATPase-bound, but not the free, Src could be copelleted by the centrifugation.

FRET Analysis by Acceptor Photobleaching

Using pECFP-N1 and pEYFP-C1 vectors described above, the enhanced cyan fluorescent protein (ECFP) was fused to the C-terminus of Src, and the enhanced yellow fluorescent protein (EYFP) was fused to the N-terminus of rat Na+/K+-ATPase α1 subunit. Src-ECFP and EYFP-rat α1 plasmids were then cotransfected into LLC-PK1 cells. Cells transfected with either ECFP/EYFP or ECFP/EYFP-rat α1 were used as a control. After 24 h, cells growing on the glass coverslip were fixed with ice-cold methanol for 15 min at −20° C. and washed twice with PBS solution. The coverslip was then used for FRET measurement with a Leica DMIRE2 confocal microscope (Wetzlar, Germany). The laser lines of 456 nm and 515 nm were used to illuminate fluorescence, and the emission intensities were recorded at 465-509 nm for Src-ECFP and 530-570 nm for EYFP-rat α1. The cell that expresses both Src-ECFP and EYFPrat α1 was chosen to perform the FRET analysis. A membrane region of interest (ROI 1) was selected and photobleached by applying 100% intensity of 515-nm laser. The emission intensities of Src-ECFP and EYFP-rat α1 before and after the photobleaching process in the selected ROI 1 region were used to calculate the FRET efficiency. The FRET efficiency was also calculated at a nonphotobleached region (ROI 2) and used as a control.

FRET Analysis in Live Cells

LLC-PK1 cells were cotransfected with Src-ECFP and EYFP-rat α1 and grown on a glass coverslip for 24 h. The coverslip was then mounted in a metal chamber and analyzed with a Leica DMIRE2 confocal microscope. The laser lines of 456 nm and 515 nm were used to illuminate fluorescence, and the emission intensities were recorded at 465-509 nm for Src-ECFP and 530-570 nm for EYFP-rat α1. The cell that expresses both Src-ECFP and EYFP-rat α1 was chosen and illuminated by only 456-nm laser. The cells express only Src-ECFP or EYFP-rat α1 were used for correction and determination of the laser intensity as well as the gain and offset settings. The emission intensities for both Src-ECFP and EYFP-rat α1 in selected membrane region was recorded at 465-509 nm ($F_{ECFP}$) and 530-570 nm ($F_{EYFP}$), respectively. The FRET efficiency was reflected by the ratio of $F_{EYFP}/F_{ECFP}$. After 50 s of recording, the same cell was exposed to ouabain and the recording was continued for indicated time.

BRET Analysis

BRET assay was done as described by Lowry et al. (2002). Briefly, 24 h after transfection with GFP-Na+/K+-ATPase and Src-Rluc or other constructs as indicated, cells were seeded in triplicate in a 96-well microplate. After treatment with indicated concentration of ouabain, cells were exposed to equal volume of BRET analysis buffer containing 10 μM DeepBlue C, the substrate of Rluc. The emission at 410 nm (for Rluc) and 515 nm (for GFP) was immediately acquired using a Fluoroskan Ascent FL (Labsystems, Franklin, Mass.) with microplate luminometric detection. The BRET ratio was calculated as follows: (Emission at 515 nm−Background at 515 nm)/(Emission at 410 nm−Background at 410 nm), where Background signal was assessed in each experiment by measuring the signal of a sample of nontransfected cells.

Colocalization Analysis

LLC-PK1 cells were cultured for 24 h on glass coverslips, briefly washed twice with PBS, and then fixed with ice-cold methanol for 15 min. The cells were washed again with PBS and blocked using SignalEnhancer (Molecular Probes). Rabbit polyclonal anti-Src antibody and monoclonal anti-Na+/K+ ATPase antibody were mixed in 3% BSA and incubated with the coverslip overnight at 4° C. After three washes with PBS, Alexa fluor 546-conjugated anti-mouse antibody and Alexa fluor 488-conjugated anti-rabbit antibody were added and incubated for 1 h at room temperature. The coverslip was washed again with PBS for three times. The Na+/K+-ATPase was visualized by excitation at 546 nm and emission at 566-620 nm. Src was visualized by excitation at 488 nm and emission at 505-535 nm. To avoid the crosstalk between the two fluorescence dyes, the inventors used sequential methods featured by Leica confocal microscope to measure colocalization of the two proteins, in which, the two laser lines 488 nm and 546 nm were applied to the cells alternatively. Colocalization analysis was performed with Leica Confocal Software, version 2.5 build 1347.

Data Analysis

Data are given as mean±SE. Statistical analysis was performed using the Student's t test, and significance was accepted at $p<0.05$.

Results

Interaction of the Na+/K+-ATPase with Src

Ouabain binding to the Na+/K+-ATPase activated Src kinase in several different cell lines. In addition, Src could be coimmunoprecipitated with the Na+/K+-ATPase α1 subunit and that ouabain regulated this interaction in a time and dose-dependent manner (Haas et al., 2002).

The inventors now believe that the signaling Na+/K+-ATPase may interact with Src to form a signaling complex. To confirm, LLC-PK1 cells were fixed and double-stained by a monoclonal anti-α1 and a polyclonal anti-Src antibody. The Na+/K+ ATPase α1 and Src colocalized in the plasma membrane in LLC-PK1 cells (FIG. 1A).

Pixel analysis indicated that 25.2±1.3% of Na+/K+-ATPase in the plasma membrane colocalized with Src. Similar colocalization between these two proteins was also observed in 293T cells that overexpressed Src-ECFP. To test whether the Na+/K+-ATPase and Src interact in LLC-PK1 cells, the inventors transfected the cells with Src-ECFP and EYFP-rat α1. Fluorescence resonance energy transfer (FRET) analysis was performed in the transfected cells using acceptor photobleaching protocols. Rat α1 was chosen for the initial FRET experiments because the inventors have a rat α1-specific antibody so that the inventors could confirm the expression of the transfected α1 using Western blot in addition to monitoring YFP fluorescence. The data showed an energy transfer from Src-ECFP to EYFP-rat α1.

Figure 1B:
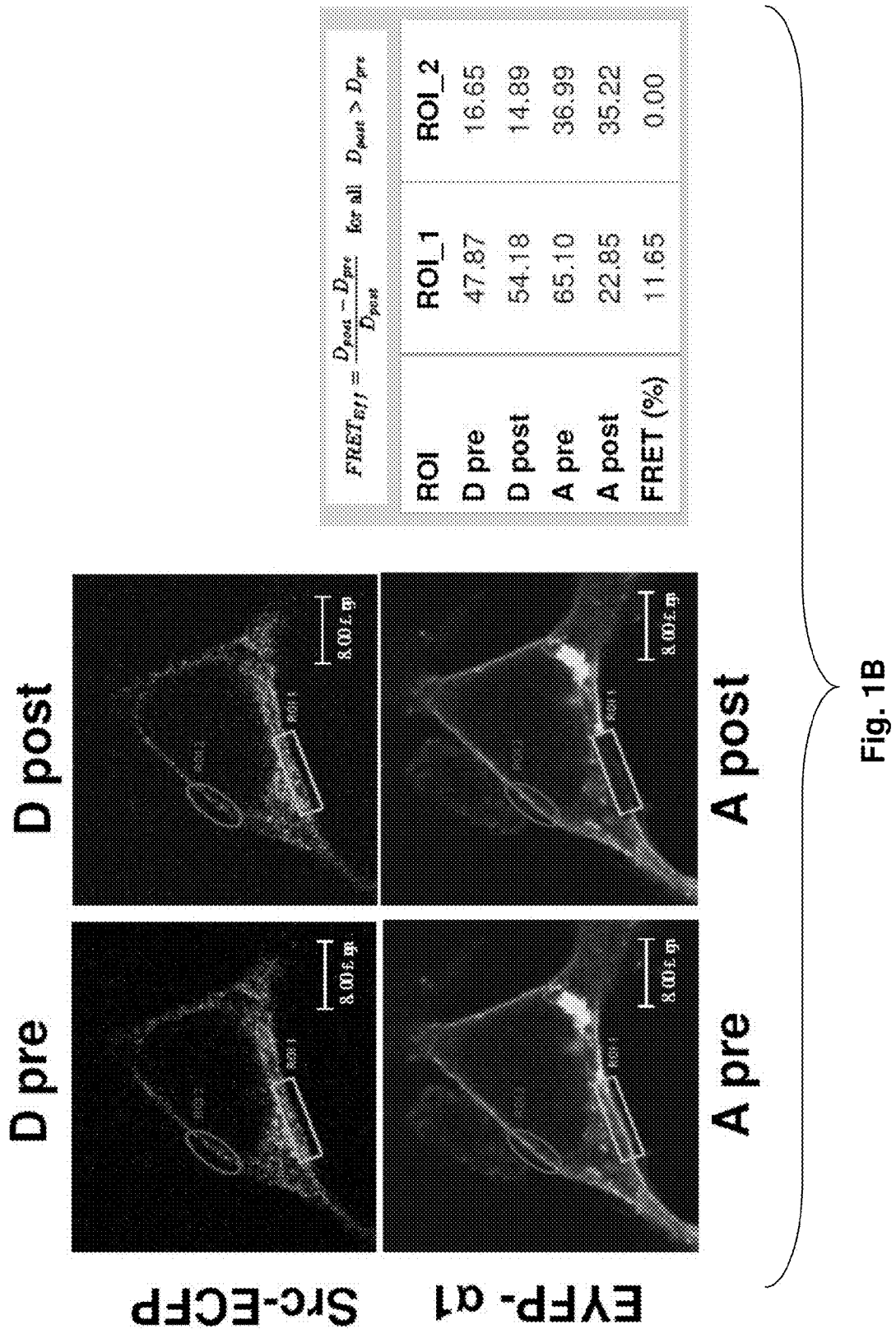
FIG. 1B. Fluorescence resonance energy transfer (FRET) analysis of the interaction between EYFP-rat α1 (yellow) and Src-ECFP (cyan) in LLC-PK1 cells. The boxed area (ROI 1) was photobleached and analyzed for FRET. The inventors also measured FRET at the circled area (ROI 2) that was not photobleached. The same studies were performed in 16 cells from 6 independent experiments. Scale bar, 8 μm.

As shown in FIG. 1B, photobleaching of the EYFP-rat α1 resulted in an increase in the Src-ECFP signal. The FRET efficiency measured from a total of 16 cells in six separate experiments ranged from 8.1 to 18.8 (13.2±1.7). In contrast, no FRET was detected in cells transfected with a pair of either ECFP/EYFP or ECFP/EYFP-rat α1. These data show that the Na+/K+-ATPase and Src are in close proximity, showing a direct interaction between these two proteins in LLC-PK1 cells.

Figure 2A:
FIGS. 2A-D. Binding of the purified pig kidney Na+/K+-ATPase (PKE) to GST-Src. Purified Na+/K+-ATPase was solubilized in 1% Triton X-100. After centrifugation at 100,000×g, indicated amounts of the cleared supernatants were incubated with 5 μg GST-Src in the presence of 0.5% Triton X-100 for 30 min and followed by four washes with the same buffer.
Figure 2B:
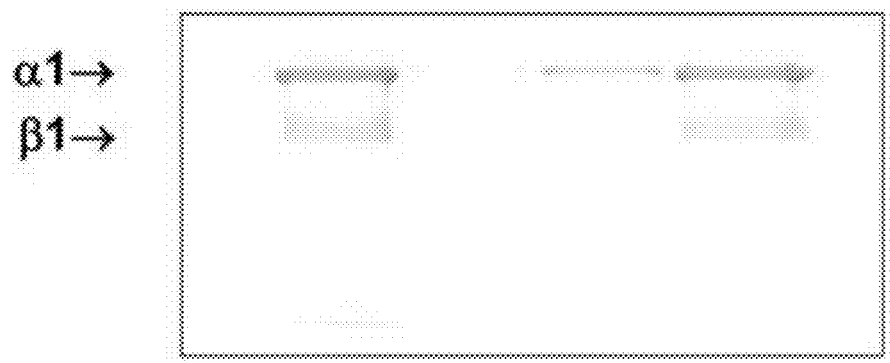

To obtain evidence of direct binding, the inventors first performed in vitro binding assays using the purified pig kidney Na+/K+ ATPase (PKE) and GST-Src. It is important to note that the purified Na+/K+-ATPase is a membrane-attached preparation in which the α1 and β1 subunits are associated in a 1:1 molar ratio and accounts for more than 90% of protein contents in the preparation (FIG. 2B and Jorgensen, 1974, 1988).

Figure 2C:
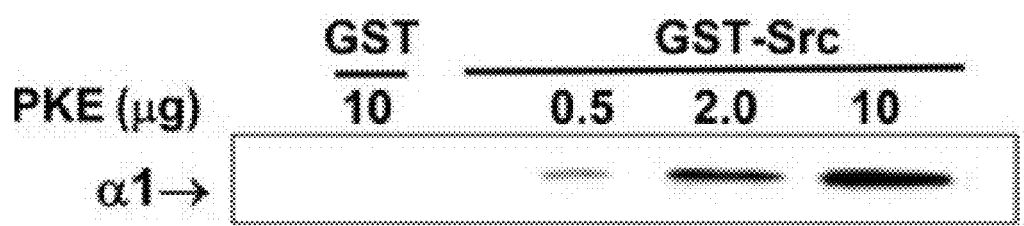
Figure 2D:
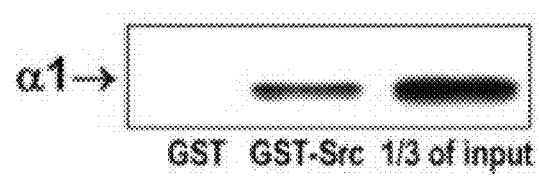
Figure 3C:
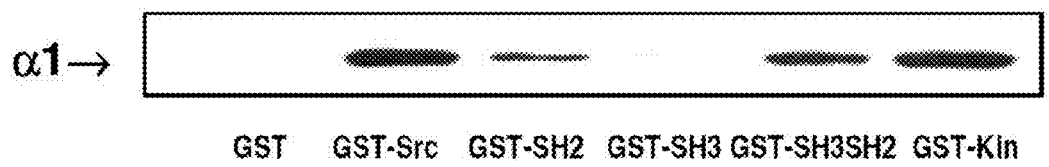

As depicted in FIG. 2C, the 1% Triton X-100-solubilized Na+/K+-ATPase bound to GST-Src in a concentration-dependent manner. A significant amount of α1 subunit was detected when 0.5 μg of the Na+/K+-ATPase was used in the binding assay. To quantitate the binding, experiments as shown in FIG. 2D were performed. The data showed that GST-Src pulled down 12±2.4% (n=3) of the input when 2 μg of the purified Na+/K+-ATPase was used. These data suggest a possibility of direct binding between Src and the Na+/K+ ATPase. To control that the binding was not induced by solubilization of the Na+/K+-ATPase, the inventors repeated the above experiments with the purified Na+/K+-ATPase in the absence of detergent, showing the similar interaction between the Na+/K+-ATPase and GST-Src. To dissect which domains of Src interact with the Na+/K+-ATPase (for domain structures see FIG. 3A), the inventors expressed and purified the GST-SH2, GST-SH3, GST-SH3SH2, and GST-kinase domain fusion proteins (Ma et al., 2000). Using the same in vitro binding assay, the inventors observed that the purified Na+/K+ ATPase bound to the kinase domain, the SH3SH2, and the SH2 domain, but not the SH3 domain (FIG. 3C). Because the GST-SH3SH2 pulled down more Na+/K+-ATPase than that of the GST-SH2, this construct was used in subsequent experiments.

Figure 4A:
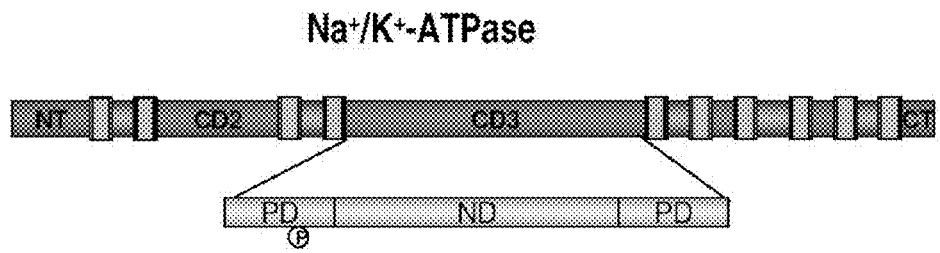
FIGS. 4A-D. Identification of the Na+/K+-ATPase domains involved in the interaction with Src.

Although it is unlikely that Src or its domain constructs pulled down the Na+/K+-ATPase via their binding to an intermediate protein component of the purified enzyme preparations, to rule out this possibility and to identify which domains of the Na+/K+-ATPase are involved in its interaction with Src, the inventors prepared GST-fused proteins containing the N-terminus (GST-NT), the second cytosolic loop (GST-CD2), and the large central loop connecting the transmembrane helices M4 and M5 (GST-CD3; FIG. 4A) of the α1 subunit of the Na+/K+-ATPase because these domains are known to interact with various proteins.

Figure 4B:
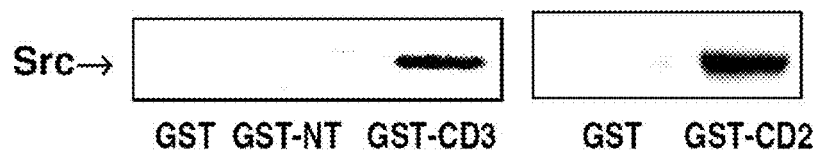
Figure 4C:
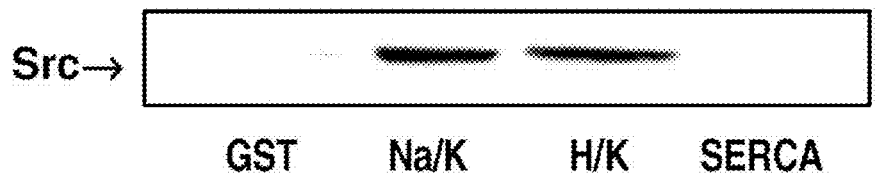

As shown in FIG. 4B, Src interacted with GST-CD3 and GST-CD2, but not GST-NT. To further test if the binding is specific to the Na+/K+-ATPase, the inventors made GST fusion proteins of the CD3 from rat gastric H+/K+-ATPase and rat heart sarcoplasmic reticulum Ca2+-ATPase 2a (SERCA). The data showed that the GST-CD3 from the H+/K+-ATPase, but not the SERCA, pulled down Src from the LLC-PK1 cell lysates (FIG. 4C).

Figure 4D:
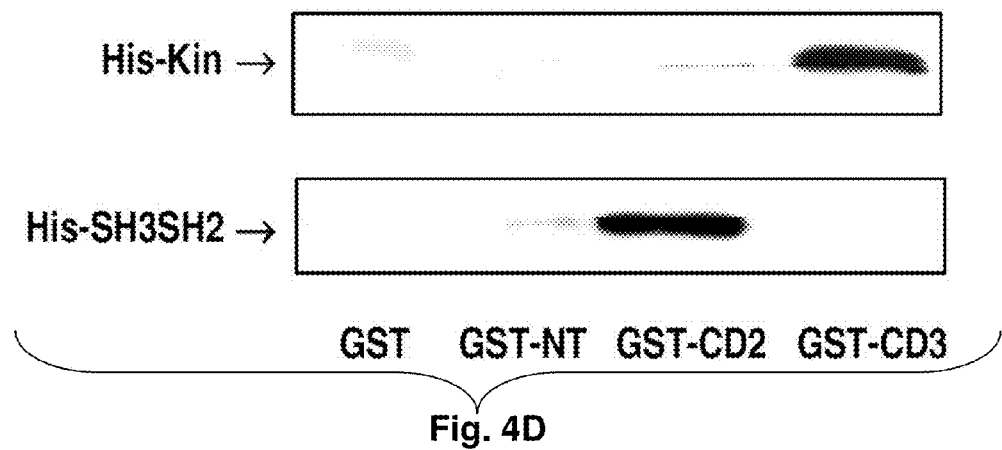

To map the specific domain interactions between the Na+/K+-ATPase and Src, the inventors prepared His tagged kinase domain and SH3SH2 domain fusion proteins. Employing the same binding assay, the inventors found that the GST-CD3 interacted with the kinase domain, but not the SH3SH2 domain of Src. In contrast, the CD2 interacted with the SH3SH2 domain, but not the kinase domain (FIG. 4D). Taken together, the above results indicate that Na+/K+ ATPase can directly interact with Src through the CD2 and CD3 domains of the α1 subunit.

Regulation of Src by the Na'/K+-ATPase

Because binding of SH3SH2 domain to a regulatory protein is sufficient to activate Src, the inventors tested whether binding of Src to the Na+/K+-ATPase results in Src activation. When purified recombinant Src was incubated with different amounts of the purified Na+/K+-ATPase in the presence of ATP/Mg2+ in detergent-free PBS solution, the autophosphorylation of Src at Tyr418 (pY418), an indication of Src activation, was reduced in a concentration dependent manner (FIG. 5A). Because the inventors observed the same results when the experiments were repeated in the presence of 100 μM vanadate that completely inhibited the hydrolysis of ATP by the Na+/K+-ATPase, the effect of the Na+/K+ ATPase on Src is likely due to the interaction between these two proteins, but not the reduction of ATP. To further test this hypothesis, the inventors determined the effect of CD3 on Src. Because the Wiskott-Aldrich syndrome protein is reported to inhibit Src by binding to the kinase domain, the inventors reasoned that interaction between the CD3 and the kinase domain might be sufficient to keep Src in an inactive state. Indeed, as shown in FIG. 5B, GST-CD3, but not GST, acted as the purified Na+/K+-ATPase, caused a dose-dependent inhibition of the Src pY418.

Because the above data suggest that the Na+/K+-ATPase may bind Src and keep it in an inactive state, the inventors now believe that the Na+/K+-ATPase/Src complex may constitute a functional complex for ouabain and act in a manner similar to that of G protein-coupled receptor/G protein complex; namely, binding of ouabain to this complex releases the trapped Src kinase domain, resulting in Src activation and subsequent tyrosine phosphorylation of downstream effectors. To test, the inventors incubated the recombinant Src with the purified Na+/K+-ATPase in detergent-free PBS solution in the presence or the absence of ouabain. Western blot analysis indicated that addition of ouabain significantly increased the pY418 in a dose-dependent manner (FIG. 6A).

To confirm that changes in pY418 correlates with Src activity, the inventors also measured the Src-mediated tyrosine phosphorylation using a commercial available kinase assay kit. As shown in FIG. 6B, although the Na+/K+-ATPase kept Src in an inactive state, addition of ouabain restored the kinase activity. The inventors also determined if vanadate affected the activity of this Na+/K+-ATPase/Src complex. As shown in FIG. 6C, although 10-100 μM vanadate completely inhibited the ATPase activity, it showed no effect on Src pY418. More importantly, ouabain was still able to stimulate pY418 of Src in the presence of vanadate.

To test whether ouabain activates Src by dissociating it from the interacting Na+/K+-ATPase, the inventors incubated Src with the purified Na+/K+-ATPase. Because the purified Na+/K+-ATPase is attached to the membrane, it can be pelleted by centrifugation at 100,000×g for 30 min. Centrifugation was sufficient to sediment Src only when it was bound to the Na+/K+-ATPase. Western blot analysis also showed that the cosedimented Src was kept in an inactive state (FIG. 7A), which is consistent with the findings presented in FIG. 5. Because only the Na+/K+-ATPase-bound Src can be pelleted down, the inventors reasoned that the recovered Src would be reduced in ouabain-treated samples if ouabain dissociates Src from the Na+/K+-ATPase.

Surprisingly, when the same analysis was conducted after the samples were treated with ouabain before centrifugation, the inventors found that ouabain had no effect on total Src cosedimented with the Na+/K+-ATPase, yet increased the amount of Src pY418 (FIG. 7B). Because the inventors have shown that multiple domains are involved in Src interaction with the Na+/K+ ATPase, the above findings led us to test if ouabain dissociates only a single (kinase) domain from the interacting Na+/K+-ATPase. To do so, 1 μg of the purified Na+/K+ ATPase was incubated with GST-Src, GST-SH3SH2, or GST kinase in detergent-free PBS solution, and the complexes were collected by centrifugation. Afterward, the complexes were exposed to 10 μM ouabain.

Figure 7D:
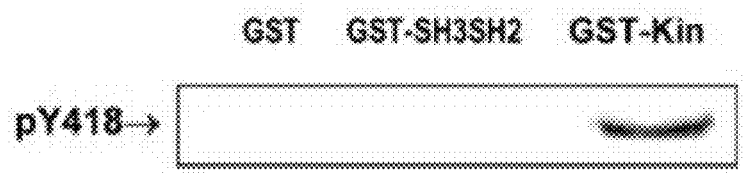

As depicted in FIG. 7C, ouabain showed no effect on the binding of either full-length Src or the SH3SH2 domain to the Na+/K+-ATPase, but dissociated the kinase domain from the Na+/K+-ATPase, which is in accordance with the findings presented in FIG. 5. The fact that ouabain had no effect on the binding of the SH3SH2 domain to the Na+/K+-ATPase apparently explains why ouabain did not change the overall binding of Src to the enzyme. To further test if releasing of the kinase domain is sufficient to activate Src, the inventors pre-incubated the GST-kinase fusion protein with the Na+/K+-ATPase before adding full-length Src to compete for the kinase domain binding sites. Western blot analysis showed that GST-kinase, but not GST or GST-SH3SH2, significantly increased Src pY418 (FIG. 7D). Taken together, these findings provide strong support for the notion that ouabain activates the Na+/K+-ATPase/Src complex by freeing the trapped kinase domain of Src.

Ouabain Activates the Na+/K+-ATPase/Src Complex and Stimulates Protein Tyrosine Phosphorylation in Live Cells If ouabain activates the Na+/K+-ATPase/Src complex by releasing the kinase domain in live cells, the inventors now believed that ouabain would increase the distance between the kinase domain and the interacting Na+/K+-ATPase because the freed kinase domain will bind and phosphorylate its effectors. This could result in the reduction of FRET signal between coexpressed Src-ECFP and EYFP-rat α1. To test, the inventors performed live cell FRET as well as BRET analysis.

As shown in FIG. 8A, excitation of ECFP at 456 nm caused emissions in both ECFP spectrum (detected between 465 and 509 nm as FECFP) and EYFP spectrum (detected between 530 and 570 nm as FEYFP) in control cells, indicating a potential FRET between Src-ECFP and EYFP-rat α1. To test if ouabain stimulates the release of the kinase domain, the same cell was then exposed to ouabain and measured for both ECFP and EYFP intensity. As shown in FIG. 8A, once the cells were exposed to 100 μM ouabain, there was a time-dependent decrease in $F_{EYFP}$ and a concomitant increase in $F_{ECFP}$, indicating that ouabain caused a reduction in FRET between Src-ECFP and EYFP-rat α1. As a control, the same experiments were repeated in cells transfected with ECFP and EYFP, and no detectable FRET was observed.

Because ECFP has to be excited in order to perform FRET analysis, photobleaching and spectral bleedthrough do occur during the experiments, complicating data analysis, especially in live cells. In addition, because ouabain-insensitive rat α1 was used for FRET analysis, the inventors wanted to test if ouabain-sensitive α1 also functions similarly to the rat α1. Therefore, the inventors performed the BRET analysis using GFP canine α1 and Src-*Renilla* luciferase (Src-Rluc) to corroborate the above findings. Both constructs were transiently transfected into 293T cells and a construct of GFP-fused Rluc was used as a positive control. Human 293T cells were chosen for BRET analysis because these cells could be more easily transiently transfected under our experimental conditions.

As shown in FIG. 8B, coexpression of GFP-canine α1 and Src-Rluc yielded a BRET ratio comparable to that of the positive control, indicating that Src interacts with the Na+/K+-ATPase in live cells. Significantly, when the transfected cells were exposed to different concentrations of ouabain, ouabain caused a dose-dependent decrease in the BRET ratio. Significant decrease was detected when 10 nM ouabain was used (FIG. 8C). These data are consistent with the known ouabain sensitivity of the canine α1 and support the results of FRET analysis in FIG. 8A.

Increases in protein tyrosine phosphorylation are essential for ouabain-induced changes in cellular functions. Although activation of Src by ouabain leads to transactivation of the Na+/K+-ATPase associated EGF receptor and PLC-,y, the inventors have not tested whether the activation of the identified Na+/K+-ATPase/Src complex is responsible for ouabain-induced tyrosine phosphorylation of other proteins that are associated with the signaling complex.

To test, LLC-PK1 cells were exposed to 1 μM ouabain for 5 min. Cell lysates from both control and treated cells were then immunoprecipitated with anti-α1 antibody. When the immunoprecipitates were resolved on SDS-PAGE and probed for phosphotyrosine with anti-phosphotyrosine antibody, the inventors observed that ouabain indeed stimulated tyrosine phosphorylation of multiple Na+/K+-ATPase-associated proteins (FIG. 9A). To confirm that Src is required for the initiation of protein tyrosine phosphorylation in response to ouabain, the inventors repeated the same experiments in Src family kinase-knockout SYF cells.

As shown in FIG. 9B, the effects of ouabain on protein tyrosine phosphorylation were completely abolished in SYF cells. On the other hand, when Src is knocked back into the SYF cells (SYF+Src), ouabain's effects on protein tyrosine phosphorylation were restored, indicating an essential role of Src in initiation of ouabain-activated protein tyrosine phosphorylation. This is further supported by the fact that Src inhibitor PP2 was able to block ouabain-induced protein tyrosine phosphorylation in SYF+Src cells.

Because the inventors have shown that ouabain stimulated the recruitment of Src to the Na+/K+-ATPase signaling complex, the inventors now believe that ouabain first activates the Na+/K+-ATPase-bound Src and subsequently results in tyrosine phosphorylation of EGFR, caveolin-1, and other effectors. These effectors in turn provide binding sites for recruiting additional Src and other signaling proteins onto the signaling complex.

To test, the inventors treated the LLC-PK1 cells with 1 μM ouabain for 5 min in the presence or absence of 1 μM PP2. Cell lysates were then immunoprecipitated by anti-α1 antibody. Western blot analysis of the immunoprecipitants showed that ouabain increased coprecipitated Src in control cells, but not in cells that were pretreated with PP2 (FIG. 9C), supporting the notion that the initial activation of Src is necessary for recruiting additional Src to the complex. Control experiments also showed that pretreatment of LLC-PK1 cells with PP3, an inactive analog of Src inhibitor PP2, failed to block ouabain-induced recruitment of Src to the Na+/K+-ATPase (FIG. 9C).

To corroborate the above findings, the inventors also performed the immunoprecipitation experiment with isolated caveolae preparations from LLC-PK1 cells. The inventors showed previously that ouabain increased tyrosine phosphorylation of proteins in a Src-dependent manner in the isolated caveolae preparations. It also stimulated the formation of the Na+/K+-ATPase/caveolin-1/Src complex (Wang et al., 2004). However, because addition of ATP is required for ouabain to activate Src in the isolated caveolae, the inventors believed that ouabain could not stimulate the recruitment of Src to the caveolin-1 complex in the absence of ATP if Src activation and tyrosine phosphorylation of caveolin-1 is required for the additional recruitment of Src. Indeed, this is what the inventors observed when the inventors repeated the above experiments in the absence of ATP (FIG. 9D). Taken together, the data clearly show that ouabain signals through the Na+/K+-ATPase by first activating Src and then recruiting more effector proteins including Src to the signaling Na+/K+-ATPase.

Discussion

The inventors now show mapped domains that are involved in Na+/K+-ATPase/Src interaction. The inventors further demonstrate that the Na+/K+-ATPase and Src can assemble into a functional signaling complex via the identified protein domains and that the binding of ouabain to the Na+/K+-

ATPase activates Src and provokes downstream protein tyrosine phosphorylation. This and other conclusions are summarized in FIG. 10 and discussed below.

The Na+/K+-ATPase/Src Complex as a Receptor for Cardiotonic Steroids

Because the α1 subunit of Na+/K+-ATPase contains a conserved proline-rich motif in its N-terminus (Yudowski et al., 2000), the inventors initially thought that ouabain might promote the interaction between the SH3 of Src and the Na+/K+-ATPase, resulting in the activation of Src. To the inventors' surprise, GST pulldown assay showed that the SH3 domain was not involved in direct interaction with the Na+/K+-ATPase. Instead, the SH2 and the kinase domains of Src interact with the CD2 and CD3 domains of the Na+/K+-ATPase α1 subunit, respectively. In addition, the inventors' results showed that both Na+/K+-ATPase and GST-CD3 inhibited Src activity (FIG. 5). Although the inventors cannot exclude the possibility that other Src regulator copurified with Na+/K+-ATPase is involved, the fact that purified CD3 domain alone could mimic the effect of Na+/K+-ATPase strongly suggested that Na+/K+-ATPase is sufficient to inactivate Src.

The fact that the Na+/K+-ATPase and Src form an inactive Src complex led the inventors to now believe that this receptor complex may transmit the ouabain signals in a way similar to those of cytokine receptors. Although these receptors have no intrinsic kinase activity, coupling to Src allows them to activate the downstream protein tyrosine phosphorylation. Several examples described herein support this notion.

First, ouabain-induced changes in the conformation of the Na+/K+-ATPase are sufficient to free the kinase domain of Src (FIG. 7). Interestingly, thapsigargin, an inhibitor of SERCA, is able to bring the CD3 close to the membrane. If ouabain can exert similar effect on the CD3, this may explain how ouabain releases the kinase domain from the Na+/K+-ATPase. On the other hand, because ouabain has no effect on the binding of the SH3SH2 domain to the CD2, this domain could function as a hinge, keeping the activated Src binding to the signaling Na+/K+-ATPase for specific and robust signal transmission.

Second, antagonizing the binding of Src kinase domain to the Na+/K+-ATPase by addition of GST-kinase domain fusion protein acted as ouabain and stimulated Src pY418.

Third, the observed effect of ouabain on Src (FIG. 6) is not due to the inhibition of the ATPase activity because vanadate showed no effect on Src at the concentration that completely inhibited the ATPase activity.

Furthermore, the GSTCD3, which does not hydrolyze ATP, can also inhibit Src activation. Similarly, the findings also argue against the involvement of changes in ion concentrations in ouabain-induced activation of Src because these experiments were performed in the test tubes under the same ionic conditions.

Finally, both FRET and BRET analyses indicated that ouabain did release the kinase domain in live cells (FIG. 8). It is important to note that the effects of ouabain on the Na+/K+-ATPase/Src-kinase domain interaction were dosedependent and correlated well with the known dose-response curve of ouabain binding to the Na+/K+-ATPase (Haas et al., 2002).

In short, the inventors have demonstrated a novel mechanism of ouabain-provoked signal transduction. Because Src family kinases are highly conserved, the inventors believe that the signaling Na+/K+ ATPase may interact with other members of the Src family. In addition, mammalian cells express at least four different types of α subunit in a tissue-specific manner, and it is now believed that different isoforms may also interact with Src in a tissue-specific manner. To this end, it is of interest to note that Src also interacts with the CD3 domain of H+/K+-ATPase (FIG. 4C), suggesting a potential signaling function of the H+/K+-ATPase in regulation of Src activity.

The inventors also believe that these P-ATPases may also serve as Src effectors because recent studies have suggested a Src-mediated tyrosine phosphorylation of these P-ATPases. (Kanagawa et al., 2000; Masaki et al., 2000; Ferrandi et al., 2004).

Significance of Findings

Na+/K+-ATPase is well-known for its essential function in maintaining the Na+ and K+ ion concentrations across cell membrane in mammalian cells. The fact that the binding site for cardiotonic steroids is so conserved throughout the phylogeny of eukaryotes indicates that these steroids must play an important role in regulation of the Na+/K+-ATPase function. Because the ion pumping was the only known function of the Na+/K+-ATPase until a few years ago, it is well accepted by the field that cardiotonic steroids must signal by inhibition of the ATPase activity although there is no hormonal precedent for such signal transduction. This mode of action has led many in the field to question the significance of endogenous cardiotonic steroids because they circulate at subnanomolar concentrations under normal physiological conditions, and can only bind to 1-2% of cell surface Na+/K+-ATPase. Because most mammalian cells contain ~1 million Na+/K+-ATPase molecules per cell, it is highly inefficient for cardiotonic steroids to purely function as an inhibitor to the pumping function of Na+/K+-ATPase because they have to work against the large pumping capacity of the cells. On the other hand, if the binding site is conserved for regulating the signaling function of the Na+/K+-ATPase, cardiotonic steroids will function as true agonists. As estimated by our colocalization analysis, ~25% of the Na+/K+-ATPase has the potential to interact with Src. Activation of 1-2% of these receptors by ouabain will produce a few thousand active molecules per cell. Based on the findings of EGF signaling in HeLa cells and the principle of signal amplification, this will be sufficient to generate strong signals via kinase cascades, especially if the signaling event occurs in a membrane microdomain such as caveolae. Consistent with this, recent studies have demonstrated in both cultured cells and animal models that physiological concentrations of ouabain (e.g., 0.1-1 nM) were able to activate Src and ERKs (Aydemir-Koksoy et al., 2001; Ferrandi et al., 2004).

Pharmacologically, the inventors have demonstrated that ouabain-induced inotropy is accompanied by the activation of Src and ERKs in the isolated heart preparations as well as in the cultured myocytes (Mohammadi et al., 2003). Furthermore, inhibition of Src and ERKs blocked ouabain-induced increases in intracellular Ca2+ in cardiac myocytes (Tian et al., 2001).

Thus, the examples herein reveal the possible molecular mechanism of digitalis-induced inotropy in the heart. The examples herein also show that this is useful for developing chemicals or peptides that can stimulate the signaling function of the Na+/K+-ATPase without affecting the ion pumping function. In addition, the inventors herein provide the insight into the molecular mechanism, by which a membrane transporter uses Src to form a functional signaling complex. Because many membrane transporters and ion channels undergo either substrate- or ligand-dependent conformational changes as the Na+/K+-ATPase, these findings raise an important biological question as to whether other membrane transporters are also involved in signal transduction, thus constituting another group of important receptors and signal transducers. To this end, the inventors note that the CD3 of Na+/K+-ATPase is highly conserved among many different P-type ATPases and now believe that other P-type ATPases are (e.g., H+/K+-ATPase shown in FIG. 4C) also involved in regulation of Src. The inventors also note that several recent reports have demonstrated that Src interacts with and regulates many other membrane ion channels (Yu et al., 1997; Sobko et al., 1998; Tiran et al., 2003).

EXAMPLE II

Functional Characterization of Src-Interacting Na+/K+-ATPase Using RNA Interference Assay The Na+/K+-ATPase and Src form a signaling receptor complex. Here the inventors show how alterations in the amount and properties of the Na+/K+-ATPase affect basal Src activity and ouabain-induced signal transduction. Several α1 subunit knockdown cell lines were generated by transfecting LLC-PK1 cells with a vector expressing α1-specific small interference RNA. Although the α1 knockdown resulted in significant decreases in Na+/K+-ATPase activity, it increased the basal Src activity and tyrosine phosphorylation of focal adhesion kinase, a Src effector. Concomitantly it also abolished ouabain-induced activation of Src and ERK1/2. When the knockdown cells were rescued by a rat α1, both Na+/K+-ATPase activity and the basal Src activity were restored. In addition, ouabain was able to stimulate Src and ERK1/2 in the rescued cells at a much higher concentration, consistent with the established differences in ouabain sensitivity between pig and rat α1. Finally, both fluorescence resonance energy transfer analysis and co-immunoprecipitation assay indicated that the pumping-null rat α1 (D371E) mutant could also bind Src. Expression of this mutant restored the basal Src activity and focal adhesion kinase tyrosine phosphorylation. Taken together, the inventors now believe that LLC-PK1 cells contain a pool of Src-interacting Na+/K+-ATPase that not only regulates Src activity but also serves as a receptor for ouabain to activate protein kinases.

The activation of Src is essential for ouabain-induced changes in many cellular activities including the regulation of intracellular calcium, gene expression, and cell growth and the inventors have examined whether the Na+/K+-ATPase interacts directly with Src to form a functional signaling receptor.

Using in vitro glutathione S-transferase pulldown assays the inventors have now identified that the second and the third intracellular domains of the Na+/K+-ATPase α1 subunit interact with the Src SH2 and the kinase domains, respectively. Functionally, these interactions keep Src in an inactive state, and binding of ouabain to this inactive Na+/K+-ATPase•Src complex frees and then activates the associated Src. These new examples show that the cellular Src-interacting Na+/K+-ATPase is now believed to play an important role in regulation of the basal Src activity and serve as a functional receptor for ouabain to stimulate protein tyrosine phosphorylation in live cells. To test, the inventors developed an siRNA-based assay that allows us to determine the effect of changes in the amount and properties of the Na+/K+-ATPase on both basal and ouabain-stimulated Src activity.

Materials and Methods

Chemicals of the highest purity were purchased from Sigma. The GeneSuppressor vector was purchased from BioCarta (San Diego, Calif.). Cell culture media, fetal bovine serum, trypsin, Lipofectamine 2000, and restriction enzymes were purchased from Invitrogen. EYFP expression vector (pEYFP) and ECFP expression vector (pECFP) were obtained from Clontech. QuikChange mutagenesis kit was purchased from Stratagene (La Jolla, Calif.). Optitran nitrocellulose membrane was from Schleicher & Schuell. Enhanced chemiluminescence SuperSignal kit was purchased from Pierce. Image-iT FX signal enhancer, Antifade kit, Alexa Fluor 488-conjugated antimouse/rabbit IgG and Alexa Fluor 546-conjugated anti-mouse/rabbit IgG antibodies were obtained from Molecular Probes (Eugene, Oreg.). Anti-Src (clone GD11) monoclonal antibody, anti-Na+/K+-ATPase α1 polyclonal and monoclonal (clone C464.6) antibodies, anti-phosphotyrosine (clone 4G10) antibody, and protein G-agarose were from Upstate Biotechnology Inc. (Lake Placid, N.Y.). The polyclonal anti-Tyr(P)418-Src and anti-Tyr(P)529-Src antibodies were from BIOSOURCE (Camarillo, Calif.). The polyclonal anti-FAK and anti-Tyr(P)925FAK antibodies were from Cell Signaling (Danvers, Mass.). The monoclonal anti-α1 antibody (a6F) was obtained from the Developmental Studies Hybridoma Bank at the University of Iowa. Anti-c-Src (B-12) monoclonal antibody, anti-c-Src (SRC2) polyclonal antibody, anti-ERK (C-16) polyclonal antibody, anti-pERK (E-4) monoclonal antibody, and all the secondary horseradish peroxidase-conjugated antibodies were from Santa Cruz Biotechnology Inc. (Santa Cruz, Calif.). Polyclonal rat α1-specific antibody (anti-NASE) was provided by Dr. Thomas Pressley (Texas Tech University, Lubbock, Tex.).

Cell Culture

LLC-PK1 cells and human embryonic kidney 293T cells were obtained from American Type Culture Collection and maintained in Dulbecco's modified Eagle's medium containing 10% fetal bovine serum, 100 units/ml penicillin, and 100 µg/ml streptomycin in a 5% CO2-humidified incubator.

Construction of the siRNA Expression Vectors siRNAs were constructed using the GeneSuppressor construction kit. Briefly, four pairs of oligonucleotides (A1-A4) were synthesized using the human α1 cDNA (GenBank™ accession number NM_000701) as template (see Table 1 for details), and the inserts were prepared by annealing two complementary oligonucleotides. The annealed inserts were then cloned into pSuppressor™-U6 vector digested with SalI and XbaI. Positive clones were confirmed by nucleotide sequencing.

Site-Directed Mutagenesis

Rat α1 expression vector pRc/CMV-α1 AAC was provided by Dr. Pressley (12). To make the expression of rat α1 insensitive to A4 siRNA, the α1 siRNA targeted sequence was silently mutated from 2530ggtcgtctgatcttt (GenBank™ accession number NM_012504) to 2530ggcaggctaatattc using the QuikChange mutagenesis kit. The SspI (aat/att) restriction site was generated to facilitate the clone screening. The positive mutant (pRc/CMV-α1 AACm1 or AAC in short) was verified by DNA sequencing and then used in this study. The pumping-null mutant (D371E) was generated by mutating the 1126gacaag to 1126gagaag using pRc/CMV α1AACm1 as the template (13).

Generation of Stable α1 Subunit Knockdown and Knock-in Cell Lines

Human embryonic kidney 293T cells were transiently transfected with different siRNA expression vectors along with pEYFP using Lipofectamine 2000. After 48 h, cells were first examined for the expression of EYFP for assessing the transfection efficiency and then collected for analysis of endogenous α1 content by Western blot. To generate stable cell lines, one batch of LLC-PK1 cells was transfected with the A4 siRNA expression vector (pSuppressor-A4 siRNA) (see FIG. 25—Table 1) and a puromycin selection marker (pBade-puro).

FIG. 25 shows Table 1 with targets and oligo sequences of human Na/KATPase-α1 subunit-specific siRNAs where the target sequences are marked by bold letters. [SEQ ID NOS: 35-46].

Another batch of cells was co-transfected with pEYFP together with the pSuppressor-A4 siRNA and pBade-puro so that the co-expressed EYFP could be used as a marker to pick clones. Empty vector (pSuppressor) or A1 siRNA-transfected cells were co-selected and used as a control. The cells were selected with puromycin (1 µg/ml) 24 h posttransfection. Puromycin-resistant colonies were cloned and expanded. To rescue the Na+/K+-ATPase knockdown cells, cells were transfected with the pRc/CMV-α1 AACm1. Selection was initiated with 3 µM ouabain because untransfected cells were very sensitive to ouabain. After about 1 week, ouabain-resistant colonies were isolated and expanded into stable cell lines in the absence of ouabain. G418 was not used because these cells are resistant to it, requiring more than 3 mg/ml to kill the untransfected cells. The knockdown cells were also sensitive to blasticidin (15 µg/ml), and the inventors are also using this agent for other selections.

Immunoprecipitation and Immunoblot Analysis

Cells were washed with PBS, solubilized in modified ice-cold radioimmune precipitation assay buffer, and subjected to immunoprecipitation or Western blot analysis. Protein signal was detected using the enhanced chemiluminescence kit and quantified using a Bio-Rad GS-670 imaging densitometer.

Na+/K+-ATPase Activity Assay

Na+/K+-ATPase enzymatic activity was determined. Briefly, cells were collected from the cultures in Tris-EGTA buffer (pH 7.2) and briefly sonicated. The cell lysates were then treated with alamethicin at a concentration of 0.1 mg/mg of protein for 30 min at room temperature. ATPase activity was measured by the determination of the initial release of 32P from [,γ-32P]ATP, and the reaction was carried out in a reaction mixture (1 ml) containing 100 mM NaCl, 25 mM KCl, 3 mM MgCl2, 1 mM EGTA, 2 mM ATP, 5 mM NaN3, and 50 mM Tris-HCl (pH 7.4). Na+/K+-ATPase activity was calculated as the difference between the activities measured in the absence of ouabain and in the presence of 1 mM ouabain. To determine the ouabain concentration curve, the alamethicin-treated cell lysates were preincubated with different concentrations of ouabain for 15 min before ATP was added to start the reaction.

Confocal Fluorescence Microscopy

Cells cultured on coverslips were washed twice with PBS and fixed for 15 min with methanol prechilled at −20° C. The fixed cells were then rinsed with PBS three times and blocked with 200 µl of Image-iT FX signal enhancer for 30 min at room temperature. The cells were washed again and incubated with the primary antibodies in PBS containing 1% bovine serum albumin for 1 h at room temperature. After three washes with PBS, the cells were incubated with corresponding Alexa Fluor-conjugated secondary antibodies. Image visualization was performed using a Leica DMIRE2 confocal microscope (Leica, Mannheim, Germany). Leica confocal software was used for data analysis.

FRET Analysis by Acceptor Photobleaching

ECFP was fused to the C terminus of Src, and EYFP was fused to the N terminus of rat Na+/K+-ATPase α1 subunit or its mutant. FRET analysis was performed in cells co-transfected with Src-ECFP and EYFP-rat α1 expression vectors using the acceptor photobleaching protocol. Briefly after 24 h culture, cells on a glass coverslip were fixed with methanol prechilled at −20° C. for 15 min and washed twice with PBS solution. The EYFP-rat α1 was photobleached by applying a high intensity 515 nM laser, and the emission of ECFP excited by 456 nM laser was recorded before (Dpre) and after (Dpost) EYFP photobleaching. The FRET efficiency was then calculated by the ratio of (Dpost−Dpre)/Dpre. Cells transfected with either Src-ECFP and EYFP or EYFP-α1 and ECFP expression vectors were used as a control, and no detectable FRET was observed in these control cells.

Data Analysis

Data are given as mean±S.E. Statistical analysis was performed using the Student's t test, and significance was accepted at p<0.05.

Results

Manipulation of the Cellular Na+/K+-ATPase Content by siRNA Based Assays

As shown in Table 1 in FIG. 25, a total of four pairs of the α1-specific siRNAs was selected based. Transient transfection assay in human embryonic kidney 293T cells showed that expression of A4 siRNA resulted in over 40% decreases in the expression of the human α1 subunit, whereas others gave 0 (A1 siRNA) to 20% (A2 and A3 siRNAs) reduction. Because the transfection efficiency was about 50% as indicated by the co-expressed EYFP, the inventors reasoned that A4 siRNA is effective in silencing the expression of endogenous Na+/K+-ATPase. Therefore, LLC-PK1 cells were transfected with A4 siRNA expression vector (pSuppressor-A4 siRNA) and a puromycin selection marker (pBade-puro) either with or without pEYFP as described under "Experimental Procedures." After two rounds of selection, the inventors collected 20 stable transfectants. Western blot analysis using a monoclonal (a6F) antibody showed that the expression of the α1 subunit in these clones was significantly reduced in comparison with the control P-11 cells that were transfected with empty vector (pSuppressor) and selected. In contrast, cell clones (e.g. A1) obtained from the LLC-PK1 cells that were transfected with A1 siRNA expressed α1 at a level comparable to that in P-11 cells (see FIG. 26 Table 2).

FIG. 26 shows Table 2 with the relative α1 subunit protein content and the composition of DNA constructs used in difference cell lines.

The inventors herein have both expanded and further characterized three A4 siRNA-expressing clones. As shown in FIG. 11A, expression of the α1 subunit was significantly reduced in A4-11, TCN23-19, and PY-17 cells. Of these cell lines, the PY-17 cells, which were cloned by using the co-expressed EYFP as a marker, expressed the lowest level of the Na+/K+-ATPase.

Table 2 in FIG. 26 shows the quantitative data on the relative amount of the α1 in these and other cell lines the inventors generated. Because control Western blot using purified Na+/K+-ATPase prepared from pig kidney showed that it was only possible to perform reasonable quantitative assay comparing two samples with less than 6-fold differences in the amount of α1 (data not shown), the inventors measured the relative amount of α1 in these cells by comparing A4-11 with the control P-11 and then TCN23-19 and PY-17 with A4-11. To confirm the above Western blot data, the inventors also probed the blots with a different anti-Na+/K+-ATPase α1 monoclonal antibody (clone C464.6) and an anti-Na+/K+-ATPase α1 polyclonal antibody, showing essentially the same results as in FIG. 11A. In addition, when co-cultured P-11 and PY-17 cells were immunostained using anti-Na+/K+-ATPase α1 antibody (clone C464.6), the inventors found that the green PY-17 cells exhibited no detectable expression of the α1, whereas the plasma membrane of control P-11 cells was clearly labeled by the antibody (FIG. 11B). To be sure that knock down of the α1 subunit does not induce the expression of other isoforms, the inventors analyzed the cell lysates for both α2 and α3 and found no detectable signals in the above cell lines.

In addition, when ouabain-sensitive ATPase activity was measured in the cell lysates, a significant (80%) reduction was noted in the PY-17 cells in comparison with the control P-11 cells (see FIG. 27 Table 3).

FIG. 27 shows Table 3 with the Na+/K+-ATPase activity in the cell lines P-11, PY-17 and AAC-19.

The PY-17 cells have very low endogenous Na+/K+-ATPase and are useful for studying the structure-function properties of the Na+/K+-ATPase when the cells are rescued by knocking in an exogenous α1. To confirm, the inventors first made silent mutations of the rat α1 cDNA to change the siRNA-targeted sequence. The inventors then transfected PY-17 cells with the mutated rat α1 expression vector (pRc/CMV α1AACm1) and generated several stable transfectants. Further analysis of the clone AAC-19 showed that these cells, unlike both P-11 and PY-17, expressed rat α1 (FIG. 12A).

When the same blots were analyzed for total α1 using the monoclonal antibody (a6F), the inventors found that AAC-19 cells expressed an amount of α1 comparable to that in control P-11 cells (FIG. 12A). This result was further confirmed by immunostaining of the co-cultured P-11 and AAC-19 cells using anti-α1 (clone C464.6) antibody. As depicted in FIG. 12B, the green AAC-19 and control P-11 cells exhibited similar levels of the Na+/K+-ATPase in the plasma membrane. Control experiments also demonstrated that the rat α1 was stably expressed in this cell line for at least 20 passages in the absence of ouabain. Functionally knock-in of the rat α1 into PY-17 cells was able to restore Na+/K+-ATPase activity (see FIG. 27—Table 3). Also, it shifted the doseresponse curve of ouabain on the ATPase activity and made the rescued cells less ouabain-sensitive. In fact, the rescued cells behave as rat cell lines that express only the α1 isoform (FIG. 13). It is important to note that PY-17 cells were as sensitive to ouabain as the control P-11 cells and that 10 μM ouabain caused a complete inhibition of the Na+/K+-ATPase.

Regulation of Basal Src Activity by the Na+/K+-ATPase

The in vitro studies showed that the Na+/K+-ATPase directly binds and keeps Src in an inactive state. The inventors herein now believe that this mode of regulation operates in live cells and that reduction of intracellular Na+/K+-ATPase will decrease the interaction, resulting in an increase in basal Src activity. To test, the inventors measured the phosphorylation of Src (Tyr(P)418-Src), indicative of Src activation, in the cell lysates from the above cell lines.

As depicted in FIG. 14A, the expression of total Src was not altered by knockdown of the endogenous Na+/K+-ATPase. However, the levels of active Src were significantly increased in A4-11, TCN23-19, and PY-17 cells. Interestingly, the increase in Src activity appeared to be inversely correlated with the amounts of Na+/K+-ATPase expressed in these cells (FIG. 14B).

These findings were further confirmed by immunostaining the cells with anti-Tyr(P)418-Src antibody, showing that TCN23-19 cells contained much more active Src than P-11 cells contained (FIG. 14C). It is important to note that there was no difference in the amount of active Src between two control cell lines, P-11 and A1 cells.

To test whether the increase in Src activity due to the decreased expression of the Na+/K+-ATPase is reversible upon repletion of the Na+/K+-ATPase, the inventors determined the total Src and the active Src in AAC-19 cells. As depicted in FIGS. 12A-B, AAC-19 cells were derived from the rat α1-transfected PY-17 cells and expressed an amount of the Na+/K+-ATPase comparable to that in control P-11 cells.

Although knock-in of the rat α1 did not change the total Src in AAC-19 cells, it did reduce the level of the active Src to that seen in control P-11 cells (FIGS. 15A and 15B).

As illustrated in Table 3 in FIG. 27, the Na+/K+-ATPase activity was reduced 80% in PY-17 cells. When intracellular Na+ was measured after the cells were incubated in $^{22}$Na+ (0.5 μCi/ml) medium for 60 min to fully equilibrate exchangeable intracellular Na+ with $^{22}$Na+ (15), the inventors found that the steady state intracellular Na+ in PY-17 cells was about twice as much as in P-11 cells. To be sure that changes in Src activity observed in AAC-19 cells are not due to the restoration of the functional Na+/K+-ATPase and subsequent decreases in intracellular Na+, the inventors tested whether knock-in of a pumping-null mutant of the rat α1 is sufficient for the observed interaction between the Na+/K+-ATPase and Src PY-17 cells were transiently transfected with either silently mutated wild-type rat α1 (pRc/CMV α1AACm1) or the rat α1 pumping-null mutant (D371E).

As shown in FIG. 15C, expression of either rat α1 or the mutant reduced active Src in PY-17 cells. To further confirm, the inventors also transiently transfected TCN23-19 cells with the EYFP-fused rat α1 mutant expression vector (pEYFP-D371E) and immunostained for active Src. As depicted in FIG. 15D, the cells expressing the rat α1 mutant had much less active Src in comparison with the untransfected TCN23-19 cells. These data show that the pumping-null Na+/K+-ATPase mutant is still able to interact and regulate Src. To further confirm, the inventors also performed FRET analysis in TCN23-19 cells transiently transfected with EYFP-rat α1 mutant (D371E) and Src-ECFP expression vectors.

As depicted in FIG. 16A, the pumping-null mutant was targeted to the plasma membrane. When FRET was measured in these transfected cells by acceptor photobleaching protocol, an energy transfer from SrcECFP to EYFP-D371E was clearly demonstrated (FIG. 16B). The FRET efficiency measured from a total of 20 cells in three separate experiments ranged from 10.4 to 15.6 (13.2±1.4). These data indicate that the pumping-null Na+/K+-ATPase acts like the wildtype α1 (10) and can interact with Src to form a signaling complex. This conclusion is further supported by the co-immunoprecipitation assay showing that the rat α1 mutant could be co-precipitated by anti-Src antibody (FIG. 16C).

FAK is a known Src effector that plays an important role in regulation of cell migration and proliferation. Activation of Src stimulates phosphorylation of FAK Tyr$^{925}$, which subsequently can lead to the activation of RDK1/2. To examine whether an increase in basal Src activity can result in the activation of Src effectors, the inventors measured tyrosine phosphorylation of FaK in α1 knockdown cells. As depicted in FIG. 17A, cell lysates were immunoprecipitated by an anti-phosphotyrosine antibody, and the immunoprecipitates were probed by anti-FAK antibody. The data clearly showed that the α1 knockdown was capable of increasing the amounts of tyrosine-phosphorylated FAK. Specifically, when cell lysates were probed for Tyr(P)925-FAK, the inventors found a significant increase in Tyr(P)$^{925}$-FAK in both A4-11 and PY-17 cells (FIG. 17B). Interestingly, when total ERK1/2 and pERK1/2 were measured, the inventors found a modest increase in the amount of active ERK1/2 in PY-17 cells (FIG. 17C). This is in accordance with the known function of Tyr (P)$^{925}$-FAK (19, 20). This increase in Tyr(P)$^{925}$ was sensitive to Src inhibitor PP2 (FIG. 17D). It is important to note that the FAK phosphorylation correlated well to the levels of active Src in the PP2-treated knockdown cells. Taken together, these data indicate that the increased Src activity due to the α1 knockdown can stimulate tyrosine phosphorylation of Src effectors. This is further supported by the observation that expression of the pumping-null mutant (D371E) not only restored the basal Src activity but also reduced FAK Tyr$^{925}$ phosphorylation in PY-17 cells (FIG. 17E).

Knockdown of the Na+/K+-ATPase Abolishes Ouabain-Induced Activation of Src and ERK1/2

Because the Na+/K+-ATPase•Src complex serves as a functional receptor for ouabain to induce Src activation and subsequent stimulation of ERK1/2, the above examples led the inventors to test whether knockdown of the Na+/K+-ATPase affects ouabain-activated signal transduction.

As shown in FIG. 18A, although ouabain activated Src in P-11 cells, this effect of ouabain was essentially abolished in PY-17 cells, whereas a significant reduction was observed in A4-11 cells. To be sure that this inhibition is not due to nonspecific defects in receptor signal transduction, the inventors also measured the effect of EGF on Src. The inventors found that epidermal growth factor was able to stimulate SrcTyr(P)$^{418}$ in both P-11 and PY-17 cells (2.5±0.3-fold increase in P-11 versus 1.7±0.2-fold increase in PY-17, n=3). Consistent with the findings on Src, the inventors also failed to detect any ouabain-induced change in ERK1/2 phosphorylation in PY-17 cells (FIG. 18B).

In contrast, epidermal growth factor was able to stimulate ERK1/2 in PY-17 cells. These data support the notion that the Na+/K+-ATPase is indeed the receptor for ouabain-induced signal transduction. This notion is further supported by the findings presented in FIGS. 18 C and 18D, showing that knock-in of the rat α1 not only restored the ouabain responses but also shifted the dose-response curve to the right in AAC-19 cells.

Discussion

In this Example the inventors not only introduced an effective and α1-specific RNA interference assay but also provided a protocol for rescuing the Na+/K+-ATPase-depleted cells. These procedures have made it possible for us to demonstrate that the cellular Na+/K+-ATPase regulates Src and its effector FAK and that the Na+/K+-ATPase•Src complex serves as a sole receptor for ouabain to activate Src and subsequently ERK1/2 in live cells.

Manipulation of the Cellular Na+/K+-ATPase Content by RNA Interference Assays

RNA interference is a cellular mechanism that was first discovered in 1998 in *Caenorhabditis elegans* and refers to the post-transcriptional gene silencing by double-stranded RNA-triggered degradation of a homologous mRNA. This has now been developed as a powerful tool for artificially silencing a specific gene in a variety of biological systems including cultured cells and whole organisms. Using the strategy developed by Paul et al. (2002) and transient transfection assay, the inventors identified that A4 siRNA was effective for silencing the α1 expression. Thus, the inventors transfected pig LLC-PK1 cells with the A4 siRNA expression vector and cloned several stable cell lines. Western blot analysis and immunostaining assay showed that the expression of the α1 in the cloned cell lines was significantly reduced (FIGS. 11 and 12 and FIG. 26—Table 2). For example, the α1 in PY-17 cells is only about 8% of that in control P-11 cells. Functional analysis revealed that depletion of the α1 resulted in an 80% reduction in ouabain-sensitive ATPase activity in PY-17 cells (FIG. 27—Table 3). The inventors have now developed an effective protocol for silencing the expression of endogenous α1 in cultured cells.

To test whether the α1-depleted cells can be used to study the signaling functions of an exogenous/mutant α1, the inventors transfected PY-17 cells with a rat α1 expression vector in which A4 siRNA targeted sequence was silently mutated. By taking advantage of the availability of an antibody that specifically reacts with rat α1, the inventors demonstrate herein that the exogenous rat α1 can be knocked in and that the expression of rat α1 restored not only the total cellular Na+/K+-ATPase protein but also the Na+/K+-ATPase activity. Also, the rat α1-rescued cells (AAC-19) exhibited the same ouabain sensitivity as the rat cell lines that only express the Na+/K+-ATPase α1 subunit (FIG. 13). Taken together, the data indicate that the inventors have developed an effective protocol for manipulating cellular Na+/K+-ATPase.

This protocol offers additional advantages over the widely used ouabain selection protocol for expression of mutated Na+/K+-ATPase in ouabain-sensitive cell lines (23-26).

First, the present protocol makes it possible to deplete endogenous Na+/K+-ATPase, allowing the investigators to study the effects of decreases in Na+/K+-ATPase expression on cellular function.

Second, the present protocol does not require using ouabain to force the expression of the transfected Na+/K+-ATPase. This is important in view of recent studies showing that ouabain stimulates the signaling function of the Na+/K+-ATPase and induces the endocytosis of the enzyme.

Third, the present protocol is useful for determining the exogenous/mutant Na+/K+-ATPase in the cells that have very low (less than 10%) endogenous Na+/K+-ATPase.

Fourth, the identified A4 siRNA are useful for silencing the α1 expression in cells derived from species other than human and pig because the human α1 cDNA sequence (nucleotide 2293 to nucleotide 2312) [SEQ ID NO: 38] targeted by A4 siRNA is conserved among all identified α1 subunits (but not other isoforms) from fish to human.

Fifth, rescuing PY-17 cells with different isoforms of Lp the Na+/K+-ATPase provides a way to uncover the isoform-specific signaling functions.

A Pool of Src-Interacting Na+/K+-ATPase

The Na+/K+-ATPase resides in caveolae with Src. FRET analysis indicates that the signaling Na+/K+-ATPase and Src are likely to interact and form a functional receptor complex. In vitro binding assay demonstrates that the α1 subunit and Src can interact directly via multiple domains and that the interaction keeps Src in an inactive state. The inventors now believe that there is an Src-interacting pool of Na+/K+-ATPase that not only regulates the basal Src activity, but also serves as a receptor for ouabain to stimulate Src-dependent tyrosine phosphorylation of multiple effectors.

First, because the signaling Na+/K+-ATPase binds and keeps Src in an inactive state, the inventors now believe that reduction of the endogenous Na+/K+-ATPase would deplete the Src-interacting pool of Na+/K+-ATPase, thus resulting in the Src activation. Indeed, as shown in FIG. 14, the α1 knockdown cells contain more active Src than the control P-11 cells. It is important to mention that the α1 knockdown did cause a significant increase in intracellular Na+ concentration in PY-17 cells. However, when intracellular Ca2+ was measured by fura-2, the steady state Ca2+ in PY-17 cells was comparable to that in P-11 cells. Thus, it is unlikely that increases in Src activity are due to changes in intracellular Na+ or Ca2+.

Second, when the α1 knockdown PY-17 cells were rescued by the rat α1, the inventors observed that the knock-in of the rat α1 was sufficient to replete the pool of Src-interacting Na+/K+-ATPase, leading to the restoration of basal Src activity.

Third, because the present described in vitro binding assay shows that the third intracellular domain of the α1 interacts and inhibits Src activity, the inventors now believe that a pumping-null mutant of the rat α1 should be able to bind and inhibit Src in live cells. Indeed, the inventors found that knock-in of rat α1 mutant D371E into PY-17 cells was also able to replete this Src-interacting pool of Na+/K+-ATPase and reduce the amount of active Src (FIG. 15).

In addition, both FRET analysis and co-immunoprecipitation assay showed that the pumping-null mutant could interact with Src in live cells (FIG. 16). Because expression of the pumping-null mutant would not reduce intracellular Na' concentration in PY-17 cells, these data also indicate that the Na+/K+-ATPase can interact and regulate Src independently of changes in intracellular Na+ concentration.

FAK is involved in regulation of cell proliferation, cell survival, and cell migration. It is also one of the effectors of Src. Binding of active Src to FAK leads to full activation of FAK and tyrosine phosphorylation of FAK Tyr$^{925}$, which results in the assembly of several downstream signaling modules including the activation of ERK1/2. The inventors found that depletion of cellular Na+/K+-ATPase not only activated Src but also stimulated tyrosine phosphorylation of FAK. Inhibition of Src by either PP2 or knock-in of a pump-null α1 mutant reduced Tyr(P)$^{925}$-FAK in PY-17 cells (FIG. 17). Consistently, the inventors have also observed that ouabain stimulated phosphorylation FAK in the control LLC-PK1 cells. These findings are significant. First, they support the notion that the Na+/K+-ATPase is an important regulator of protein kinases. Second, the regulatory effects of the Na+/K+-ATPase on Src and Src effector FAK depend on the ability of the Na+/K+-ATPase to interact with proteins, but not to pump ions. Third, the α1 depletion-induced Src activation is capable of generating downstream pathways. The inventors also note that FAK plays a key role in regulation of cell motility and that depletion of α1 in epithelial cells affects the formation of tight junctions and cell motility. Thus, the inventors now believe that the role of α1 depletion and subsequent activation of FAK in the regulation of cell migration are important.

Ouabain-induced signal transduction appears to be initiated by the activation of Src. Because ouabain uses the Na+/K+-ATPase•Src complex as a functional receptor, the inventors now believe that the ouabain-induced activation of Src should correlate with the size of the pool of Src-interacting Na+/K+-ATPase. Indeed, the inventors found that the effect of ouabain on Src activation correlated inversely with cellular levels of the Na+/K+-ATPase. Although ouabain induced a modest activation of Src in A4-11 cells, it failed to activate Src in PY-17 cells. Because Src is required to transmit the ouabain signal to many downstream effectors, the examples herein further show that the a/K-ATPase•Src complex is the sole receptor for ouabain to provoke the protein kinase cascades. This is further supported by the following observations. First, rescuing PY-17 cells with the rat α1 restored the effect of ouabain on Src and ERK1/2. Second, because the rescued cells expressed the ouabain-insensitive rat α1, a much higher ouabain concentration was required to stimulate Src and subsequently ERK1/2 in AAC-19 cells (FIG. 18). Third, the inventors have developed a powerful protocol for manipulating the cellular Na+/K+-ATPase that has allowed further characterization of the signaling properties of the Na+/K+-ATPase. Fourth, these new findings show that the Na+/K+-ATPase is an important receptor capable of transmitting ouabain signals via protein kinases. Fifth, because Src is actively involved in control of cell growth, the inventors herein now show that there is a need for re-examining the issue of whether the Na+/K+-ATPase-mediated repression of Src and ouabain-provoked activation of Src play a role in cancer biology.

EXAMPLE III

Further mapping of specific domains in Na+/K+-ATPase that interact and inhibit Src is shown in FIGS. 19A-D. The results showed that ND1, which contains 57 amino acids, binds Src. FIG. 19A shows the Scheme of Na+/K+-ATPase α1 and CD3 domain. FIG. 19B shows the amino acid sequence of ND1. [SEQ ID NO: 1] LTQNRMTVAHMWS-DNQIHEADTTENQSGVSFDKTSATWLA-LSRIAGLCNRAVFQANQ.

FIG. 19C shows the in vitro binding assay using GST-tagged α1 truncations and His-Src. FIG. 19D shows that this peptide is conserved in different species and different isoforms of Na/K-ATPase. [SEQ ID NOS: 2-33].

EXAMPLE IV

Further mapping of specific domains in Src that interact with Na+/K+-ATPase is shown in FIGS. 20A-C. The results showed that KD1 which contains 54 amino acids binds Na+/K+-ATPase. FIG. 20A shows the schematic structure of Src and its kinase domain. FIG. 20B shows the KD1 peptide from Src binds with Na+/K+-ATPase. [SEQ ID NO: 34] (LR-LEVKLGQGCFGEVWMGTWNGTTRVAIK-TLKPGTMSPEAFLQEAQVMKKLRHE).

FIG. 20C shows the in vitro binding assay using GST-tagged Src truncations and purified Na+/K+-ATPase.

EXAMPLE V

The activity assay confirms that ND1 and KD1 are involved in Na+/K+-ATPase mediated regulation of Src. FIG. 21 shows that the GST-ND1 of Na+/K+-ATPase inhibits Src activity and the inhibition effect can be competed by GST-KD1 of Src.

FIGS. 22A-B shows that ND1 is effective in blocking Src activity in live cells. ND1, ND and CD3 decrease Src phosphorylation in LLC-PK1 cells. FIG. 22A shows that the LLC-PK1 cells were transient-transfected with YFP-tagged ND1, ND, and CD3 for 24 h. Cells were then lysed in RIPA buffer and probed for pY418. YFP were also transient-transfected into LLC-PK1 cells as control. FIG. 22 B shows the quantitation data from three experiments. * p<0.05.

EXAMPLE VI

ND1 also inhibits prostate cancer cell (DU145) growth. FIG. 23 shows that YFP-ND1 stops human prostate cancer cell (DU145) growth. 2.0 µg of pYFP-C1 or pYFP-C1-ND1 plasmid was transfected into LLC-PK1 cells with Lipofectamine 2000. After 48 hr, cell numbers were counted with Trypan Blue Staining

EXAMPLE VII

Identification of P3 as a potent Src inhibitor: Mapping of ND1 has identified a 20 amino acid peptide (P-3) from ND1 that inhibits Src. FIGS. 24A-B shows that Peptide 3 from ND1 significantly inhibits Src activity. FIG. 24A shows the P3 peptide sequence [SEQ ID NO: 2] SATWLALSRIA-GLCNRAVFQ.

FIG. 24B shows the results when purified Src was incubated with P-3 peptide at 37° C. for 20 min and 2 mM ATP was added for additional 5 min. The reaction was stopped by adding 5× loading buffer. pY418 was probed to measure Src activation.

FIG. 28 shows the sequences of peptides (TAT and AP) that enhance the cell membrane permeability of macromolecules.

Conjugating TAT or AP to P3 makes it cell membrane permeable: FIG. 29A shows the sequences of TAT or AP-conjugated Src peptide inhibitors (TAT-P3 or AP-P3). FIG.

29B shows that the new peptides inhibit Src in vitro. FIG. 29C shows that a FITC-conjugated TAT-P3 is targeted to the cell membrane. FIG. 29D shows that addition of TAT-P3 or AP-P3 to DU145 cells inhibited cell growth.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The references discussed above and the following references, to the extent that they provide exemplary procedural or other details supplementary to those set forth herein, are specifically incorporated herein by reference. Citation of a reference herein shall not be construed as an admission that such is prior art to the present invention.

Abram, C. L., and Courtneidge, S. A. (2000). Src family tyrosine kinases and growth factor signaling. Exp. Cell Res. 254, 1-13.

Aizman, O., Uhlen, P., Lal, M., Brismar, H., and Aperia, A. (2001). Ouabain, a steroid hormone that signals with slow calcium oscillations. Proc. Natl. Acad. Sci. USA 98, 13420-13424.

Aydemir-Koksoy, A., Abramowitz, J., and Allen, J. C. (2001). Ouabain-induced signaling and vascular smooth muscle cell proliferation. J. Biol. Chem. 276, 46605-46611.

Baker, P. F., and Willis, J. S. (1969). On the number of sodium pumping sites in cell membranes. Biochim. Biophys. Acta 183, 646-649.

Baker, P. F., and Willis, J. S. (1970). Potassium ions and the binding of cardiac glycosides to mammalian cells. Nature 226, 521-523.

Barwe, S. P., Anilkumar, G., Moon, S. Y., Zheng, Y., Whitelegge, J. P., Rajasekaran, S. A., and Rajasekaran, A. K. (2005). Novel role for Na,K-ATPase in phosphatidylinositol 3-kinase signaling and suppression of cell motility. Mol. Biol. Cell 16, 1082-1094.

Berkers, J. A., van Bergen en Henegouwen, P. M., and Boonstra, J. (1991). Three classes of epidermal growth factor receptors on HeLa cells. J. Biol. Chem. 266, 922-927.

Boggon, T. J., and Eck, M. J. (2004). Structure and regulation of Src family kinases. Oncogene 23, 7918-7927.

Brown, M. T., and Cooper, J. A. (1996). Regulation, substrates and functions of Src. Biochim. Biophys. Acta 1287, 121-149.

Devarajan, P., Scaramuzzino, D. A., and Morrow, J. S. (1994). Ankyrin binds to two distinct cytoplasmic domains of Na,K-ATPase alpha subunit. Proc. Natl. Acad. Sci. USA 91, 2965-2969.

Dolgova, N., Mast, N., Akimova, O., Rubtsov, A., and Lopina, O. (2003). Proteins binding to alpha1beta1 isozyme of Na,K-ATPase. Ann. NY Acad. Sci. 986, 527-529.

Emanuel, J. R., Schulz, J., Zhou, X. M., Kent, R. B., Housman, D., Cantley, L., and Levenson, R. (1988) J. Biol. Chem. 263, 7726-7733.

Fedorova, O. V., Talan, M. I., Agalakova, N. I., Lakatta, E. G., and Bagrov, A. Y. (2002). Endogenous ligand of alpha(1) sodium pump, marinobufagenin, is a novel mediator of sodium chloride-dependent hypertension. Circulation 105, 1122-1127.

Ferrandi, M., Molinari, I., Barassi, P., Minotti, E., Bianchi, G., and Ferrari, P. (2004). Organ hypertrophic signaling within caveolae membrane subdomains triggered by ouabain and antagonized by PST 2238. J. Biol. Chem. 279, 33306-33314.

Fire, A., Xu, S., Montgomery, M. K., Kostas, S. A., Driver, S. E., and Mello, C. C. (1998) Nature 391, 806-811.

Haas, M., Askari, A., and Xie, Z. (2000). Involvement of Src and epidermal growth factor receptor in the signal-transducing function of Na+/K+-ATPase. J. Biol. Chem. 275, 27832-27837.

Haas, M., Wang, H., Tian, J., and Xie, Z. (2002). Src-mediated inter-receptor cross-talk between the Na+/K+-ATPase and the epidermal growth factor receptor relays the signal from ouabain to mitogen-activated protein kinases. J. Biol. Chem. 277, 18694-18702.

Hamlyn, J. M., Blaustein, M. P., Bova, S., DuCharme, D. W., Harris, D. W., Mandel, F., Mathews, W. R., and Ludens, J. H. (1991). Identification and characterization of a ouabain-like compound from human plasma. Proc. Natl. Acad. Sci. USA 88, 6259-6263.

Haskell, M. D., Slack, J. K., Parsons, J. T., and Parsons, S. J. (2001) Chem. Rev. 101, 2425-2440.

Huang, L., Li, H., and Xie, Z. (1997). Ouabain-induced hypertrophy in cultured cardiac myocytes is accompanied by changes in expression of several late response genes. J. Mol. Cell. Cardiol. 29, 429-437.

Ihle, J. N. (1994). The Janus kinase family and signaling through members of the cytokine receptor superfamily. Proc. Soc. Exp. Biol. Med. 206, 268-272.

Jewell, E. A., and Lingrel, J. B. (1991) J. Biol. Chem. 266, 16925-16930.

Jorgensen, P. L. (1974). Purification and characterization of (Na+ plus K+)ATPase. 3. Purification from the outer medulla of mammalian kidney after selective removal of membrane components by sodium dodecylsulphate. Biochim. Biophys. Acta 356, 36-52.

Jorgensen, P. L. (1988). Purification of Na+,K+-ATPase: enzyme sources, preparative problems, and preparation from mammalian kidney. Methods Enzymol. 156, 29-43.

Kanagawa, M., Watanabe, S., Kaya, S., Togawa, K., Imagawa, T., Shimada, A., Kikuchi, K., and Taniguchi, K. (2000). Membrane enzyme systems responsible for the Ca(2+)-dependent phosphorylation of Ser(27), the independent phosphorylation of Tyr(10) and Tyr(7), and the dephosphorylation of these phosphorylated residues in the alpha-chain of H/K-ATPase. J. Biochem. (Tokyo) 127, 821-828.

Kent, R. B., Emanuel, J. R., Ben Neriah, Y., Levenson, R., and Housman, D. E. (1987) Science 237, 901-903.

Kaplan, J. H. (2002). Biochemistry of Na,K-ATPase. Annu. Rev. Biochem. 71, 511-535.

Kim, D., Barry, W. H., and Smith, T. W. (1984) J. Pharmacol. Exp. Ther. 231, 326-333.

Kometiani, P., Li, J., Gnudi, L., Kahn, B. B., Askari, A., and Xie, Z. (1998). Multiple signal transduction pathways link Na+/K+-ATPase to growth-related genes in cardiac myocytes. The roles of Ras and mitogen-activated protein kinases. J. Biol. Chem. 273, 15249-15256.

Lingrel, J. B., and Kuntzweiler, T. (1994). Na+,K(+)-ATPase. J. Biol. Chem. 269, 19659-19662.

Liu, L., Abramowitz, J., Askari, A., and Allen, J. C. (2004) Am. J. Physiol. 287, H2173-H2182.

Liu, J., Kesiry, R., Periyasamy, S. M., Malhotra, D., Xie, Z., and Shapiro, J. I. (2004) Kidney Int. 66, 227-241.

Liu, L., Mohammadi, K., Aynafshar, B., Wang, H., Li, D., Liu, J., Ivanov, V., Xie, Z., and Askari, A. (2003) Am. J. Physiol. 284, C1550-C1560.

Liu, J., Tian, J., Haas, M., Shapiro, J. I., Askari, A., and Xie, Z. (2000). Ouabain interaction with cardiac Na+/K+-ATPase initiates signal cascades independent of changes in intracellular Na+ and Ca2+ concentrations. J. Biol. Chem. 275, 27838-27844.

Lowry, W. E., Huang, J., Ma, Y. C., Ali, S., Wang, D., Williams, D. M., Okada, M., Cole, P. A., and Huang, X. Y. (2002). Csk, a critical link of g protein signals to actin cytoskeletal reorganization. Dev. Cell 2, 733-744.

Ma, Y. C., Huang, J., Ali, S., Lowry, W., and Huang, X. Y. (2000). Src tyrosine kinase is a novel direct effector of G proteins. Cell 102, 635-646.

Masaki, T., Shiratori, Y., Okada, H., Nishioka, M., Taniguchi, K., Hatanaka, Y., and Omata, M. (2000). pp 60c-src activation in gastric carcinoma: a preliminary study. Am. J. Gastroenterol. 95, 837-838.

McCall, D. (1979). Cation exchange and glycoside binding in cultured rat heart cells. Am. J. Physiol. 236, C87-C95.

Miyakawa-Naito, A., Uhlen, P., Lal, M., Aizman, O., Mikoshiba, K., Brismar, H., Zelenin, S., and Aperia, A. (2003) J. Biol. Chem. 278, 50355-50361.

Mohammadi, K., Liu, L., Tian, J., Kometiani, P., Xie, Z., and Askari, A. (2003). Positive inotropic effect of ouabain on isolated heart is accompanied by activation of signal pathways that link Na+/K+-ATPase to ERK1/2. J. Cardiovasc. Pharmacol. 41, 609-614.

Mohammadi, K., Kometiani, P., Xie, Z., and Askari, A. (2001) J. Biol. Chem. 276, 42050-42056.

Ohtsubo, M., Noguchi, S., Takeda, K., Morohashi, M., and Kawamura, M. (1990) Biochim. Biophys. Acta 1021, 157-160.

Paul, C. P., Good, P. D., Winer, I., and Engelke, D. R. (2002) Nat. Biotechnol. 20, 505-508.

Petrosian, S. A., Carr, D. L., Guerrero, G., and Pressley, T. A. (1998) Arch. Biochem. Biophys. 357, 249-258.

Pierdomenico, S. D., Bucci, A., Manunta, P., Rivera, R., Ferrandi, M., Hamlyn, J. M., Lapenna, D., Cuccurullo, F., and Mezzetti, A. (2001). Endogenous ouabain and hemodynamic and left ventricular geometric patterns in essential hypertension. Am. J. Hypertens. 14, 44-50.

Price, E. M., and Lingrel, J. B. (1988) Biochemistry 27, 8400-8408.

Rajasekaran, S. A., Palmer, L. G., Quan, K., Harper, J. F., Ball, W. J., Jr., Bander, N. H., Peralta Soler, A., and Rajasekaran, A. K. (2001) Mol. Biol. Cell 12, 279-295.

Schaller, M. D. (2001) Biochim. Biophys. Acta 1540, 1-21.

Scheiner-Bobis, G., and Schoner, W. (2001). A fresh facet for ouabain action. Nat. Med. 7, 1288-1289.

Schlaepfer, D. D., Hauck, C. R., and Sieg, D. J. (1999) Prog. Biophys. Mol. Biol. 71, 435-478.

Schlaepfer, D. D., Broome, M. A., and Hunter, T. (1997) Mol. Cell. Biol. 17, 1702-1713.

Schlaepfer, D. D., Hanks, S. K., Hunter, T., and van der Geer, P. (1994) Nature 372, 786-791.

Schulte, R. J., and Sefton, B. M. (2003). Inhibition of the activity of SRC and Abl tyrosine protein kinases by the binding of the Wiskott-Aldrich syndrome protein. Biochemistry 42, 9424-9430.

Skou, J. C. (1957) Biochim. Biophys. Acta 23, 394-401.

Sobko, A., Peretz, A., and Attali, B. (1998). Constitutive activation of delayed rectifier potassium channels by a Src family tyrosine kinase in Schwann cells. EMBO J. 17, 4723-4734.

Tatosyan, A. G., and Mizenina, O. A. (2000). Kinases of the Src family: structure and functions. Biochemistry (Mosc.) 65, 49-58.

Tian, J., Cai, T., Yuan, Z., Wang, H., Liu, L., Haas, M., Maksimova, E., Huang, X. Y., and Xie, Z. J. (2006) Mol. Biol. Cell 17, 317-326.

Tian, J., Gong, X., and Xie, Z. (2001). Signal-transducing function of Na+-K-ATPase is essential for ouabain's effect on [Ca2+]i in rat cardiac myocytes. Am. J. Physiol. Heart Circ. Physiol. 281, H1899-H1907.

Tiran, Z., Peretz, A., Attali, B., and Elson, A. (2003). Phosphorylation-dependent regulation of Kv2.1 Channel activity at tyrosine 124 by Src and by protein-tyrosine phosphatase epsilon. J. Biol. Chem. 278, 17509-17514.

Thomas, S. M., and Brugge, J. S. (1997) Annu. Rev. Cell Dev. Biol. 13, 513-609.

Toyoshima, C., and Nomura, H. (2002). Structural changes in the calcium pump accompanying the dissociation of calcium. Nature 418, 605-611.

Wan, Y. S., Wang, Z. Q., Voorhees, J., and Fisher, G. (2001). EGF receptor crosstalks with cytokine receptors leading to the activation of c-Jun kinase in response to UV irradiation in human keratinocytes. Cell Signal 13, 139-144.

Wang, H., Haas, M., Liang, M., Cai, T., Tian, J., Li, S., and Xie, Z. (2004). Ouabain assembles signaling cascades through the caveolar Na+/K+-ATPase. J. Biol. Chem. 279, 17250-17259.

Xie, Z. (2001). Ouabain interaction with cardiac Na+/K+-ATPase reveals that the enzyme can act as a pump and as a signal transducer. Cell. Mol. Biol. (Noisy-le-grand) 47, 383-390.

Xie, Z., Kometiani, P., Liu, J., Li, J., Shapiro, J. I., and Askari, A. (1999). Intracellular reactive oxygen species mediate the linkage of Na+/K+-ATPase to hypertrophy and its marker genes in cardiac myocytes. J. Biol. Chem. 274, 19323-19328.

Xie, Z., Wang, Y., Liu, G., Zolotarjova, N., Periyasamy, S. M., and Askari, A. (1996). Similarities and differences between the properties of native and recombinant Na+/K+-ATPases. Arch. Biochem. Biophys. 330, 153-162.

Xie, Z. J., Wang, Y. H., Ganjeizadeh, M., McGee, R., Jr., and Askari, A. (1989) Anal. Biochem. 183, 215-219.

Young, M. A., Gonfloni, S., Superti-Furga, G., Roux, B., and Kuriyan, J. (2001). Dynamic coupling between the SH2 and SH3 domains of c-Src and Hck underlies their inactivation by C-terminal tyrosine phosphorylation. Cell 105, 115-126.

Yu, X. M., Askalan, R., Keil, G. J., 2nd, and Salter, M. W. (1997). NMDA channel regulation by channel-associated protein tyrosine kinase Src. Science 275, 674-678.

Yuan, Z., Cai, T., Tian, J., Ivanov, A. V., Giovannucci, D. R., and Xie, Z. (2005). Na+/K+-ATPase tethers phospholipase C and IP3 receptor into a calcium regulatory complex. Mol. Biol. Cell 16, 4034-4045.

Yudowski, G. A., Efendiev, R., Pedemonte, C. H., Katz, A. I., Berggren, P. O., and Bertorello, A. M. (2000). Phosphoinositide-3 kinase binds to a proline-rich motif in the Na+, K+-ATPase alpha subunit and regulates its trafficking. Proc. Natl. Acad. Sci. USA 97, 6556-6561.

What is claimed is:

1. A pharmaceutical composition for regulation of one or more signaling pathways involved in fibrosis, the composition comprising:
one or more Src and Src family kinases inhibitors comprised of one or more isolated peptides, or fragments thereof, that do not inhibit the ion pumping function of Na+/K+-ATPase;
wherein the one or more isolated peptides comprises the active isolated Src-inhibitory peptide (P3) consisting of the amino acid sequence of SEQ ID NO: 2.

2. The composition of claim 1, wherein the one or more Src and Src family kinases inhibitors or activators modulates one or more signaling pathways that are related to cardiac fibrosis.

3. The composition of claim 1, wherein the Src-modulating peptide (P3) is conjugated to a penetratin (TAT) peptide.

4. The composition of claim 3, wherein the conjugated TAT-P3 peptide consists of the amino acid sequence of SEQ ID NO: 49.

5. The composition of claim 1, wherein the Src-modulating peptide (P3) is conjugated to an antennapedia (AP) peptide.

6. The composition of claim 5, wherein the AP-P3 peptide consists of the amino acid sequence of SEQ ID NO: 50.

* * * * *